(12) United States Patent
Hunter et al.

(10) Patent No.: US 10,154,923 B2
(45) Date of Patent: *Dec. 18, 2018

(54) DROP GENERATING DEVICE

(71) Applicant: Eyenovia, Inc., New York, NY (US)

(72) Inventors: Charles Eric Hunter, Boone, NC (US); Bernard L. Ballou, Jr., Raleigh, NC (US); Jurgen Klaus Vollrath, Indian Trail, NC (US); Arthur H. Tew, Pinehurst, NC (US); Joshua Richard Brown, Hickory, NC (US); James Thornhill Leath, Burlington, NC (US); Nathan R. Faulks, Boone, NC (US); Bradley G. Johnson, Boone, NC (US); J. Sid Clements, Boone, NC (US); Phillip E. Russell, Boone, NC (US); John H. Hebrank, Durham, NC (US); Tsontcho Inachulev, San Mateo, CA (US); Mark Packer, Eugene, OR (US); Troy Elliott, Raleigh, NC (US); Walter M. Fierson, Arcadia, CA (US); Thomas J. Lindner, Corvallis, OR (US)

(73) Assignee: Eyenovia, Inc., New York, NY (US)

( * ) Notice: Subject to any disclaimer, the term of this patent is extended or adjusted under 35 U.S.C. 154(b) by 1087 days.

This patent is subject to a terminal disclaimer.

(21) Appl. No.: 14/200,268

(22) Filed: Mar. 7, 2014

(65) Prior Publication Data

US 2014/0187969 A1 Jul. 3, 2014

Related U.S. Application Data

(63) Continuation of application No. 13/184,484, filed on Jul. 15, 2011, now Pat. No. 8,684,980.

(Continued)

(51) Int. Cl.
*A61M 35/00* (2006.01)
*A61F 9/00* (2006.01)
(Continued)

(52) U.S. Cl.
CPC .......... *A61F 9/0008* (2013.01); *A61B 5/0059* (2013.01); *A61B 5/4839* (2013.01);
(Continued)

(58) Field of Classification Search
CPC ................ A61F 9/0008; A61M 15/025; G06F 19/3406; G06F 19/3418; G06F 19/322;
(Continued)

(56) References Cited

U.S. PATENT DOCUMENTS 1,482,747 A 2/1924 Howe
1,988,637 A 1/1935 Tinkham
(Continued)

FOREIGN PATENT DOCUMENTS

CN 1799529 7/2006
DE 196 16 300 A1 10/1997
(Continued)

OTHER PUBLICATIONS

"Alcon®: Sharing One Vision," 2009 Annual Report, 46 pages (2009).
(Continued)

*Primary Examiner* — Andrew J Mensh
(74) *Attorney, Agent, or Firm* — Polsinelli PC

(57) ABSTRACT

A method of delivering safe, suitable, and repeatable dosages to a subject for topical, oral, nasal, or pulmonary use and a device for droplet ejection includes a fluid delivery system capable of delivering a defined volume of the fluid in the form of droplets having properties that afford adequate and repeatable high percentage deposition upon application. The method and device include a housing, a reservoir (Continued)

disposed within the housing for receiving a volume of fluid, an ejector mechanism configured to eject a stream of droplets having an average ejected droplet diameter greater than 15 microns, the stream of droplets having low entrained airflow such that the stream of droplets deposit on the eye of the subject during use.

15 Claims, 37 Drawing Sheets

Related U.S. Application Data

(60) Provisional application No. 61/400,864, filed on Jul. 15, 2010, provisional application No. 61/401,850, filed on Aug. 20, 2010, provisional application No. 61/401,920, filed on Aug. 20, 2010, provisional application No. 61/401,918, filed on Aug. 20, 2010, provisional application No. 61/401,848, filed on Aug. 20, 2010, provisional application No. 61/401,849, filed on Aug. 20, 2010, provisional application No. 61/462,576, filed on Feb. 4, 2011, provisional application No. 61/462,791, filed on Feb. 5, 2011, provisional application No. 61/463,280, filed on Feb. 15, 2011, provisional application No. 61/516,462, filed on Apr. 4, 2011, provisional application No. 61/516,496, filed on Apr. 4, 2011, provisional application No. 61/516,495, filed on Apr. 4, 2011, provisional application No. 61/516,694, filed on Apr. 6, 2011.

(51) Int. Cl.

| | |
|---|---|
| *G06F 19/00* | (2018.01) |
| *A61B 5/00* | (2006.01) |
| *A61M 15/00* | (2006.01) |
| *G16H 40/63* | (2018.01) |
| *A61M 15/02* | (2006.01) |
| *G16H 10/60* | (2018.01) |
| *G16H 15/00* | (2018.01) |

(52) U.S. Cl.
CPC ....... *A61M 15/008* (2014.02); *G06F 19/3418* (2013.01); *G16H 40/63* (2018.01); *A61M 15/0083* (2014.02); *A61M 15/025* (2014.02); *G06F 19/3456* (2013.01); *G16H 10/60* (2018.01); *G16H 15/00* (2018.01)

(58) Field of Classification Search
CPC ............. G06F 19/3456; G06F 19/3487; A61B 5/0059; A61B 5/4839
USPC ........................................ 604/294, 296, 298
See application file for complete search history.

(56) References Cited

U.S. PATENT DOCUMENTS

| | | | | | |
|---|---|---|---|---|---|
| 2,189,643 | A | | 2/1940 | Ward | |
| 2,200,008 | A | | 5/1940 | Nowak | |
| 2,249,608 | A | | 7/1941 | Greene | |
| 2,322,808 | A | | 6/1943 | Hothersall | |
| 2,552,857 | A | | 5/1951 | Knapp | |
| 2,595,317 | A | | 5/1952 | White | |
| 2,987,439 | A | | 6/1961 | Wittlinger | |
| 3,170,462 | A | | 2/1965 | Hall | |
| 3,187,757 | A | | 6/1965 | Jones et al. | |
| 3,237,809 | A | | 3/1966 | Daragan et al. | |
| 3,310,830 | A | | 3/1967 | Gattone | |
| 3,314,426 | A | | 4/1967 | Caroll | |
| 3,439,674 | A | | 4/1969 | Lelicoff | |
| 3,602,399 | A | | 8/1971 | Litman et al. | |
| 3,658,257 | A | | 4/1972 | Rood | |
| 3,709,235 | A | | 1/1973 | Washburn et al. | |
| 3,779,245 | A | | 12/1973 | Windsor | |
| 3,780,950 | A | | 12/1973 | Brennan | |
| 3,795,351 | A | | 3/1974 | Lehmann | |
| 3,812,854 | A | | 5/1974 | Michaels et al. | |
| 3,826,258 | A | | 7/1974 | Abraham | |
| 3,845,764 | A | | 11/1974 | Windsor | |
| 3,901,443 | A | | 8/1975 | Mitsui et al. | |
| 3,906,949 | A | | 9/1975 | Holland | |
| 3,913,575 | A | | 10/1975 | Windsor | |
| 3,934,585 | A | * | 1/1976 | Maurice | ............... A61F 9/0008 222/420 |
| 4,002,168 | A | | 1/1977 | Petterson | |
| 4,012,798 | A | | 3/1977 | Liautaud | |
| 4,052,985 | A | | 10/1977 | Coleman et al. | |
| 4,067,499 | A | | 1/1978 | Cohen | |
| 4,098,431 | A | | 7/1978 | Palmer et al. | |
| D249,709 | S | | 9/1978 | Trovinger | |
| 4,119,096 | A | | 10/1978 | Drews | |
| 4,122,556 | A | | 10/1978 | Poler | |
| 4,131,115 | A | | 12/1978 | Peng | |
| 4,173,226 | A | | 11/1979 | Shell | |
| 4,175,704 | A | | 11/1979 | Cohen | |
| 4,175,706 | A | | 11/1979 | Gerstmann | |
| 4,264,837 | A | | 4/1981 | Gaboriaud | |
| 4,296,071 | A | | 10/1981 | Weiss et al. | |
| 4,319,155 | A | | 3/1982 | Nakai et al. | |
| 4,323,530 | A | | 4/1982 | Voss et al. | |
| 4,338,936 | A | | 7/1982 | Nelson | |
| 4,356,528 | A | | 10/1982 | Coffee | |
| 4,381,533 | A | | 4/1983 | Coffee | |
| 4,388,343 | A | | 6/1983 | Voss et al. | |
| 4,390,542 | A | | 6/1983 | Schachar | |
| 4,398,909 | A | | 8/1983 | Portnoff | |
| 4,465,234 | A | | 8/1984 | Maehara et al. | |
| 4,471,890 | A | | 9/1984 | Dougherty | |
| 4,476,515 | A | | 10/1984 | Coffee | |
| 4,479,609 | A | | 10/1984 | Maeda et al. | |
| 4,493,119 | A | | 1/1985 | Baumann | |
| 4,533,082 | A | | 8/1985 | Maehara et al. | |
| 4,543,096 | A | | 9/1985 | Keene | |
| 4,544,570 | A | | 10/1985 | Plunkett et al. | |
| 4,564,016 | A | | 1/1986 | Maurice et al. | |
| 4,580,721 | A | | 4/1986 | Coffee et al. | |
| 4,605,167 | A | | 8/1986 | Maehara | |
| 4,605,398 | A | | 8/1986 | Herrick | |
| 4,627,845 | A | | 12/1986 | DeMotte | |
| 4,641,384 | A | | 2/1987 | Landsberger et al. | |
| 4,642,581 | A | | 2/1987 | Erickson | |
| 4,658,290 | A | | 4/1987 | McKenna et al. | |
| 4,659,014 | A | | 4/1987 | Soth et al. | |
| 4,679,551 | A | | 7/1987 | Anthony | |
| 4,685,906 | A | | 8/1987 | Murphy | |
| 4,701,167 | A | | 10/1987 | Chekan | |
| 4,702,418 | A | | 10/1987 | Carter et al. | |
| 4,706,848 | A | | 11/1987 | D'Andrade | |
| 4,740,206 | A | | 4/1988 | Aliirldr | |
| 4,742,713 | A | | 5/1988 | Abe et al. | |
| 4,750,650 | A | | 6/1988 | Ling | |
| 4,750,902 | A | | 6/1988 | Wuchinich et al. | |
| 4,758,237 | A | | 7/1988 | Sacks | |
| 4,758,727 | A | | 7/1988 | Tomei et al. | |
| 4,759,755 | A | | 7/1988 | Hein et al. | |
| 4,779,768 | A | | 10/1988 | St. Amand | |
| 4,784,652 | A | | 11/1988 | Wikström | |
| 4,790,479 | A | | 12/1988 | Matsumoto et al. | |
| 4,792,334 | A | | 12/1988 | Py | |
| 4,793,339 | A | | 12/1988 | Matsumoto et al. | |
| 4,796,807 | A | | 1/1989 | Bendig et al. | |
| 4,798,599 | A | | 1/1989 | Thomas | |
| 4,809,914 | A | | 3/1989 | Goncalves | |
| 4,815,661 | A | | 3/1989 | Anthony | |
| 4,826,025 | A | | 5/1989 | Abiko et al. | |
| 4,850,534 | A | | 7/1989 | Takahashi et al. | |
| 4,863,073 | A | | 9/1989 | Burt et al. | |
| 4,863,443 | A | | 9/1989 | Hornung | |
| 4,863,457 | A | | 9/1989 | Lee | |
| 4,871,091 | A | | 10/1989 | Preziosi | |

(56) References Cited

U.S. PATENT DOCUMENTS

| | | |
|---|---|---|
| 4,877,989 A | 10/1989 | Drews et al. |
| 4,880,146 A | 11/1989 | Hudgins |
| 4,881,183 A | 11/1989 | Lizutaud |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A | 8/1990 | Booth et al. |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,204 A | 12/1991 | Smith et al. |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A | 10/1992 | Ross et al. |
| 5,163,929 A | 11/1992 | Py |
| 5,164,740 A | 11/1992 | Ivri |
| 5,170,782 A | 12/1992 | Kocinski |
| 5,171,306 A | 12/1992 | Vo |
| 5,178,856 A | 1/1993 | Takahashi et al. |
| 5,193,745 A | 3/1993 | Holm |
| 5,201,726 A | 4/1993 | Kirkham |
| 5,203,506 A | 4/1993 | Gross et al. |
| 5,226,538 A | 7/1993 | Roselle |
| 5,252,318 A | 10/1993 | Joshi et al. |
| 5,259,385 A | 11/1993 | Miller et al. |
| 5,261,601 A | 11/1993 | Ross et al. |
| 5,265,288 A | 11/1993 | Allison |
| 5,267,986 A | 12/1993 | Py |
| 5,276,867 A | 1/1994 | Kenley et al. |
| 5,299,739 A | 4/1994 | Takahashi et al. |
| 5,316,159 A | 5/1994 | Douglas et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |
| 5,431,663 A | 7/1995 | Carter |
| 5,435,282 A | 7/1995 | Haber et al. |
| 5,435,465 A | 7/1995 | El-Amin |
| 5,462,586 A | 10/1995 | Sugiyama et al. |
| 5,485,828 A | 1/1996 | Hauser |
| 5,496,411 A | 3/1996 | Candy |
| 5,499,751 A | 3/1996 | Meyer |
| D368,774 S | 4/1996 | Py |
| 5,515,841 A | 5/1996 | Robertson et al. |
| 5,518,179 A | 5/1996 | Humberstone et al. |
| 5,529,055 A | 6/1996 | Gueret |
| D374,719 S | 10/1996 | Py |
| 5,564,016 A | 10/1996 | Korenshtein |
| 5,584,823 A | 12/1996 | Valberg |
| 5,586,550 A | 12/1996 | Ivri et al. |
| 5,588,564 A | 12/1996 | Hutson et al. |
| 5,607,410 A | 3/1997 | Branch |
| 5,613,957 A | 3/1997 | Py |
| 5,614,545 A | 3/1997 | Martin et al. |
| 5,630,793 A | 5/1997 | Rowe |
| 5,657,926 A | 8/1997 | Toda |
| 5,665,079 A | 9/1997 | Stahl |
| 5,685,869 A | 11/1997 | Py |
| 5,687,874 A | 11/1997 | Omori et al. |
| 5,707,636 A | 1/1998 | Rodriguez et al. |
| 5,724,021 A | 3/1998 | Perrone |
| 5,730,723 A | 3/1998 | Castellano et al. |
| 5,735,811 A | 4/1998 | Brisken |
| 5,740,947 A | 4/1998 | Flaig et al. |
| 5,746,728 A | 5/1998 | Py |
| 5,758,637 A | 6/1998 | Ivri et al. |
| 5,803,106 A | 9/1998 | Cohen et al. |
| 5,807,357 A | 9/1998 | Kang |
| 5,823,428 A | 10/1998 | Humberstone et al. |
| 5,838,350 A | 11/1998 | Newcombe et al. |
| 5,843,109 A | 12/1998 | Mehta et al. |
| 5,855,322 A | 1/1999 | Py |
| 5,881,956 A | 3/1999 | Cohen et al. |
| 5,893,515 A | 4/1999 | Hahn et al. |
| 5,894,841 A | 4/1999 | Voges |
| 5,938,117 A | 8/1999 | Ivri |
| D413,668 S | 9/1999 | Mannberg et al. |
| 5,957,943 A | 9/1999 | Vaitekunas |
| 5,970,974 A | 10/1999 | Van Der Linden et al. |
| 5,996,903 A | 12/1999 | Asai et al. |
| 5,997,518 A | 12/1999 | Laibovitz et al. |
| 6,008,468 A | 12/1999 | Tanaka et al. |
| 6,027,450 A | 2/2000 | Brown |
| 6,039,565 A | 3/2000 | Chou et al. |
| 6,062,212 A | 5/2000 | Davison et al. |
| 6,083,922 A | 7/2000 | Montgomery |
| 6,085,740 A | 7/2000 | Ivri et al. |
| 6,135,427 A | 10/2000 | Tsai |
| 6,152,383 A | 11/2000 | Chen |
| 6,159,188 A | 12/2000 | Laibovitz et al. |
| 6,193,683 B1 | 2/2001 | Ludin et al. |
| 6,203,759 B1 | 3/2001 | Pelc et al. |
| 6,216,966 B1 | 4/2001 | Prendergast et al. |
| 6,221,038 B1 | 4/2001 | Brisken |
| 6,228,046 B1 | 5/2001 | Brisken |
| 6,235,024 B1 | 5/2001 | Tu |
| 6,254,579 B1 | 7/2001 | Cogger et al. |
| 6,254,587 B1 | 7/2001 | Christ et al. |
| 6,263,872 B1 | 7/2001 | Schuster et al. |
| 6,273,342 B1 | 8/2001 | Terada et al. |
| 6,296,626 B1 | 10/2001 | Stein |
| 6,318,361 B1 | 11/2001 | Sosiak |
| 6,336,917 B1 | 1/2002 | Berke |
| 6,341,732 B1 | 1/2002 | Martin et al. |
| 6,357,442 B1 | 3/2002 | Casper et al. |
| 6,357,671 B1 | 3/2002 | Cewers |
| 6,367,685 B1 | 4/2002 | Jiang et al. |
| 6,394,363 B1 | 5/2002 | Arnott et al. |
| 6,398,737 B2 | 6/2002 | Moore et al. |
| 6,398,766 B1 | 6/2002 | Branch |
| 6,422,431 B2 | 7/2002 | Pelc et al. |
| 6,423,040 B1 | 7/2002 | Benktzon et al. |
| 6,425,888 B1 | 7/2002 | Embleton et al. |
| 6,427,682 B1 | 8/2002 | Klimowicz et al. |
| 6,442,423 B1 | 8/2002 | Domb et al. |
| 6,443,146 B1 | 9/2002 | Voges |
| 6,467,476 B1 | 10/2002 | Ivri et al. |
| 6,524,287 B1 | 2/2003 | Cogger |
| 6,526,976 B1 | 3/2003 | Baran |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |

(56) References Cited

U.S. PATENT DOCUMENTS

| | | |
|---|---|---|
| 6,554,801 B1 | 4/2003 | Steward et al. |
| 6,569,131 B1 | 5/2003 | Michael et al. |
| 6,569,387 B1 | 5/2003 | Furner et al. |
| 6,601,033 B1 | 8/2003 | Melanson et al. |
| 6,601,581 B1 | 8/2003 | Babaev |
| 6,612,302 B1 | 9/2003 | Rand |
| 6,615,824 B2 | 9/2003 | Power |
| 6,619,562 B2 | 9/2003 | Hamaguchi et al. |
| 6,622,720 B2 | 9/2003 | Hadimioglu |
| 6,629,646 B1 | 10/2003 | Ivri |
| 6,640,804 B2 | 11/2003 | Ivri et al. |
| 6,650,935 B1 | 11/2003 | Watmough |
| 6,651,650 B1 | 11/2003 | Yamamoto et al. |
| 6,659,364 B1 | 12/2003 | Humberstone et al. |
| 6,669,961 B2 | 12/2003 | Kim et al. |
| 6,676,034 B2 | 1/2004 | Tanaka et al. |
| 6,679,436 B1 | 1/2004 | Onishi et al. |
| 6,684,681 B1 | 2/2004 | Zombo |
| 6,684,879 B1 | 2/2004 | Coffee et al. |
| 6,719,770 B2 | 4/2004 | Laufer et al. |
| 6,732,944 B2 | 5/2004 | Litherland et al. |
| 6,736,904 B2 | 5/2004 | Poniatowski et al. |
| 6,740,107 B2 | 5/2004 | Loeb et al. |
| 6,748,944 B1 | 6/2004 | Della Vecchia et al. |
| 6,761,286 B2 | 7/2004 | Py et al. |
| 6,789,741 B2 | 9/2004 | Varanasi et al. |
| 6,814,071 B2 | 11/2004 | Klimowicz et al. |
| 6,851,626 B2 | 2/2005 | Patel et al. |
| 6,854,662 B2 | 2/2005 | Chen |
| 6,863,224 B2 | 3/2005 | Terada et al. |
| 6,885,818 B2 | 4/2005 | Goldstein |
| 6,887,642 B2 | 4/2005 | Maddox et al. |
| 6,901,926 B2 | 6/2005 | Yamamoto et al. |
| 6,913,205 B2 | 7/2005 | Cornet et al. |
| 6,921,020 B2 | 7/2005 | Ivri |
| 6,926,208 B2 | 8/2005 | Ivri |
| 6,946,117 B1 | 9/2005 | Schutt et al. |
| 6,964,647 B1 | 11/2005 | Babaev |
| 6,969,165 B2 | 11/2005 | Olsen |
| 6,974,450 B2 | 12/2005 | Weber et al. |
| 6,976,279 B1 | 12/2005 | Berke et al. |
| 6,976,969 B2 | 12/2005 | Messerly |
| 6,978,945 B2 | 12/2005 | Wong et al. |
| 7,017,573 B1 | 3/2006 | Rasor et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,081,757 B2 | 7/2006 | Unsworth et al. |
| 7,083,112 B2 | 8/2006 | Ivri |
| 7,104,463 B2 | 9/2006 | Litherland et al. |
| 7,108,197 B2 | 9/2006 | Ivri |
| 7,121,275 B2 | 10/2006 | Noolandi et al. |
| D533,658 S | 12/2006 | Collins, Jr. et al. |
| 7,153,315 B2 | 12/2006 | Miller |
| 7,161,269 B2 | 1/2007 | Kayama et al. |
| 7,168,633 B2 | 1/2007 | Wang et al. |
| D537,160 S | 2/2007 | Lowell |
| 7,174,888 B2 | 2/2007 | Ivri et al. |
| 7,192,129 B2 | 3/2007 | Droege et al. |
| 7,201,732 B2 | 4/2007 | Anderson et al. |
| 7,204,820 B2 | 4/2007 | Akahoshi |
| 7,229,028 B2 | 6/2007 | Chen et al. |
| 7,234,460 B2 | 6/2007 | Greenleaf et al. |
| 7,314,187 B2 | 1/2008 | Hochrainer et al. |
| 7,316,067 B2 | 1/2008 | Blakey |
| 7,331,339 B2 | 2/2008 | Smith et al. |
| 7,357,133 B2 | 4/2008 | Goodchild |
| 7,472,701 B2 | 1/2009 | Pfichner et al. |
| D597,206 S | 7/2009 | Collins, Jr. et al. |
| 7,574,787 B2 | 8/2009 | Xu et al. |
| 7,678,089 B2 | 3/2010 | Py et al. |
| 7,712,466 B2 | 5/2010 | Addington et al. |
| 7,819,115 B2 | 10/2010 | Sexton et al. |
| 7,883,031 B2 | 2/2011 | Collins, Jr. et al. |
| 7,954,486 B2 | 6/2011 | Papania et al. |
| 8,012,136 B2 | 9/2011 | Collins, Jr. et al. |
| 2001/0025190 A1 | 9/2001 | Weber et al. |
| 2001/0049608 A1 | 12/2001 | Hochman |
| 2001/0056258 A1 | 12/2001 | Evans |
| 2002/0016576 A1 | 2/2002 | Lee |
| 2002/0039502 A1 | 4/2002 | Matsumoto et al. |
| 2002/0043262 A1 | 4/2002 | Langford et al. |
| 2002/0073989 A1 | 6/2002 | Hadimioglu |
| 2002/0074362 A1 | 6/2002 | Py et al. |
| 2002/0107492 A1 | 8/2002 | Brach et al. |
| 2002/0121285 A1 | 9/2002 | Poniatowski et al. |
| 2002/0124843 A1 | 9/2002 | Skiba et al. |
| 2002/0161344 A1 | 10/2002 | Peclat et al. |
| 2003/0024526 A1 | 2/2003 | Ganan-Calvo |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0039355 A1 | 2/2004 | Gonzalez et al. |
| 2004/0045547 A1 | 3/2004 | Yamamoto et al. |
| 2004/0050953 A1 | 3/2004 | Terada et al. |
| 2004/0082884 A1 | 4/2004 | Pal et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0204674 A1 | 10/2004 | Anderson et al. |
| 2004/0256487 A1 | 12/2004 | Collins, Jr. et al. |
| 2005/0001981 A1 | 1/2005 | Anderson et al. |
| 2005/0029307 A1 | 2/2005 | Py et al. |
| 2005/0077315 A1 | 4/2005 | Pavlu et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0199236 A1 | 9/2005 | Fink et al. |
| 2005/0240162 A1 | 10/2005 | Chen et al. |
| 2005/0244339 A1 | 11/2005 | Jauernig et al. |
| 2005/0261641 A1 | 11/2005 | Warchol et al. |
| 2005/0263608 A1 | 12/2005 | Ivri |
| 2005/0275310 A1 | 12/2005 | Ripoll |
| 2005/0279350 A1 | 12/2005 | Rasor et al. |
| 2006/0024374 A1 | 2/2006 | Gasco et al. |
| 2006/0039715 A1* | 2/2006 | Rimai ............... G03G 15/657 399/91 |
| 2006/0057216 A1 | 3/2006 | Salamone et al. |
| 2006/0174869 A1 | 8/2006 | Gumaste et al. |
| 2006/0196518 A1 | 9/2006 | Hon |
| 2006/0201501 A1 | 9/2006 | Morrison et al. |
| 2006/0209129 A1 | 9/2006 | Onozawa |
| 2006/0213503 A1 | 9/2006 | Borgschulte et al. |
| 2006/0219806 A1 | 10/2006 | Wang et al. |
| 2006/0243820 A1 | 11/2006 | Ng |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0113841 A1 | 5/2007 | Fuchs |
| 2007/0119968 A1 | 5/2007 | Collins, Jr. et al. |
| 2007/0119969 A1* | 5/2007 | Collins, Jr. ......... A61M 11/065 239/102.1 |
| 2007/0211212 A1 | 9/2007 | Bennwik |
| 2008/0017189 A1 | 1/2008 | Ruckdeschel et al. |
| 2008/0097359 A1 | 4/2008 | Hochrainer et al. |
| 2008/0142624 A1 | 6/2008 | Ivri et al. |
| 2008/0164339 A1 | 7/2008 | Duru |
| 2008/0233053 A1 | 9/2008 | Gross et al. |
| 2008/0299049 A1 | 12/2008 | Stangl |
| 2008/0303850 A1 | 12/2008 | Shin et al. |
| 2008/0308096 A1 | 12/2008 | Borgschulte et al. |
| 2009/0025713 A1 | 1/2009 | Keller et al. |
| 2009/0114218 A1* | 5/2009 | Veatch ............... A61M 15/02 128/202.25 |
| 2009/0114742 A1 | 5/2009 | Collins, Jr. |
| 2009/0149829 A1 | 6/2009 | Collins, Jr. |
| 2009/0167812 A1 | 7/2009 | Asai et al. |
| 2009/0192443 A1 | 7/2009 | Collins, Jr. |
| 2009/0212133 A1 | 8/2009 | Collins, Jr. |

(56) References Cited

U.S. PATENT DOCUMENTS

| | | | |
|---|---|---|---|
| 2009/0272818 A1* | 11/2009 | Valpey, III | B05B 17/0646 239/102.2 |
| 2010/0044460 A1 | 2/2010 | Sauzade | |
| 2010/0211408 A1 | 8/2010 | Park et al. | |
| 2010/0222752 A1 | 9/2010 | Collins, Jr. et al. | |
| 2010/0283601 A1 | 11/2010 | Tai et al. | |

FOREIGN PATENT DOCUMENTS

| | | |
|---|---|---|
| DE | 199 34 582 A1 | 1/2001 |
| EP | 0 011 269 A1 | 5/1980 |
| EP | 0 150 571 A1 | 8/1985 |
| EP | 0 224 352 A1 | 6/1987 |
| EP | 0 389 665 A1 | 10/1990 |
| EP | 0 590 165 A1 | 4/1994 |
| EP | 0 823 246 A2 | 2/1996 |
| EP | 0 933 138 A2 | 8/1999 |
| EP | 1 493 410 A2 | 1/2005 |
| FR | 1 271 341 | 7/1961 |
| GB | 558866 | 7/1942 |
| GB | 1 569 707 | 7/1980 |
| JP | 8-52193 | 2/1996 |
| JP | 2000-043243 | 2/2000 |
| JP | 3104861 U | 8/2004 |
| JP | 2005-288009 | 10/2005 |
| JP | 2009-072313 | 4/2009 |
| TW | I 293898 | 7/1994 |
| WO | WO 85/00761 A1 | 2/1985 |
| WO | WO 91/12687 A1 | 8/1991 |
| WO | WO 91/14468 A1 | 10/1991 |
| WO | WO 94/13305 A1 | 6/1994 |
| WO | WO 94/23788 A1 | 10/1994 |
| WO | WO 97/05960 A1 | 2/1997 |
| WO | WO 97/12687 A1 | 4/1997 |
| WO | WO 97/23177 | 7/1997 |
| WO | WO 98/19383 A1 | 5/1998 |
| WO | WO 99/17888 A1 | 4/1999 |
| WO | WO 00/18455 A1 | 4/2000 |
| WO | WO 00/66277 A1 | 11/2000 |
| WO | WO 01/03645 A2 | 1/2001 |
| WO | WO 01/19437 A1 | 3/2001 |
| WO | WO 01/58236 A2 | 8/2001 |
| WO | WO 01/85245 A1 | 11/2001 |
| WO | WO 02/28545 A1 | 4/2002 |
| WO | WO 02/055131 A2 | 7/2002 |
| WO | WO 01/062488 A1 | 8/2002 |
| WO | WO 02/072169 A2 | 9/2002 |
| WO | WO 03/002045 A1 | 1/2003 |
| WO | WO 03/002265 A1 | 1/2003 |
| WO | WO 03/026556 A2 | 4/2003 |
| WO | WO 03/097139 A1 | 11/2003 |
| WO | WO 2004/028420 A1 | 4/2004 |
| WO | WO 2004/050065 A1 | 6/2004 |
| WO | WO 2004/103478 A1 | 12/2004 |
| WO | WO 2004/105864 A1 | 12/2004 |
| WO | WO 2006/006963 A2 | 1/2006 |
| WO | WO 2006/082588 A2 | 8/2006 |
| WO | WO 2008/015394 A1 | 2/2008 |
| WO | WO 2009/148345 A2 | 12/2009 |
| WO | WO 2012/009696 A2 | 1/2012 |
| WO | WO 2012/009702 A1 | 1/2012 |

OTHER PUBLICATIONS

Conover (Ed.), "View into the Guture of Ophthalmology Treatments," *Healthcare Observer*, 1(8):2-37 (2009).

Dhand, "Nebulizers That Use a Vibrating Mesh or Plate with Multiple Apertures to Generate Areosol," *Respir Care*, 47(12):1406-1418 (2002).

Donnelly et al., "Using ultrasonic atomization to produce an aerosol of micron-scale particles," *Review of Scientific Instruments*, 76:113310-1-113301-10 (2005).

Durnan et al., "Gold-Chlorine and Gold-Bromine Equilibria in Fused Salts," *The Journal of Physical Chemistry*, 68(4):847-850 (1964).

Galambos et al., "Drop ejection utilizing sideways actuation of a MEMS piston," *Sensors and Actuators A*. 141:182-191 (2008).

Hinds, *Aerosol Technology: Properties, Behavior, and Measurement of Airborne Particles*, pp. 42-71, 111-119, & 294-301 (1999).

Instruction Manual for Omron® Model NE-U03V MicroAir® Nebulizer, 20 pages (No date).

International Search Report dated Dec. 12, 2011, in International Application No. PCT/US2011/044291.

International Search Reprot dated Dec. 13, 2011, in International Application No. PCT/US2011/044286.

Product Description for Xalatan®: Iatanoprost ophthalmic solution, Pfizer Manufacturing, Belgium, NV, 8 pages (2009).

Quigley, "Improving Eye Drop Treatment for Glaucoma through Better Adherence," *Optometry and Vision Science*, 85(6):374-375 (2008).

Ranade et al., "Chapter seven: Intranasal and ocular drug delivery," *Drug Delivery Systems: Second Edition*, CLC Press, 39 pages (2004).

Rosen et al., "Printing High Viscosity Fluids Using Ultrasonic Droplet Generation," The George W. Woodruff School of Mechanical Engineering, Georgia Institute of Technology, pp. 239-253 (2008).

Shidhaye et al., "Novel drug delivery devices," *Pharma Times*, 38(7):24-27 (2006).

Tamilvanan et al., "The potential of lipid emulsion for ocular delivery of lipophilic drugs," *European Journal of Pharmaceutics and Biopharmaceutics*, 58:357-368 (2004).

Xia et al., "A potential application of a piezoelectric atomiser for ophthalmic drug delivery," *BOB*, 4(1):9-17 (2007).

Yee et al., "Trends in Glaucoma Treatment," EyeWorld Educational Symposium, San Francisco, 8 pages (2006).

Yuan et al., "MEMS-based piezoelectric array microjet," *Microelectronic Engineering*, 66:767-772 (2003).

* cited by examiner

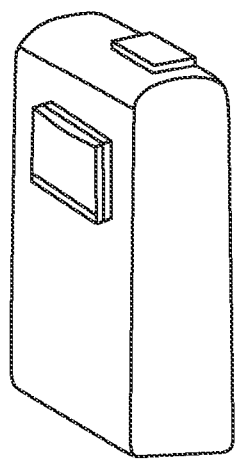 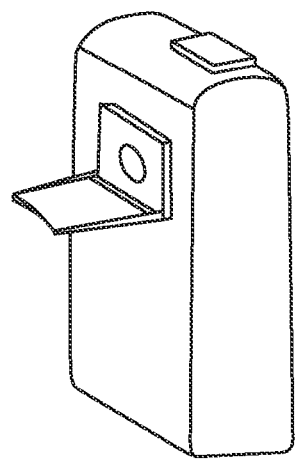
FIG. 14A  FIG. 14B
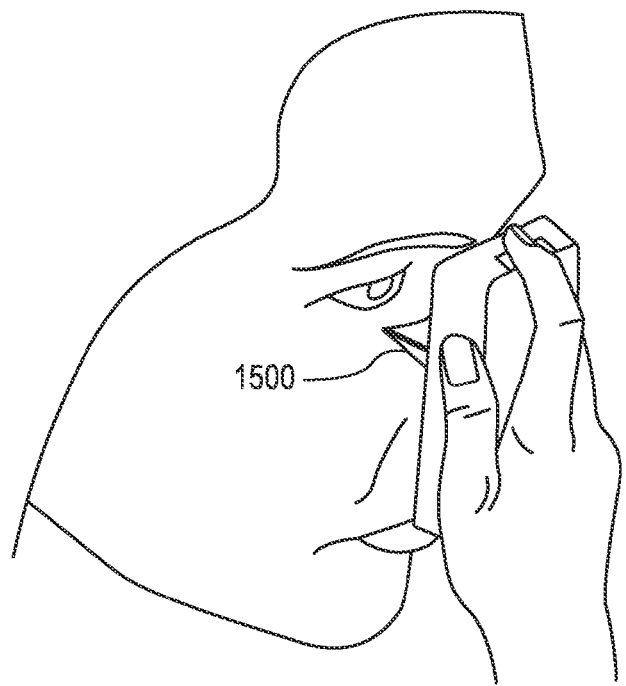
FIG. 15A

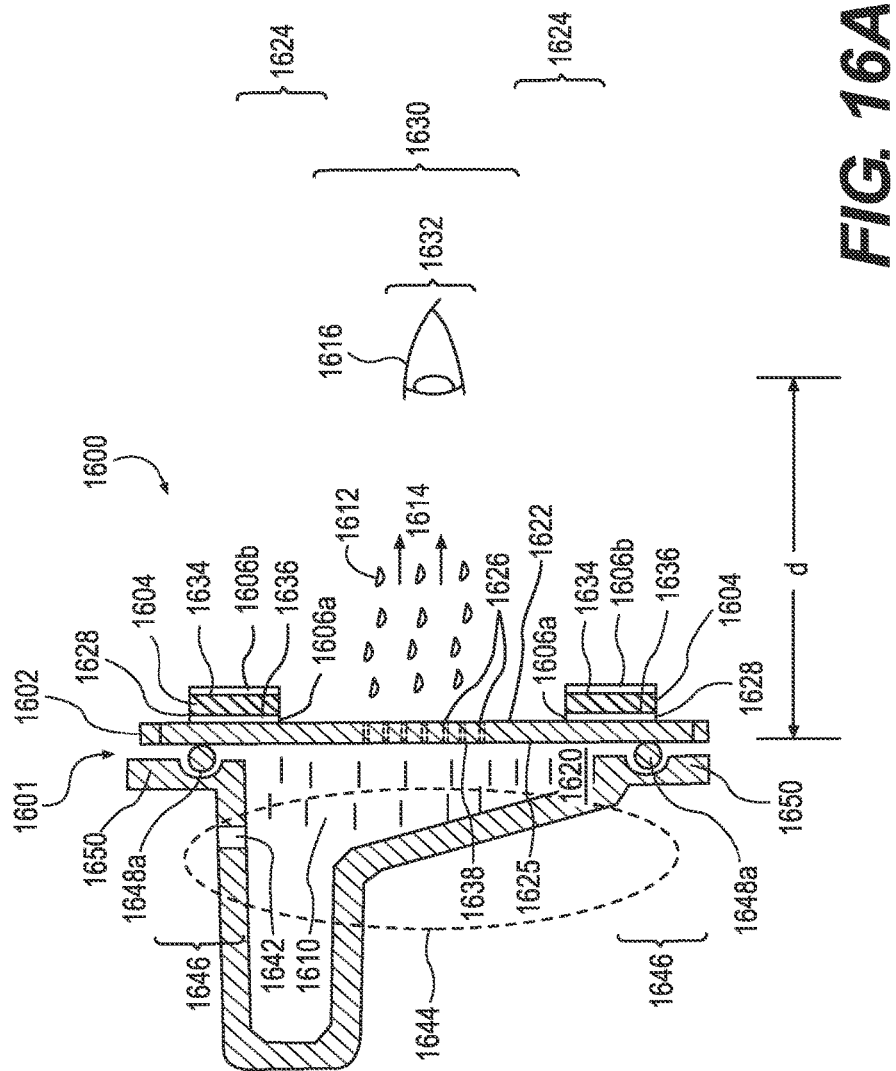

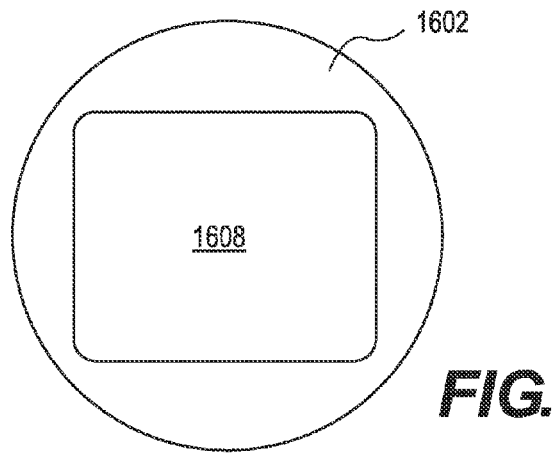
FIG. 16D
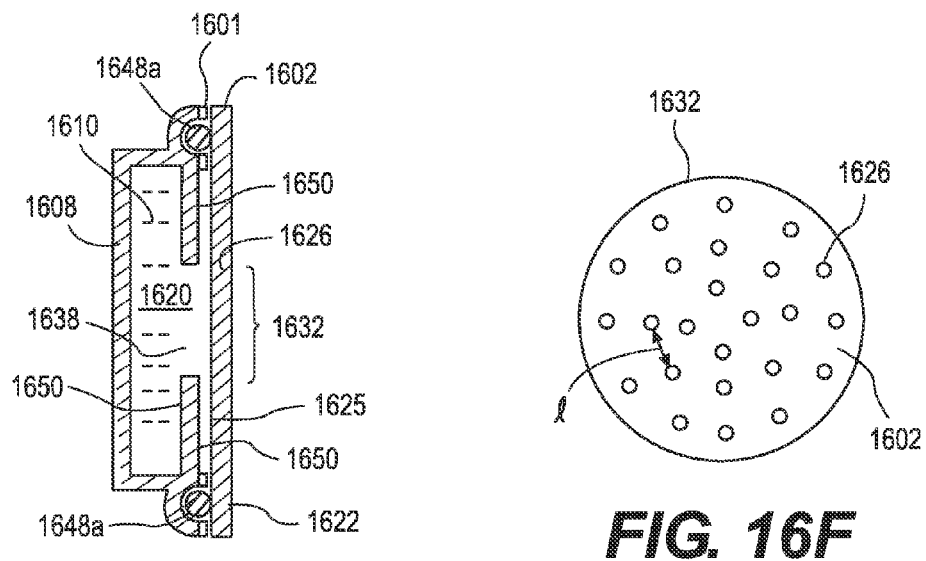
FIG. 16E
FIG. 16F
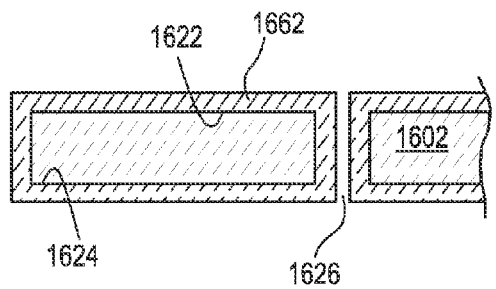
FIG. 16G

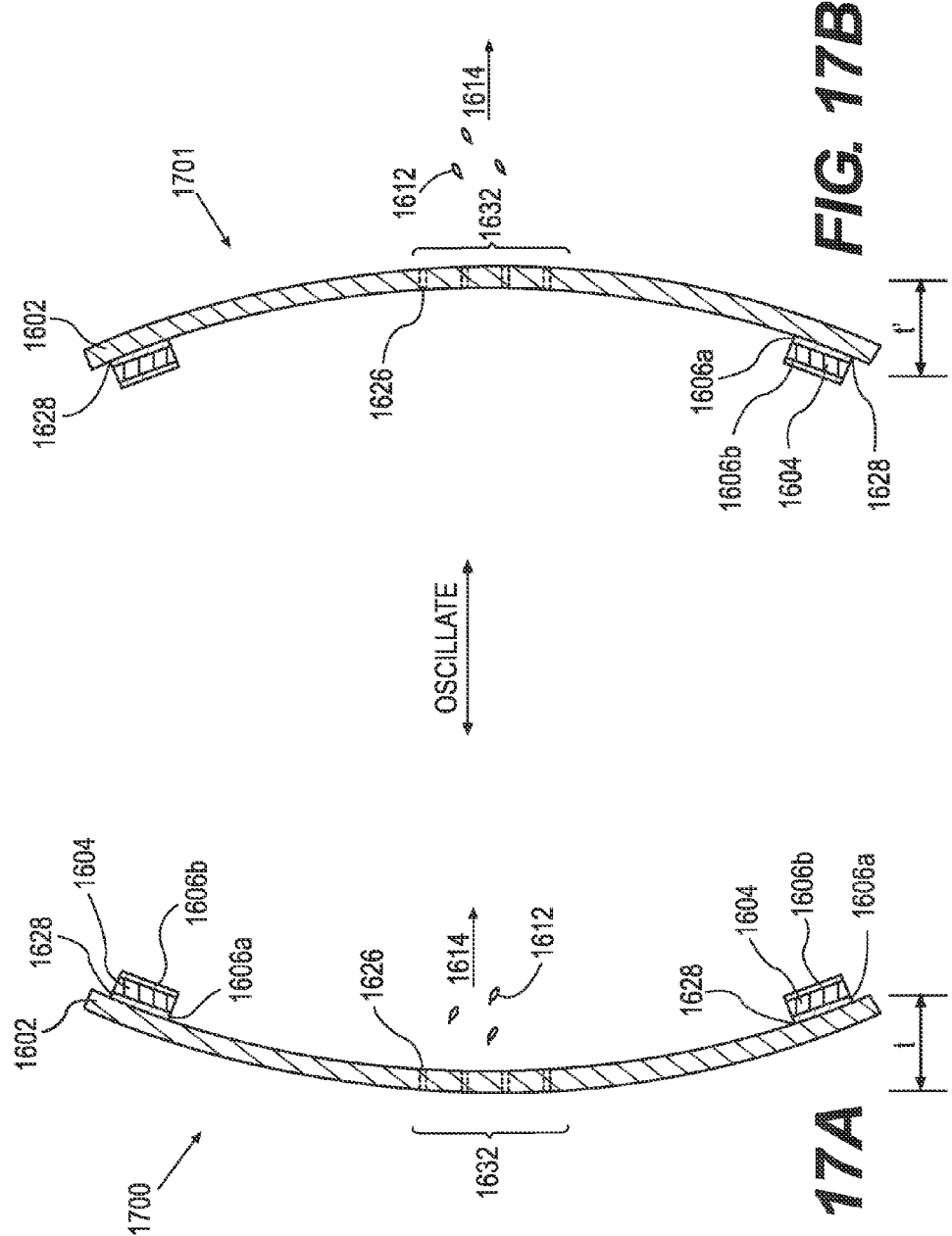

Average Droplet: 11 um

Average Droplet: 17 um

Average Droplet: 32 um

Average Droplet: 56 um

Average Droplet: 100 um

Mesh size: 60 um

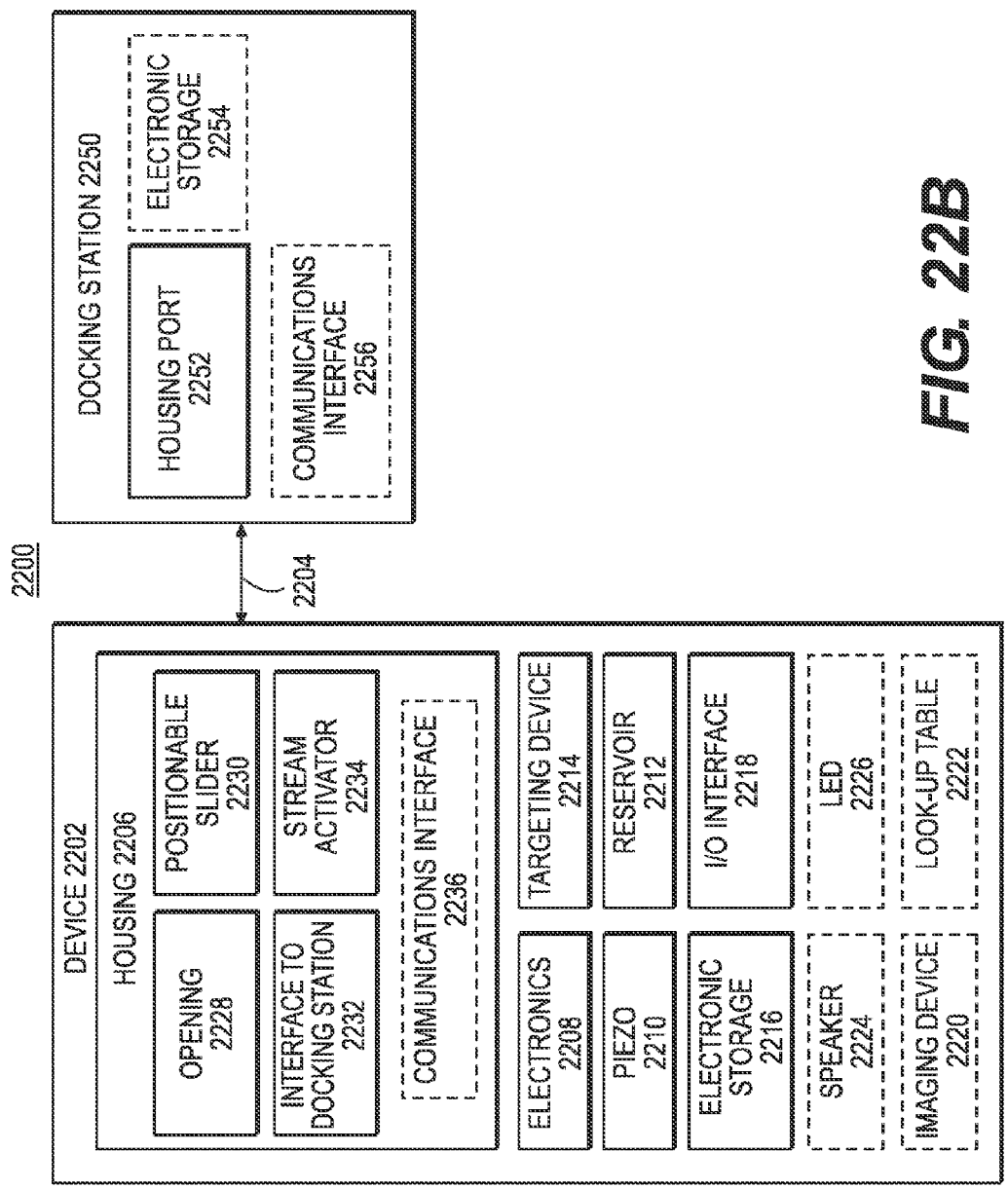

METHODS TO LIGHT THE SURFACE OF EJECTOR
FIBER OPTIC CORD
(WITH ETCHED SURFACE)
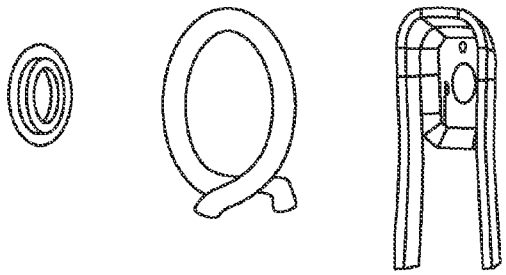
SINGLE OR MULTIPLE
SURFACE MOUNTED LED(S)
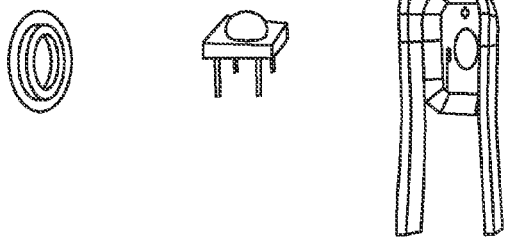
LED RING
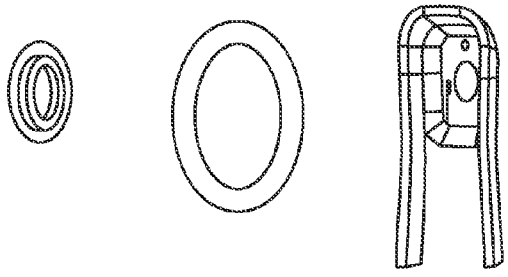
BIAS CUT FIBER OPTIC
CORD (WITH REFLECTIVE
LINNING)
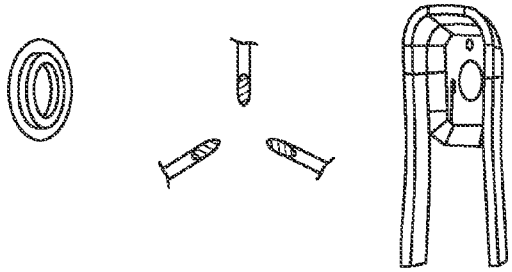
*FIG. 26*

FIG. 27. Ratio of nozzle velocity to terminal velocity as a function of droplet diameter.

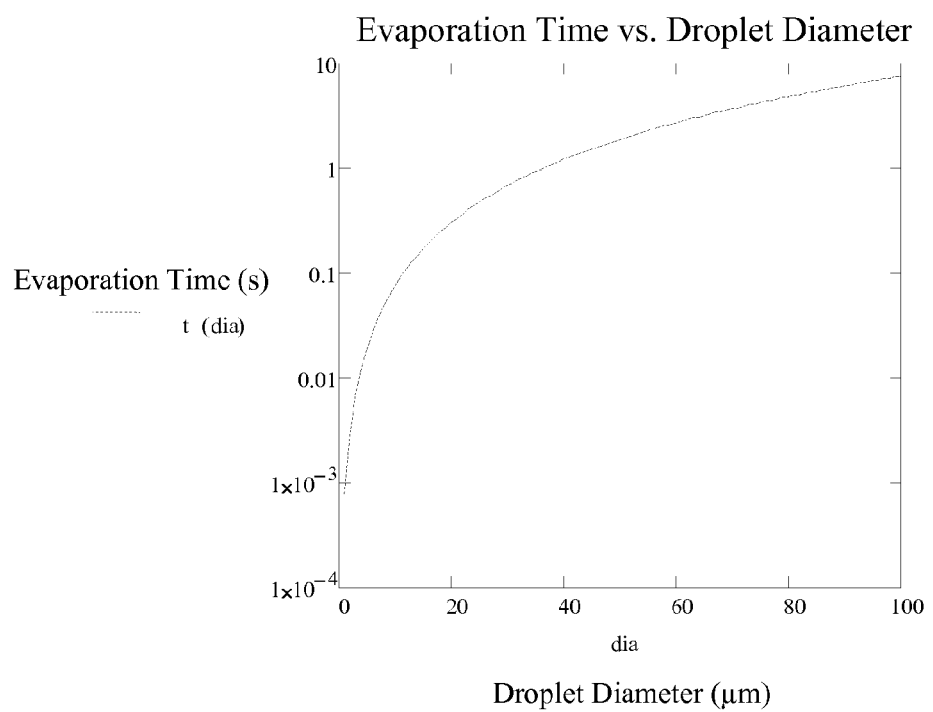
FIG. 28. Evaporation time as a function of droplet diameter for water at NTP.

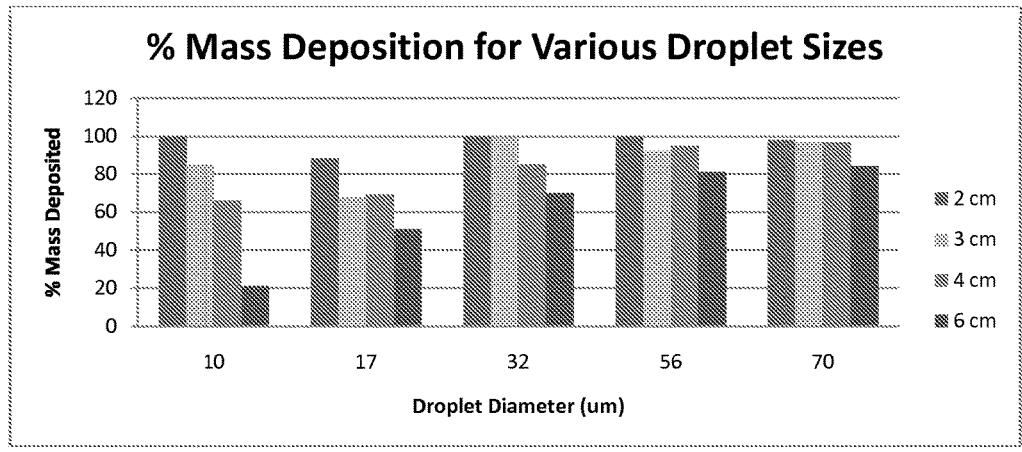
FIG. 29A. % mass deposition as a function of droplet diameter and distance from the ejector plate.
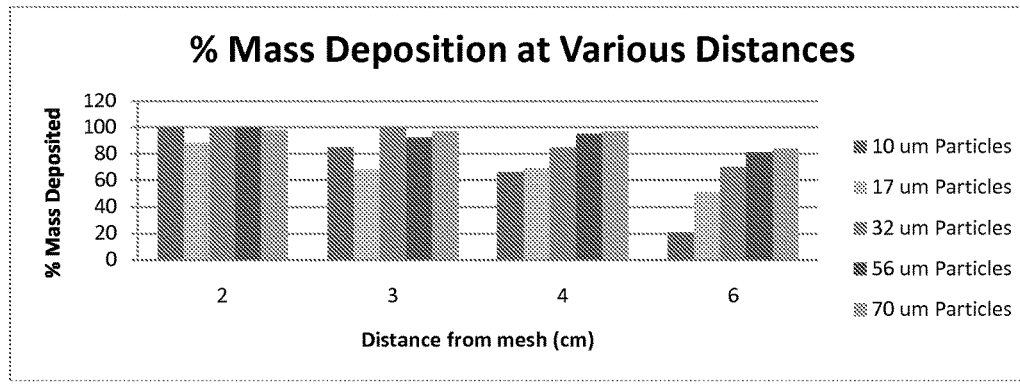
FIG. 29B. % mass deposition as a function of distance from the ejector plate and droplet diameter.

DROP GENERATING DEVICE

RELATED APPLICATIONS

The present application claims the benefit of the filing date of U.S. Provisional Application No. 61/400,864, filed Jul. 15, 2010, U.S. Provisional Application No. 61/401,850, filed Aug. 20, 2010, U.S. Provisional Application No. 61/401,920 filed Aug. 20, 2010, U.S. Provisional Application No. 61/401,918 filed Aug. 20, 2010, U.S. Provisional Application No. 61/401,848 filed Aug. 20, 2010, U.S. Provisional Application No. 61/401,849 filed Aug. 20, 2010, U.S. Provisional Application No. 61/462,576 filed Feb. 4, 2011, U.S. Provisional Application No. 61/462,791 filed Feb. 5, 2011, U.S. Provisional Application No. 61/463,280 filed Feb. 15, 2011, U.S. Provisional Application No. 61/516,462, filed Apr. 4, 2011, U.S. Provisional Application No. 61/516,496 filed Apr. 4, 2011, U.S. Provisional Application No. 61/516,495 filed Apr. 4, 2011, and U.S. Provisional Application No. 61/516,694, filed Apr. 6, 2011, the entire contents of each of which is specifically hereby incorporated by reference for all purposes. The present application is also related to U.S. Provisional Application No. 61/396,531 filed May 28, 2010, the entire contents of which is specifically hereby incorporated by reference for all purposes.

BACKGROUND OF THE INVENTION

Using spray dispensers to administer products in the form of mists or sprays is an area with large potential for safe, easy-to-use products. The major challenge in providing such an applicator is to provide consistent and accurate delivery of suitable doses.

An important area where spray applicators are needed is in delivery of eye medications. The application of fluids, as in the case of eye drops has always posed a problem, especially for children and animals who tend to blink or jerk at the critical moment, causing the droplet to land on the eyelid, nose or other part of the face. The impact of a large drop of fluid on the eyeball, especially when the fluid is at a different temperature also tends to produce a blinking reaction. Elderly also often lose the hand coordination necessary to get the eye drops into their eyes. Stroke victims have similar difficulties. Dropper delivery often requires a particular physical position, such as tilting of the head or a horizontal position. Neither might be practical.

Often, it is critical that the subject administer the correct dose the requisite number of times per day. However, in practice, subjects that are prescribed eye medications for home use tend to forget to dose, or dose excessively or cross-dose with other medications. One of the major compliance problems is that, even if the subject is intent on following the treatment regimen, he or she often forgets to dose.

Currently, many of these medications are administered by eye droppers. Current eye drop devices often either require the head to be tilted back, the subject to lie down or provide downward traction on the lower eyelid, or a combination of traction and tilting, since the delivery mechanism typically relies on gravity for applying the medication. This is not only awkward, but involves a fair amount of coordination, flexibility and cooperation on the part of the subject to ensure that the medication gets into the eye while avoiding poking the eye with the dropper tip. Current eye dropper bottles pose the risk of poking the user in the eye, potentially causing physical damage to the eye, and further, exposing the tip to bacterial contamination due to contact with the eye. As such, the subject runs the risk of contaminating the medication in the eye drop bottle and subsequently infecting the eye. Additionally, a large volume of the medication flows out of the eye or is washed away by the tearing reflex. As a result, this method of administration is also inaccurate and wasteful. Moreover, the technology does not provide a satisfactory way of controlling the amount of medication that is dispensed, nor does it provide a way of ensuring that the medication that is dispensed actually lands on the eye and remains on the eye.

Eye droppers also provide no way of verifying compliance by a subject. Even if after a week of use the eye dropper bottle could be checked for the total volume of medication dispensed, e.g., by weighing the bottle, this does not provide a record of day-to-day compliance. A subject may have missed one or more doses and overdosed on other occasions. Also, the poor precision with which eye droppers deliver drops to the eye leaves a question mark whether the medication actually gets into the eye, even though it may have been dispensed.

Accordingly, there is a need for a delivery device that delivers safe, suitable, and repeatable dosages to a subject for ophthalmic, topical, oral, nasal, or pulmonary use.

SUMMARY OF THE INVENTION

The present invention includes a device and method of delivering safe, suitable, and repeatable dosages to a subject for ophthalmic, topical, oral, nasal, or pulmonary use. The present invention also includes a fluid delivery system capable of delivering a defined volume of the fluid in the form of droplets having properties that afford adequate and repeatable high percentage deposition upon application.

The present invention includes and provides a device for delivering a fluid to an eye of a subject, the device comprising a housing, a reservoir disposed within the housing for receiving a volume of fluid, an ejector mechanism configured to eject a stream of droplets having an average ejected droplet diameter greater than 15 microns, the stream of droplets having low entrained airflow such that the stream of droplets deposit on the eye of the subject during use.

The invention further includes and provides a device wherein the ejector mechanism comprises an ejector plate having a first surface that couples a fluid delivery area of the reservoir, the ejector plate including a plurality of openings formed through its thickness, an actuator coupled to a second surface of the ejector plate, the actuator being operable to oscillate the ejector plate at a frequency and generate a directed stream of droplets.

Yet another implementation of the invention includes and provides a device for delivering a volume of ophthalmic fluid to an eye comprising a housing, a reservoir disposed within the housing for receiving a volume of ophthalmic fluid, an ejector plate being in fluid communication with the reservoir, the ejector plate including a plurality of openings formed through its thickness, an actuator formed on a surface of the ejector plate opposite the reservoir, the actuator being operable to oscillate the ejector plate at a frequency and generate a directed stream of droplets, wherein the droplets in the directed stream have an average ejecting diameter in the range of 5-2500 microns, including but not limited to 20-100 microns, and an average initial velocity in the range of 1-100 m/s, including but not limited to, 2-20 m/s.

Yet another implementation of the invention includes and provides for a method of delivering a volume of ophthalmic fluid to an eye of a subject, the method comprising ejecting a directed stream of droplets of an ophthalmic fluid contained in a reservoir from openings of an ejector plate, the droplets in the directed stream having an average ejecting diameter in the range of 5-2500 microns, including but not limited to 20-100 microns, and an average initial velocity in the range of 1-100 m/s, including but not limited to, 2-20 m/s.

BRIEF DESCRIPTION OF THE DRAWINGS

FIGS. 14A-B show another implementation of the device including a spacer.

FIG. 15A shows another implementation of the device including a spacer.

FIG. 16A shows a schematic cross-sectional view of another implementation of the device using a piezoelectric ejector mechanism.

FIG. 16D shows a schematic back view of the assembly.

FIG. 16E shows a schematic cross-sectional view of a portion of the assembly.

FIG. 16F shows a schematic top view of an ejection region of the assembly.

FIG. 16G shows a partial cross-sectional view of the ejector plate of the assembly.

FIGS. 17A and 17B show cross-sectional views of activated ejector plates.

FIG. 22B shows a block diagram depicting a device and a docking station in communication.

FIG. 26 shows methods to light the surface of the ejector.

FIG. 27 shows the ratio of nozzle velocity to terminal velocity as a function of droplet diameter.

FIG. 28 shows evaporation time as a function of droplet diameter for water at NTP.

FIG. 29A shows the percent mass deposition as a function of droplet diameter and distance from an ejector plate of the disclosure, and FIG. 29B shows the percent mass deposition as a function of distance from an ejector plate of the disclosure and droplet diameter.

DETAILED DESCRIPTION

The present disclosure generally relates to ejection devices useful, e.g., in the delivery of fluid such as ophthalmic fluid to the eye. In certain aspects, the ejection devices include an ejection assembly which generates a controllable stream of droplets of fluid. Fluid includes without limitation, suspensions or emulsions which have viscosities in a range capable of droplet formation using an ejection mechanism.

As explained in further detail herein, in accordance with certain aspects of the present disclosure, the ejector mechanism presently disclosed may form a directed stream of droplets which may be directed toward a target. The droplets will be formed in distribution of sizes, each distribution having an average droplet size. The average droplet size may be in the range of about 15 microns to over 100 microns, greater than 20 microns to about 100 microns, about 20 microns to about 80 microns, about 25 microns to about 75 microns, about 30 microns to about 60 microns, about 35 microns to about 55 microns, etc. However, the average droplet size may be as large as 2500 microns, depending on the intended application. Further, the droplets may have an average initial velocity of about 0.5 m/s to about 100 m/s, e.g., about 0.5 m/s to about 20, e.g., 0.5 to 10 m/s, about 1 m/s to about 5 m/s, about 1 m/s to about 4 m/s, about 2 m/s, etc. As used herein, the ejecting size and the initial velocity are the size and initial velocity of the droplets when the droplets leave the ejector plate. The stream of droplets directed at a target will result in deposition of a percentage of the mass of the droplets including their composition onto the desired location.

Figure 1:
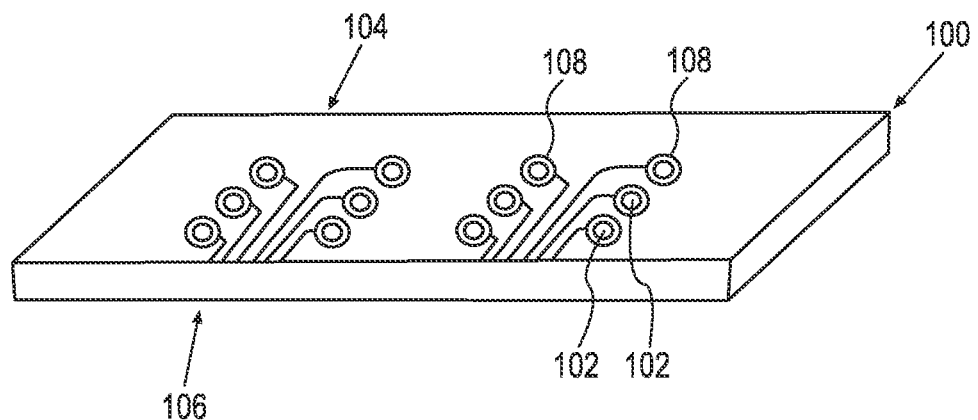
FIG. 1 shows a three-dimensional view of a depiction of a substrate structure of an ejector device.

Fluids suitable for use by the ejection device can have very low viscosities, e.g., as with water at 1 cP, or less, e.g. 0.3 cP. The fluid may additionally have viscosities in ranges up to 600 cP. More particularly, the fluid may have a viscosity range of about 0.3 to 100 cP, 0.3 to 50 cP, 0.3 to 30 cP, 1 cP to 53 cP, etc. In some implementations, solutions or medications having the suitable viscosities and surface tensions can be directly used in the reservoir without modification. In other implementations, additional materials may be added to adjust the fluid parameter.

The disclosed technology includes ejected droplets without substantial evaporation, entrainment of air, or deflection off of the eye surface, which facilitates consistent dosing. Average ejecting droplet size and average initial velocity are dependent on factors including fluid viscosity, surface tension, ejector plate properties, geometry, and dimensions, as well as operating parameters of the ejector mechanism including its drive frequency. In some implementations, about 60% to about 100%, about 65% to about 100%, about 75% to about 100%, about 80% to about 100%, about 85 to about 100%, about 90% to about 100%, about 95% to about 100%, etc., of the ejected mass of droplets are deposited on the surface of the eye, such deposition being repeatable. The direction of flow of the stream of droplets may be horizontal, or any direction a user chooses to aim the actuation mechanism during use.

Without wishing to be bound by this theory, it is believed that as droplet diameter decreases, the ratio of the total surface area to total volume increases. That is, more surface area is exposed for a given total volume of fluid. Therefore, smaller droplets may create a larger surface area which creates more drag. In the low Reynolds number regime (Re<1), the drag force is given by Stoke's law, a solution to the Navier-Stokes equations. Thus, the drag force is believed to be proportional to the square root of the surface area of a droplet. Presuming that the droplet is spherical, the drag force is believed to be proportion to the diameter of the droplet.

Each particle carries air along with it (entrained air), creating an airstream. This effect of this entrained air stream is believed to be approximately proportional to diameter. When the airstream reaches a target, it may deflect or sharply turn, say by 90 degrees adjacent to the surface of the target to maintain flow. If the flow of the airstream is too large, it may carry some of the droplets with it, causing them to deflect and not deposit on the surface of the target. Particles with sufficiently large momentum will overcome this effect and successfully deposit on the surface. The stopping distance is an approximation of the distance the particle will travel before the initial momentum is diminished to zero by air friction. Entrained air created by surrounding particles will increase the stopping distance, giving each droplet a larger possible range and more opportunity for deflection. Droplets also fall vertically during their flight path due to gravity. After a short acceleration time, droplets reach their terminal velocity where the drag force is equal and opposite to the gravitational force. Larger particles fall faster because terminal velocity is proportional to their surface area. The droplet lifetime also depends on the local and ambient partial pressures, the local and ambient temperatures, and the particle diameter, all of which affect its rate of evaporation. Generally, larger particles will evaporate slower.

Again not limited by any particular theory, droplets are formed by an actuation mechanism that forms the stream of droplets from fluid contained in a reservoir coupled to the ejector mechanism. The ejector mechanism and reservoir may be disposable or reusable. They may be packaged in a housing. The housing may be disposable or reusable. The housing may be handheld, miniaturized, formed to couple to a base, and may be adapted for communication with other devices. Housings may be color-coded or configured for easy identification. Droplet ejector devices, in some implementations, may include illumination means, alignment means, temperature control means, diagnostic means, or other features. Other implementations may be part of a larger network of interconnected and interacting devices used for subject care and treatment. The ejector in one implementation may be a thermal ejector. In another, it may be an ultrasonic ejector. In yet another implementation, the ejector may be a piezoelectric ejector.

Figure 18A:
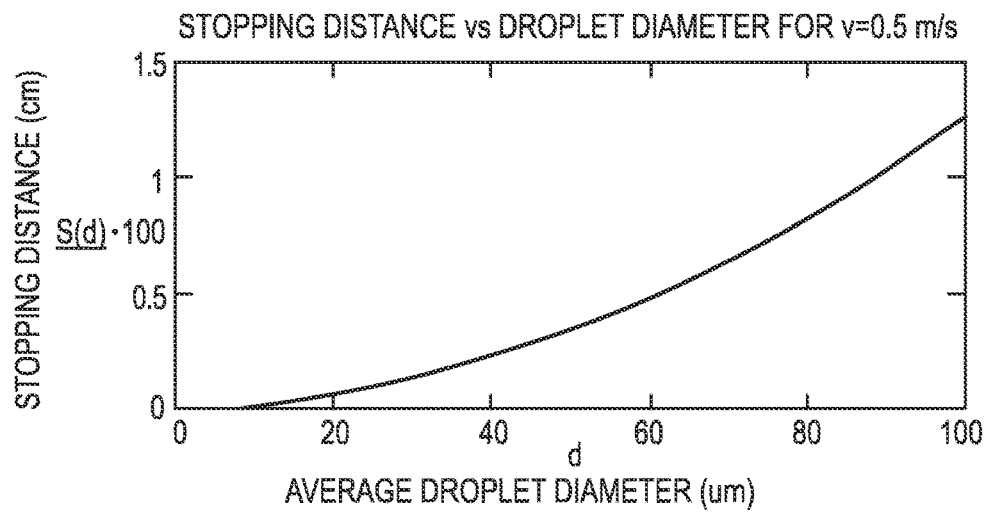
FIGS. 18A-C show plots of droplet stopping distance versus average droplet diameter.
Figure 18B:
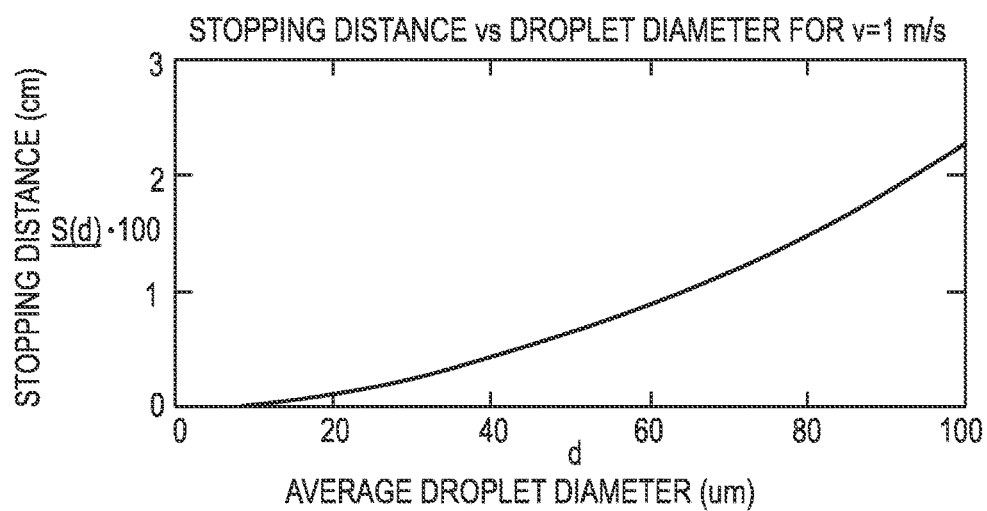
Figure 18C:
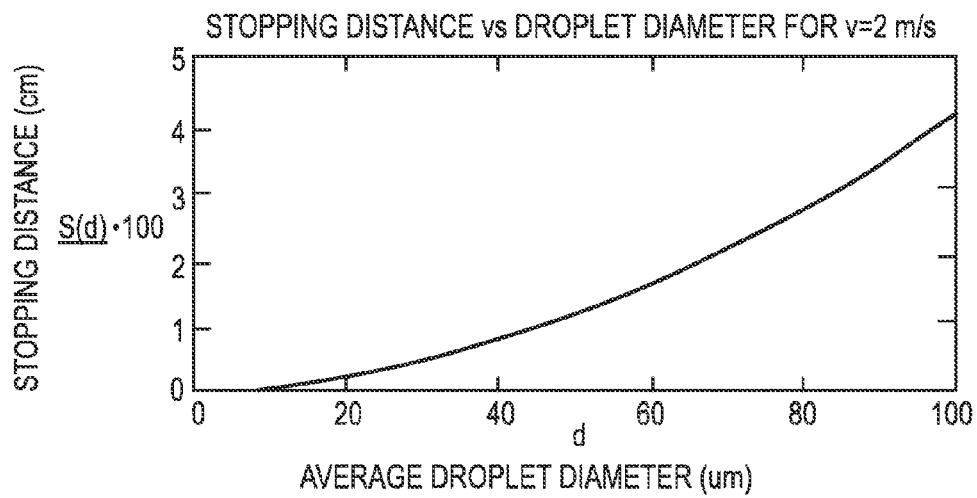
Figure 19:
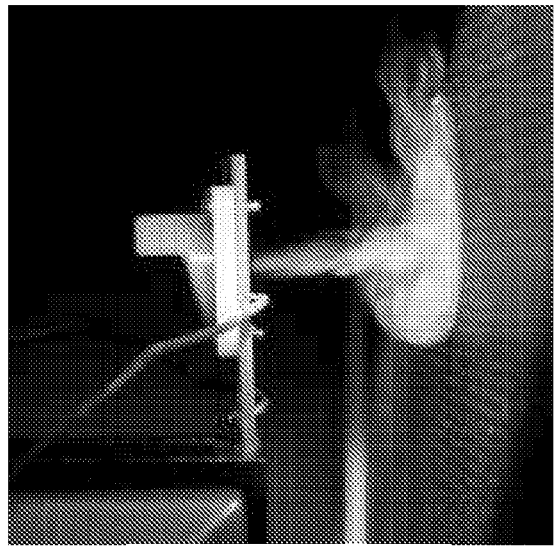
FIGS. 19A-F depict directed streams of droplets of different average size.
Figure 19:
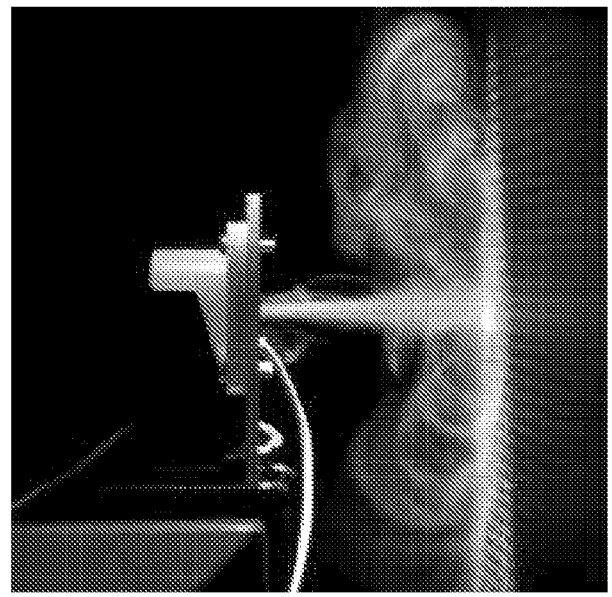
Figure 19:
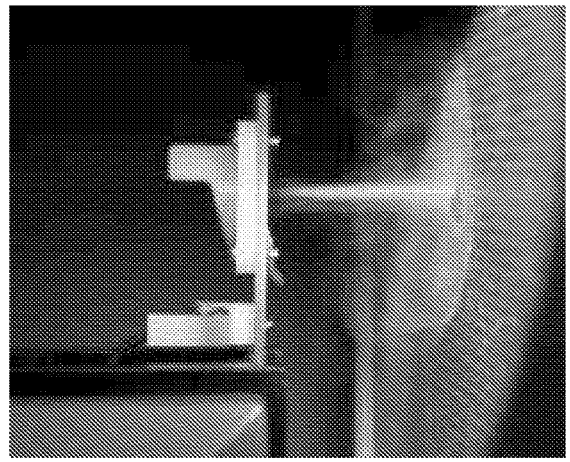
Figure 19:
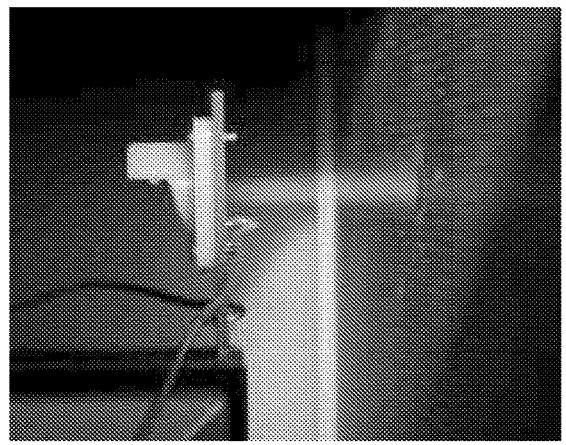
Figure 19:
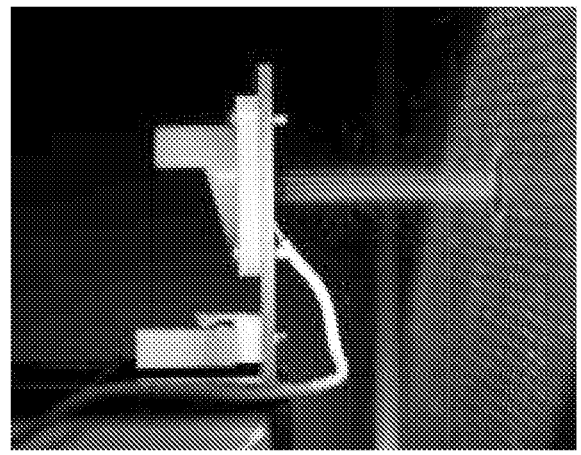
Figure 19:
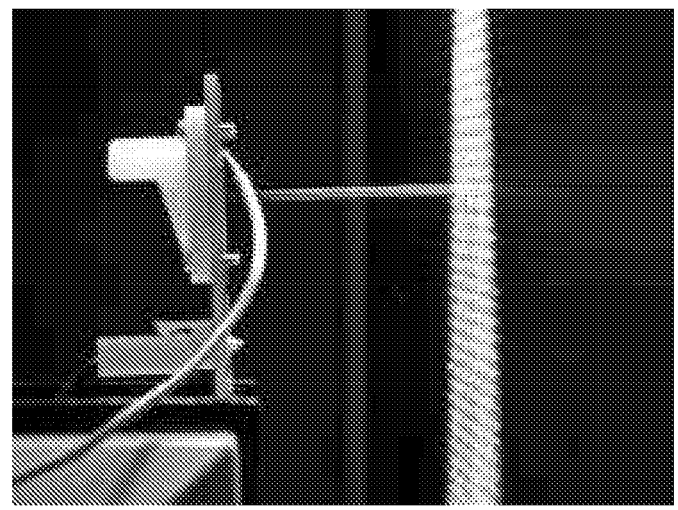
Figure 20:
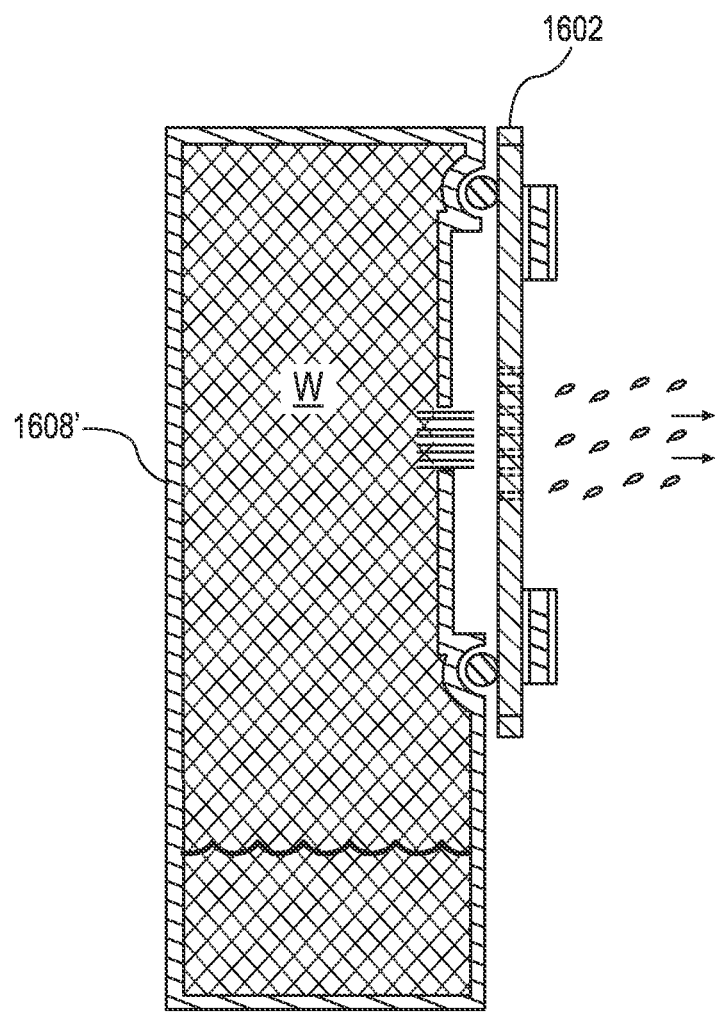
FIG. 20 shows a perspective view of a portion of the assembly, including an alternative implementation of the reservoir.

FIGS. 18A-C shows the stopping distances in still air of the droplet having different droplet diameters and at ejecting velocities of 0.5 m/s, 1 m/s, and 2 m/s, respectively. In particular, referring to FIG. 18A, in this implementation, the longest stopping distance of a droplet having an ejecting diameter of 100 microns or smaller and an initial velocity of 0.5 m/s is about 1.25 cm. Accordingly, in this implementation, without assistance from an airflow, these droplets cannot be effectively deposited into an eye located more than 1.25 cm away from the ejector plate 102. Referring to FIG. 18B, the longest stopping distance of a droplet having an ejecting diameter of 100 microns or smaller and an ejecting velocity of 1 m/s is about 2.2 cm. Accordingly, in this aspect, without assistance from an airflow, these droplets cannot be effectively deposited into an eye located more than 2.2 cm away from the ejector plate 1902 (FIG. 19A). Referring to FIG. 18C, the longest stopping distance of a droplet having an ejecting diameter of 100 microns or smaller and an ejecting velocity of 2 m/s is about 4 cm. Accordingly, without assistance from an airflow, these droplets cannot be effectively deposited into an eye located more than 4 cm away from the ejector mechanism. The stopping distances of fluids containing ingredients other than water may be different from those shown in FIGS. 18A-C.

Figure 18D:
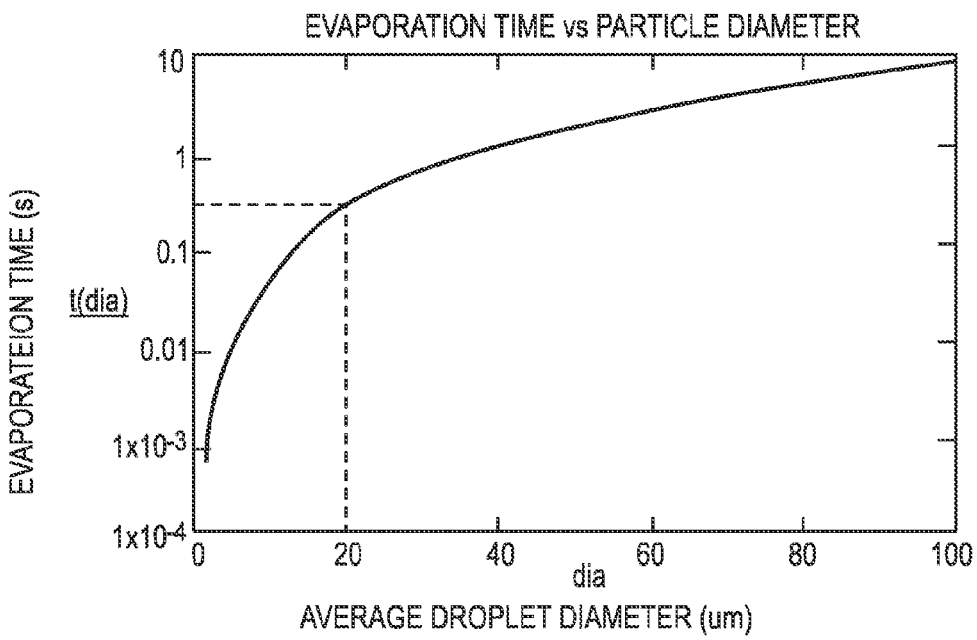
FIG. 18D shows a plot of droplet evaporation time versus average droplet diameter.

Before reaching the target, the ejected droplets may evaporate in the air. Delivering droplets having an ejecting velocity of about 1 m/s to about 5 m/s to a target located about 3 cm from the ejector mechanism may take about 0.03 s or less to reach the surface of the target. Without wishing to be bound by this theory, it is believed that the rate of evaporation is related to the diameter of the droplets and the environmental parameters including temperature and humidity. It is also believed that a long evaporation time, e.g., longer than the delivery time of about 0.03 s, is desired for effectively depositing the droplets. Assuming that the temperature is 20° C. and the fluid is water, FIG. 18D shows that the a droplet having a diameter of about 40 microns completely evaporates in about 1 s, and a droplet having a diameter of about 100 microns completely evaporates in about 10 s. In some implementations, saline or other additives can be added into the fluid to reduce the evaporation rate.

FIGS. 19A-F show deflection of the droplets and entrained airstream against a target. Droplets without sufficient momentum to counterbalance the forces from this stream are carried by it and are similarly deflected. Nevertheless, those droplets having a sufficient momentum, either due to high velocity or high mass or both, do continue on their own trajectory and are not carried away by the airstream. These droplets can be effectively delivered to the target. Sufficient momentum can be achieved from a large initial ejecting velocity and a momentum to drag ratio. Velocity, however, must not create discomfort when the droplets impact the target, should the target be for human or animal use, and should not be such as to adversely affect other parameters such as drag. Alternatively, sufficient momentum can be achieved by an increase in the mass of the droplet.

Referring to FIGS. 19A-F, in this implementation, water droplets 1912 having different average ejecting diameters are ejected at an ejecting velocity of 4 m/s from an ejector plate 1902 horizontally towards a surface 1916 located 3 cm away from the ejector plate 1902. The surface 1916 can be a glass surface that has features, e.g., smoothness, similar to an eye surface. Other than the diameter of the openings (e.g., like the openings 1626 of FIG. 16A) in the ejector plate 1902, all other parameters, are kept the same in all of FIGS. 19A-F.

Referring to FIG. 19A, in that implementation, the ejected droplets 1912 have an average ejecting diameter of about 11 microns. The stream 1014*a* of the droplets 1912 has a varying cross-sectional area, indicating that some of the droplets 1912 may have stopped before reaching the surface 1916. Furthermore, a substantial amount 1918*a* of droplets 1912 reaching the surface 1916 is carried away by air along the surface 1916 without being deposited onto the surface.

Referring to FIG. 19B, in this implementation, the ejected droplets have an average ejecting diameter of about 17 microns. The stream 1914*b* of the droplets 1912 also has a varying cross-sectional area (like the stream 1914*a*), indicating that some of the droplets may have stopped before reaching the surface 1916. However, the cross-sectional area variation of the stream 1914*b* is smaller than the variation of the stream 1914*a*. As a result, more droplets 1912 in the stream 1914*b* reach the surface 1916 than in the stream 1914*a*. However, a substantial amount 1918*b* of droplets 1912 reaching the surface 1916 is carried away by air along the surface 1916 without being deposited onto the surface 1916. The amount 1918*b* is larger than the amount 418*a* so that although a larger amount of droplets 1912 reach the surface 1916, the deposited amount on the surface 1916 does not increase substantially compared to FIG. 19A.

Referring to FIG. 19C, the ejected droplets have an average ejecting diameter of about 32 microns. The stream 1914*c* of the droplets 1912 has a cross-sectional area that varies substantially less than those of the streams 1914*a*, 1914*b*, indicating very few droplets may have stopped before reaching the surface 1916. Furthermore, an amount 1918*c* of droplets 1912 reaching the surface 1916 and carried away by air along the surface 1916 without being deposited onto the surface 1916 is smaller than the amounts 1918*a*, 1918*b*.

Referring to FIGS. 19D-19E, in this implementation, the ejected droplets have average diameters of about 56 microns, 100 microns, respectively. FIG. 19F shows ejection of large droplets. The streams 1914*d*, 1914*e*, 1914*f* of the droplets 1912 have substantially constant cross-sectional area, indicating that substantially no droplets have stopped before reaching the surface 1916. Furthermore, substantially no droplets 1912 reaching the surface 1916 are carried away along the surface 1916 without being deposited onto the surface.

In summary, the calculations in FIGS. 18A-D and the photographs in FIGS. 19A-F suggest that airstream can have undesirable effect of carrying droplets across the target surface by movement of the entrained airstream and thereby prevent them from depositing on the target. Furthermore, this undesirable effect is most pronounced for smaller droplets. Without wishing to be bound by this theory, it is believed that this problem occurs with small droplets for a number of reasons more fully described below.

Additionally, charging the droplets may improve their ability to reach the target. The human body, and especially the moist eye surface, is a conductor, therefore it may attract the charged droplets aiding in their contact with the target. While wishing not to be limited by this theory, the charged droplets form a space charge cloud while in transit to the target. This space charge creates an electric field E which repels the similarly charged droplets to the target by the Coulomb force. When a drop gets close to the target, the electric field from the charged droplet creates an equal and opposite image charge in the conductive target which attracts the droplet.

Several methods for charging droplets are known. Tribocharging (frictional) charging, applying a voltage to the ejector plate and charges the droplets by induction, and charging by high voltage corona discharge to generate gas ions and charge the droplets by Pauthenier field charging and/or diffusion charging are three such examples. In tribocharging the fluid is passed through small orifices, e.g., of a ejector plate or grid, which results in charging. The effect can be enhanced by coating the ejector plate or grid.

The droplet ejecting device includes ejection mechanism. In some implementations, the mechanism includes an ejection plate or substrate. In some implementations, this is coupled to a fluid reservoir, examples of which are discussed herein. One implementation of the ejector mechanism may be a thermal ejector (or "bubble jet"). The implementation of FIG. 1 shows a substrate structure 100 with multiple openings 102 formed into the substrate structure. This can be achieved by any one of a number of known techniques. This substrate can be formed into a microelectromechanical system (MEMS). Bulk micromachining is one of the known technique for forming silicon based MEMS. The MEMS may be formed on a substrate structure, e.g., a silicon substrate. MEMS can be formed in a similar manner to a semiconductor package. Alternatively, the mechanical and electronic components can be formed separately and be subsequently bonded to one another.

In the implementation shown in FIG. 1 only 12 openings are shown for illustrative purposes. However, several hundreds or even many thousands of openings may be formed on a substrate that is, by way of example, 0.5 cm×0.5 cm in surface area. In this implementation the substrate structure is shown upside down with its distal surface 104 and its proximal surface 106. As shown in the implementation of FIG. 1, each of the openings 102 is provided with a heating element 108 surrounding the opening on the distal surface 104. Thus the MEMS device defines a disk-like substrate structure with multiple channels defined by the openings 102 extending in this implementation from the distal to the proximal surface as shown in FIG. 2. The heating elements 108, in this implementation, are shown at the bottom of the channels on the distal surface. Intervening substrate material, referred to herein as streets 110, are formed between the channels 102.

In one implementation the openings may be formed in the substrate have a radius of 37 microns and a substrate thickness of 74 microns with intervening streets of 12 microns for a center-to-center distance of 86 microns. Assuming spherical drops are emitted from each of the openings the volume of material in each opening will be $JIr^2 \times xt = JI(37^2 \times 74) \times 10^{-18} = 3.18 \times 10^{-13}$ m$^3$=318 pico liter. The amount of area (opening and surrounding street area) for each unit or opening is thus $(37+12+37)^2$ µm$^2$=$7.396 \times 10^{-9}$ m$^2$. Thus in a substrate of 0.5 cm×0.5 cm=$0.25 \times 10^{-4}$ m$^2$ this provides for a total of 3380 openings for a total fluid volume in the openings of approximately 1 µl.

In the above implementation a opening size of 74 microns was selected, which provides for rather large drops of fluid. It will be appreciated that the size of opening chosen will depend on the viscosity of the chemical. The duty cycle or rate of firing of the openings also depends on the volume flow that is desired and will depend on the application. In one implementation droplet sizes of the order of 300 pL may be ejected from the ejector fabricated from a substrate with ratio of opening diameter to substrate thickness of 10:1 to 1:10.

In some implementations the use of materials having a higher operating temperature and lower coefficient of thermal expansion and also provide higher thermal conductivity and lower heat capacity for rapid cooling and improved duty cycle control can be utilized. The material preferably also has a high thermal shock parameter, as is provided for example by silicon carbide (SiC) or any of its poly types (different atomic arrangements). In the present implementation the substrate may made from silicon carbide having a 6H crystal lattice configuration.

As mentioned above, while SiC always involves a combination of silicon and carbon, the crystal lattice structure may vary and includes structures such as 3 C (cubic) atomic arrangements with the atoms located at the corners of cubes forming a lattice structure, or a hexagonal (4H or 6H) arrangement that repeats every four or six layers or a rhombohedral arrangement. A comparison of the arrangements and properties of 3C, 4H and 6H are given in the table below. Such properties may provide guidance for the selection of appropriate substrate material.

| Polytype | 3C (β) | 4H | 6H (α) |
|---|---|---|---|
| Crystal structure | Zinc blende (cubic) | Hexagonal | Hexagonal |
| Space group | $T^2_d$-F43m | $C^4_{6v}$-P6$_3$mc | $C^4_{6v}$-P6$_3$mc |
| Person symbol | cF8 | hP8 | hP12 |
| Lattice constants (Å) | 4.3596 | 3.0730; 10.053 | 3.0730; 15.11 |
| Density (g/cm$^3$) | 3.21 | 3.21 | 3.21 |
| Bandgap (eV) | 2.36 | 3.23 | 3.05 |
| Bulk modulus (GPa) | 250 | 220 | 220 |
| Thermal conductivity (W/(cm · K)) | 3.6 | 3.7 | 4.9 |

Figure 3A:
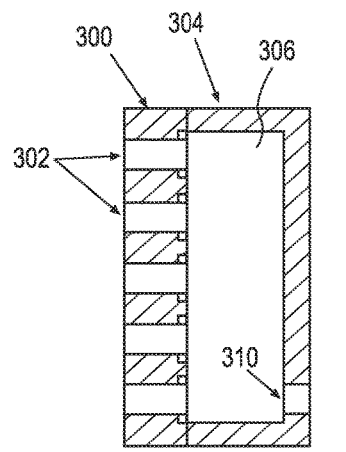
FIG. 3A is a cross-section through an implementation of an ejector device including a reservoir.

As discussed above in this implementation, the substrate is coupled to a reservoir. FIG. 3A, the substrate material 300 with its openings 302 is secured to a substrate having a central cavity 306 etched into it to define a housing 304 which, in this implementation is also made of silicon carbide and defines a chamber 306 between the substrate material 300 and the housing 304. The chamber 306, in its operative state is filled with the fluid to be dispensed. It will be appreciated that more than one housing may be secured to the substrate material 300, thereby allowing some openings in the substrate material 300 to be in flow communication with the fluid in one chamber while other openings are in flow communication with another fluid. This allows fluids to be mixed by firing a selected number of openings from each group. As shown in FIG. 3A, an inlet channel 310 is formed in a wall of the housing 304 to provide fluid communication with a fluid source to replenish the chamber in the housing 304.

Figure 3B:
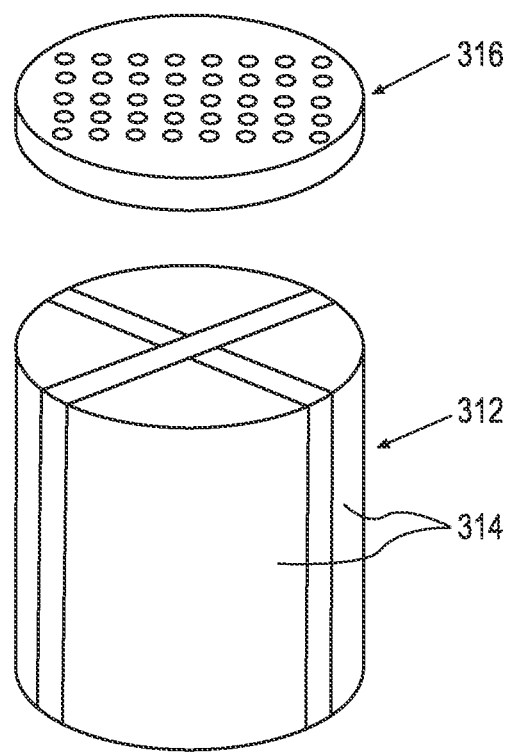
FIG. 3B is an alternative implementation of an ejector device with an alternative reservoir arrangement.

FIG. 3B show an alternative implementation of the invention. In this implementation, more than one medication may be ejected from the thermal ejector, e.g., by providing the ejector with multiple holes and providing some of the holes with a first medication and other holes with a second medication, or by providing multiple reservoirs, each feeding a different set of holes, as is depicted in FIG. 3B, which shows a disposable reservoir unit 700 that, in this implementation, comprises 4 reservoirs 702, which are secured to a substrate structure 710 (shown here prior to attachment to the reservoirs). The controller may be configured to control which holes to fire and the number of times each hole is to be fired in succession, thereby allowing different dosages of the various medications to be provided, either simultaneously, or at different times.

Figure 2:
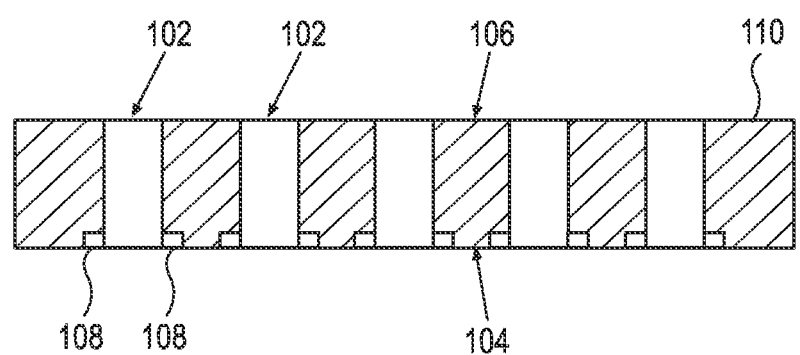
FIG. 2 is cross-section through one implementation of a substrate.

In order to eject fluid droplets from the openings the substrate the heating elements such as the elements 108 shown in FIGS. 1 and 2 are rapidly heated to vaporize the intervening fluid, within the heating element loop to pinch off the fluid in the channel and effectively shooting the fluid droplets out of the opening through the force generated by the fluid vapor. It will be appreciated that droplet size and speed will vary depending on many factors including fluid viscosity, surface tension, ejector plate properties, geometry, and dimensions, as well as operating parameters of the ejector including its duty cycle or drive frequency. By way of example, for opening diameters and length of 5 microns, 15 microns, and 38 µm, the volumes of the droplets are 0.1 picoliter (one millionth of a microliter), 2.7 picoliter and 44 picoliters, respectively.

As mentioned above, the present invention makes use of a substrate material such as SiC, which has a high operating temperature to withstand the high heating of the fluid being ejected, a low coefficient of thermal expansion (meaning that as the temperature changes the material remain pretty constant in size), provides high thermal conductivity (thereby allowing rapid dissipation of heat between heating cycles to allow accurate control of the duty cycle), a low heat capacity, and a high thermal shock parameter. The parameters of the material allow it to rapidly heat the fluid, causing the disk of fluid in the openings that is surrounded by the heating element to heat very quickly to its boiling point, thereby explosively propelling the fluid droplet above the vapor disk from the proximal end of the opening. Other suitable substrate material such as silicon can be used.

Figure 4:
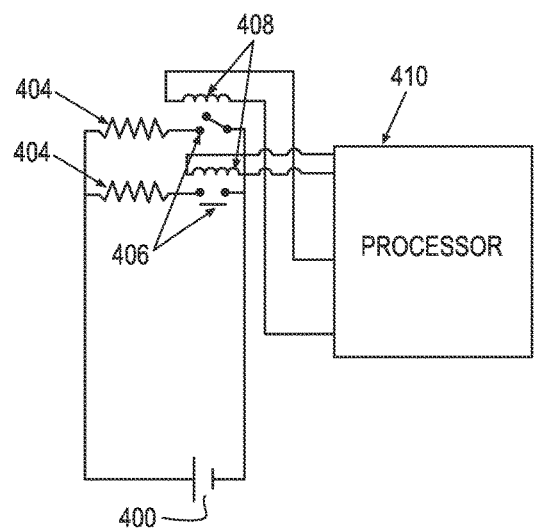
FIG. 4 shows a circuit diagram of one implementation of an electrical circuit forming part of the fluid ejector device of the invention.

In one implementation, an electrical circuit heats the fluid and affects the droplet ejection process. An implementation of this circuit is shown in FIG. 4. An electric power source in the form of a battery 400 or voltage generator is connected in parallel with the heating elements 404. Controllable switches 406 in this implementation takes the form of relays that include a solenoids 408 controlled by a processor 410. While FIG. 4 shows only two resistive elements 404 and two switches 406 controlled by the processor 410, it will be appreciated that the processor 410 preferably controls each of the heating elements formed around the substrate openings. Thus the processor can control which openings and how many openings to fire and how many times per second to do so in order to achieve a desired fluid volume. While this implementation made use of heating elements formed around the openings, other implementations make use of other heating element configurations, e.g., plates mounted inside, above, or below openings inlet pipes (through which the fluid in the hole is replenished).

One benefit of the implementation is that it provides the ability to accurately control droplet ejections by controlling openings to fire and the selection of the number of openings to be fired. It also allows two or more medications to be mixed at time of ejection by providing different sets of openings with different reservoirs filled with different medications. The ratios of two or more medications can be accurately controlled by determining the number of openings to fire from each set or by adjusting the duty cycles for each set. The small droplet size of the medications emitted from the substrate material also ensures thorough mixing of the medications as they are emitted.

Figure 5:
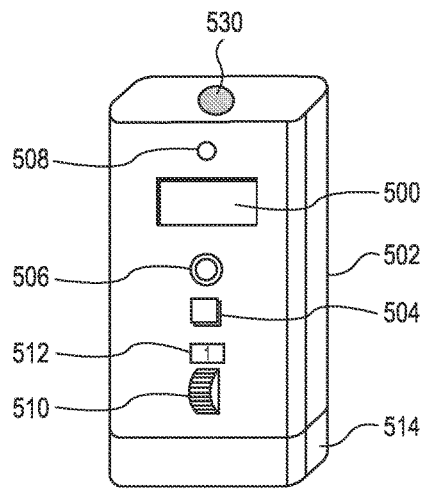
FIG. 5 shows a three-dimensional view of a housing of the device.

One implementation of the droplet ejection device is shown in FIG. 5. It shows a substrate structure 500 of a thermal ejector implemented as a MEMS device and housed in a housing 502. The housing 502 includes a hand-actuated trigger 504, an eye-sensor 506 in the form of a CCD array or near infrared (NIR) sensor to detect an eyeball or the retina of the eye, a light source 508 (in this case a focused LED providing a low intensity light substantially along the ejection path of the thermally ejected fluid droplets), and a reservoir 514 which in this case is releasably attached to the housing 502 and is in flow communication with the holes in the substrate structure 500. The reservoirs can be refillable, allowing the rest of the applicator to be refillable.

Figure 6:
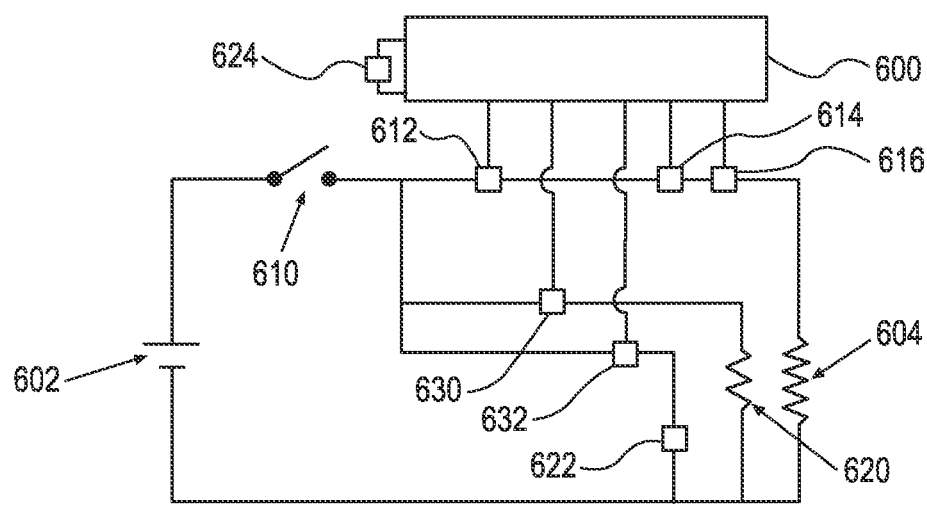
FIG. 6 shows a circuit diagram of an electrical circuit used in one implementation of the device.

FIG. 6 shows a processor 600 is mounted on a circuit board inside the housing 502 and controls the flow of current through an electrical circuit from a power source 602 (implemented in this implementation by a battery) to the heating elements 604 of the thermal ejector. In this implementation the electrical circuit includes three switches connected in series as shown by the circuit in FIG. 6. The first switch 610 is controlled by the hand-actuated trigger 604. The second switch 612 is controlled by the processor 600 in response to signals provided by the eye-sensor 506. The circuit also includes a second heating element 620, a Peltier cooler 622 that are selectively activated based on signals provided to the processor 600 by a temperature sensor 624. In response the processor 600 closes the switch 630 or 632 to either heat or cool the fluid in the holes of the substrate structure. Other suitable circuits may be substituted for that shown in FIG. 6.

Figure 7:
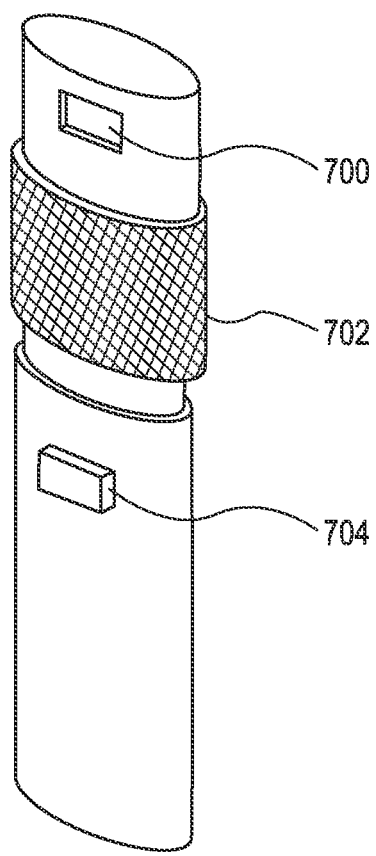
FIG. 7 shows a three-dimensional view of another implementation of the housing of the device.

Another implementation of the invention is shown in FIG. 7, which shows a three dimensional view of contact lens solution dispenser of the invention. In this implementation the fluid is dispensed using a thermal ejector 700. A cover 702 is shown in its retracted position but is movable to a closed position by sliding the cover 702 upward so as to cover the thermal ejector 700. A button 704, which can be thumb-activated, controls the dispensing of the fluid. This implementation may also be implemented as a disposable device, as well as portions of it may be disposable. For example, a replaceable reservoir or cartridge can be used. In practice a user may attach the reservoir 512 to the housing e.g., if the reservoir is disposable and requires replacement.

The device can be pointed at the target, for example, an human or animal eye, using an LED, e.g. LED 708, to help in correctly aligning the applicator. Once the eye-sensor, e.g., sensor 506, detects an eye, it sends a signal to the processor 600, which closes the second switch 612, which is implemented as a relay in this implementation, to allow current to pass from the power source to the heating elements of the thermal ejector. One implementation of the device which could be embodied in any of the implementations may include an ejector assembly and LED that turns on when the device is switched on, for example, by a power switch or lifting the device out of a docking station. The light from the LED is shone onto the target, e.g., the subject's eye to correctly target the eye prior to dispensing fluid. The device may include a rest, support, or spacer to aid in alignment as discussed below.

Other implementations to ensure correct alignment of the device with the eye are also contemplated. These implementations, examples of which are shown in FIGS. 8-13B may be formed as handheld or palmheld units and can be miniaturized to the a further extent for additional applications. In one implementation, shown in FIGS. 8 and 9 a mirror 800 is provided on the housing for reflecting an image of the user's eye back into the user's eye when the device is correctly aligned with the eye. In this implementation a cross-hair is provided on the mirror, as shown in the front view of FIG. 9, to help the user centralize the device for ejection of fluid into the eye. The implementation of FIGS. 1 and 2 also includes an LED 810 to alert the user when a dose is due and a second LED 812 to light up when a full dose has been delivered.

Figure 9:
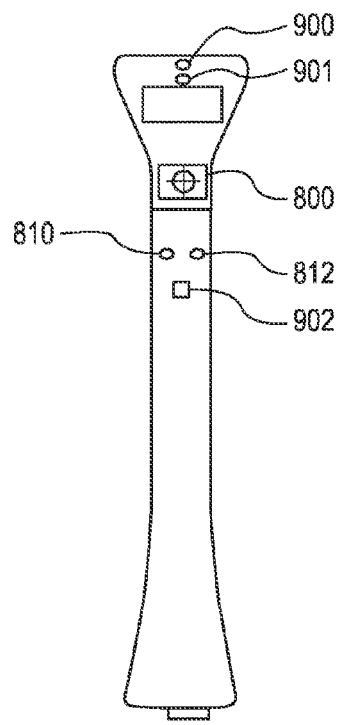
FIG. 9 shows a front view of an implementation of FIG. 8.

FIG. 9 shows another implementation. An infra-red transmitter 800 (e.g., IR LED) and infrared (IR) photo detector 901 are mounted on the front surface of the device to transmit an infra red beam or pulse, which is received by an IR photo detector 902 when the device is correctly aligned with the eye and the IR beam or pulse is reflected off the eye.

Figure 10:
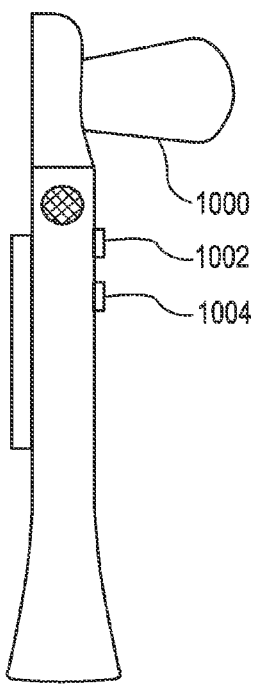
FIG. 10 shows a side view of another implementation of the device.

Yet another implementation of the invention is shown in FIG. 10, which makes use of a conical sleeve 1000 to position the eye relative to the thermal ejector. The sleeve 1000 can, for example, be implemented as a rubber or silicon hood, and may serve the additional function of providing a shaded or darkened imaging zone for imaging the eye with a scanner or camera. A button 1002 is mounted on the device for triggering the ejection of the fluid, and a second button 1004 serves to trigger an image capturing device (not shown) mounted on the device under the sleeve 1000.

Figure 11:
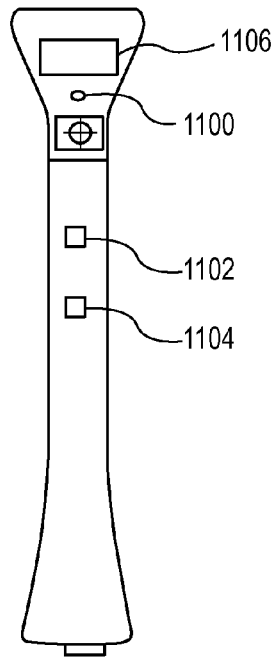
FIG. 11 shows a front view of yet another implementation of the device.

FIG. 11 shows another implementation a low intensity light beam e.g., light emitting diode (LED) 1100 emits a beam when button 1102 is depressed. The light beam is configured to shine into the user's eye when the thermal ejector 1106 or other fluid dispenser of the device is correctly aligned with the eye, as shown by the implementation of FIG. 11. This implementation does not have a camera for capturing an image of the eye, but serves simply to dispense fluid, e.g., a flushing fluid or medication into the eye by depressing a button or switch 1104. The button 1104, in the case of a thermal ejector closes a switch to heat the heating elements of the thermal ejector or sends a signal to a controller for controlling one or more heating elements of the ejector as is described in greater detail below.

Figure 12:
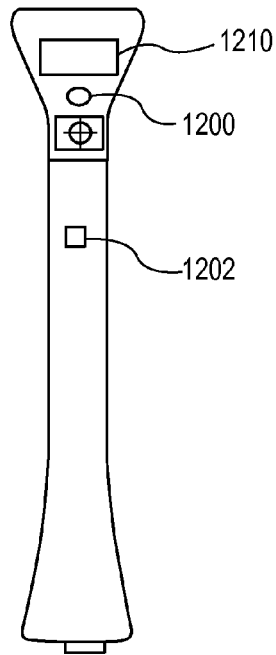
FIG. 12 shows a front view of yet another implementation of the device.
Figure 13A:
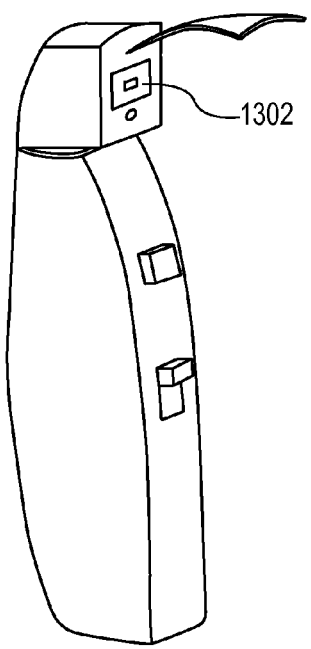
FIGS. 13A-B show another implementation of the device including a spacer.
Figure 13B:
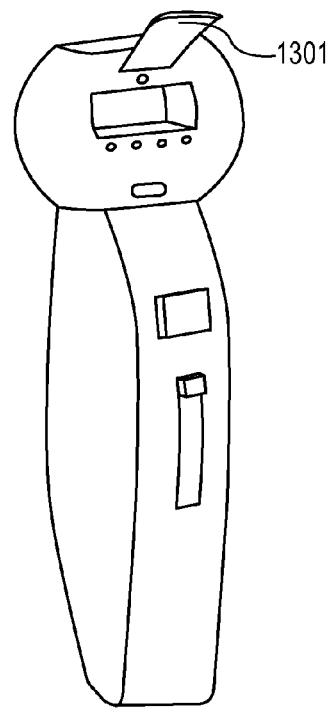
Figure 15B:
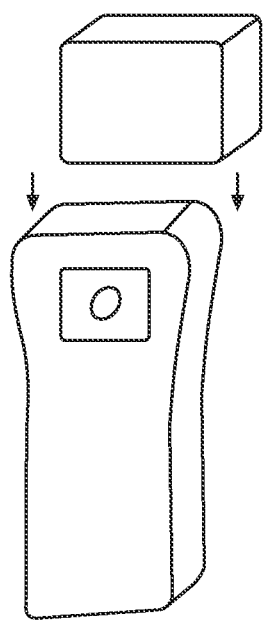
FIGS. 15B-H show various examples of covers.
Figure 15C:
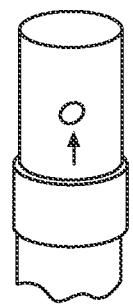
Figure 15D:
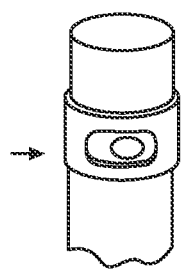
Figure 15E:
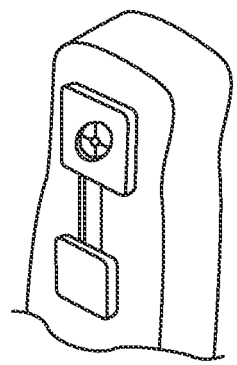
Figure 15F:
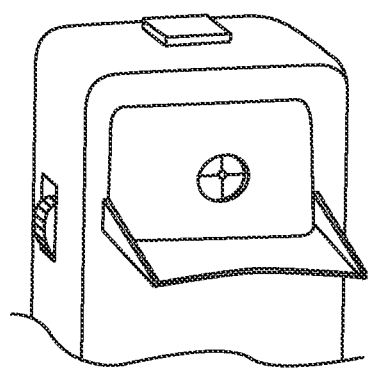
Figure 15H:
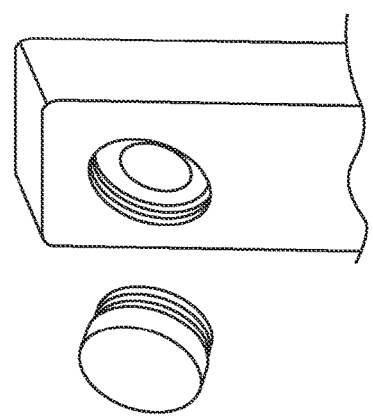
Figure 15G:
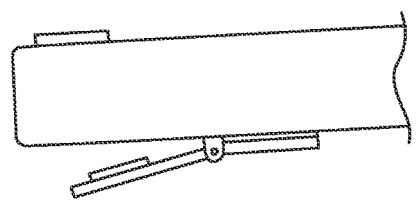

In FIG. 12, an image capture device, including cameras, scanners, or other sensors without limitation, e.g. charge coupled device (CCD), 1200, may provided to detect the presence of an eye and to ensure that the eye is open. The eye sensor provides control information, which in one implementation provides a controlling signal to a controller or processor in the device for controlling the ejection of fluid. Thus, a processor is included in such implementations to control the activation of the ejector mechanism to eject fluids only when the camera image indicates that the eye or a pre-defined area of the eye is correctly aligned with the fluid applicator. Thus, for example, with a thermal ejector, only the holes that are correctly aligned with the eye may eject fluid. The device can readily take into account the delay between the signal from the camera and the ejection of droplets from the device and can time delivery to beat the blink cycle.

Implementations of the device provides numerous benefits over other devices for many reasons. For example, not only does it ensure that the fluid that is dispensed is dispensed into the eye by allowing the device to be correctly aligned, the device is capable of dispensing at speeds that ensure beating the blink of an eye. Using a thermal ejector based system in accordance with the invention and integrating it with an optical camera or other eye detector or eye sensor, to provide feedback to the device ensures that the eyelid is open and that the eye is correctly aligned with the thermal ejector. Only when the eye is determined to be open will the applicator of the invention dispense a carefully measured dose of medication or vaccine in the form of a fine mist directly into the eye. The sub-second response time, is particularly useful for people or animals who are sensitive to anything coming close to their eye by ensuring that the speed of delivery is able to "beat the blink". Other benefits of the device include delivering quantifiable and repeatable results by selectively dispensing a precisely controllable volume of fluid such as a medication or vaccine.

Different implementations as understood and disclosed permit a user to turn on the device. A user may simply lift the device off of a base which then activates or turns on the device. The user can also turn on the device by depressing a trigger, such as trigger 504. In some implementations, where the ejector mechanism is thermal or ultrasonic, engaging the trigger or turning on the device, commences to heat or cool the device or portions thereof to a predetermined temperature. For example, the device may be heated or cooled to the body temperature of a human or animal.

Figure 8:
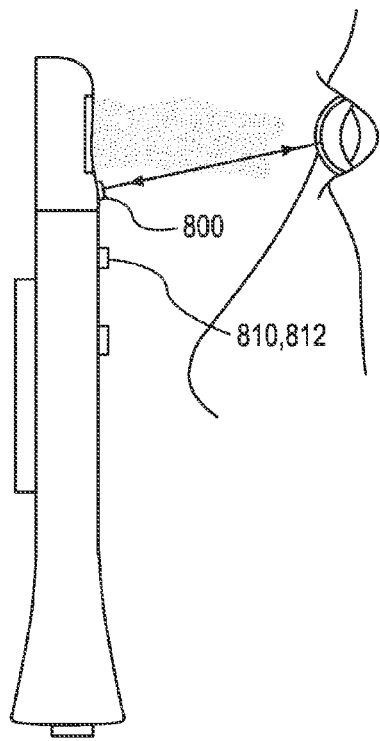
FIG. 8 shows a side view of one implementation of the invention delivering medication to a human eye.

After the device is turned on, the ejection mechanism can be triggered. In the implementation of FIGS. 8 and 9, activation trigger 802 serves as the triggering mechanism to fire the holes of the actuation mechanism, subject to control by a controller in the device that monitors the amount of fluid that needs to be dispensed and the amount of fluid that has already been dispensed. Of course, the button can be any suitable means to turn on a device including electrical and mechanical activation triggers, pushbuttons, levers, slide switches, tactile switches including momentary switches, pressure pads, motion sensors, magnetic and Hall effect switches, electrostatic switches, resistive or capacitive touch switches, Reeves switches, switches operated by infra-red, radio frequency, light, or sound detectors, or timers or internal activation signals. The activation may be local or remotely controlled.

Some implementations may include a watchdog timer which monitors the device to ensure proper operation. In another implementation, the device may sense the presence of the droplet steam for self-diagnostic purposes and to confirm proper operation. By way of example, one or more light emitters, e.g., LED, laser diode, may be used to shine light against the droplet stream. In one implementation, the light may be shown perpendicularly to the stream. A device may include, in one implementation, light detectors, e.g., photo detector, which may be used in conjunction with a shone light to detect reflection and refraction, such as reflection of the shone light off of the stream, and use this detection to determine proper operation of the device. A system may further react in response to the detection and determination of proper operation, e.g., by alerting a compliance agent or system that the device may not be properly functioning.

In the implementation of FIG. 12, the device also includes a hand operated trigger 1202, however, in this implementation the ejection is subject to correct positioning of the ejector mechanism 1210 relative to the eye as defined by the image information obtained from the camera 1200.

The illumination mechanism, such as the LED explained above, may be in ranges above 280 nm, including, e.g., 290-1600 nm, wavelengths for illuminating the target. The illumination mechanism may be operable to pulse the light for different periods of time, e.g., 120 ns to limit pupil reaction and permit analysis of the eye with different frequency optical detectors, scanners, or cameras as explained above. Furthermore, the device may include an adaptive optics chip to perform wavefront correction for clearer images. The device may also include a fixation source e.g., an LED or LED pattern to define a moving eye-focusing image and assist with pediatric usage. This also serves to move or rotate the eyeball during application of medication to assist in spreading the medication across the corneal surface.

Features of the devices can be formed in alternative implementation. The following are a few examples. FIGS. 13A and 13B show another implementation of the invention. The device shown in FIG. 13B, the ejector includes a removable reservoir 1300, which allows both the reservoir and ejector to be discarded once the fluid in the reservoir is depleted. This helps to maintain a sterile dispensing area and avoids excessive build-up of dust and dirt on the thermal ejector. Also, FIGS. 13A and 13B depict a cover which is hinged in these implementations. Cover 1301 flips down to provide a cover for the ejector. This protects the ejector mechanism when not in use or in transport. Also, by engaging with a peripheral seal 1302, the cover 1301 reduces evaporation of fluid. Cover 1301 can also be used as a spacer or rest to rest against, for example, the eyebrow, to align the device against the target, for example the eye.

The cover may also hinge up as shown in FIGS. 14A and 14B. A spacer may also be formed as a separate or integral piece on the exterior of the device as depicted by 1500 in FIG. 15A. The spacer rests against a portion of the anatomy to aid in alignment of the device with the target. In addition to the noted covers, the cover may be omitted. Additionally, the cover can be of any suitable mechanism, including iris-type closure, covers that slide from left to right, cover that are coupled via a friction fit, in a threaded manner, louvered, or clipped on. The cover can be coupled with any suitable mechanical, magnetic, or electromechanical means. For disposable packages, the cover may be an exterior or protective wrapping or covering. Additionally, the cover may be sealed against the ejection area with a leaf spring or other polymeric seal. This seal can be made of a suitable polymer, for example, polypropylene, polyethylene, high density polyethylene or teflon. Furthermore, other seals such as ceramic sealers, metallic sealers, or gaskets can be used to seal the cover against the housing. FIG. 15B-H show several alternative implementations of covers.

In some instances, it may be desirable to control the temperature of the fluid in the device outside of the ejection cycle. In these implementations, the device may include a cooler, e.g., a Peltier device, for keeping the fluid cool where needed. The device may also include a heater for warming the fluid to a predefined temperature, e.g., the eye surface temperature of the person to whom the fluid is to be administered. The temperature range may be controlled by the controller.

In addition to the thermal and ultrasonic ejector mechanism, the ejector mechanism may be piezoelectric. Referring to FIG. 16A, an assembly 1600 may include an ejector mechanism 1601 and reservoir 1620. The ejector mechanism 1601 may include an ejector plate 1602 that can be activated to vibrate and deliver a fluid 1610, contained in a reservoir 1620, in the form of ejected droplets 1612 along a direction 1614. In the example of FIG. 16A, the fluid may again be an ophthalmic fluid that is ejected towards an eye 1616 of a human adult, child, or animal. Additionally, the fluid may contain an active pharmaceutical to treat a discomfort, condition, or disease of a human or an animal.

Figure 16B:
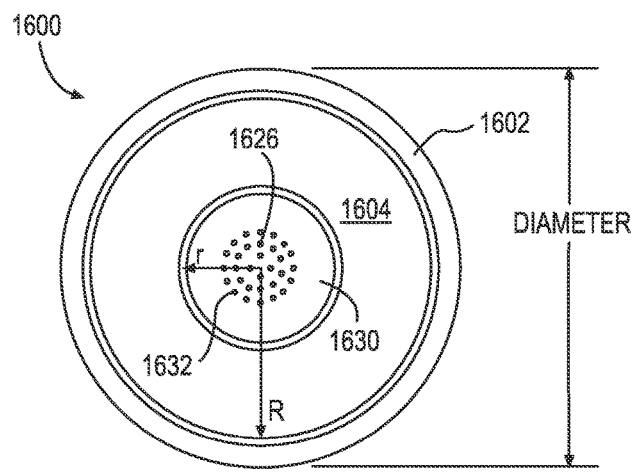
FIG. 16B shows an enlarged top view of the assembly.
Figure 16C:
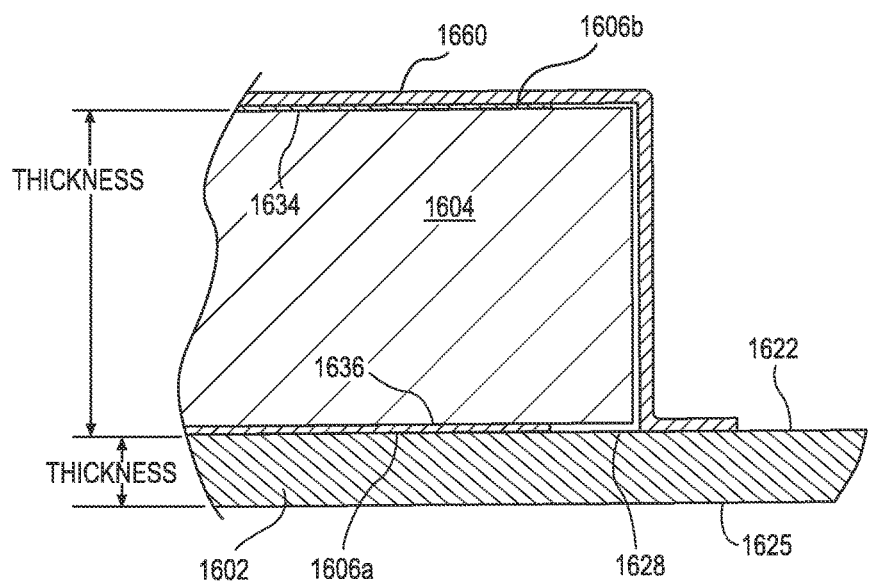
FIG. 16C shows an enlarged cross-sectional view of a portion of the assembly.

Referring to FIGS. 16A-16C, the ejector plate 1602 as shown has a circular shape with two opposite surfaces 1622, 1625. Although not shown, the ejector plate can also have other shapes, e.g., an oval, square, or generally polygonal shape. Additionally, the ejector plate need not be flat. The plate may include a surface curvature making it concave or convex. The ejector plate may be a perforated plate that contains at least one opening 1626. The opening or openings 1626 form the droplets as fluid 1610 is passed through. The ejector plate 1602 may include any suitable configuration of openings, one configuration being depicted in FIGS. 16A, 16B, and 16F. The openings may be formed in an ejector plate, a grid, a spiral, rectangular, rectilinear, or other pattern. The pattern may be regular or irregular. The pattern may maintain a uniform spacing of openings, or the spacing may be varied. For example, the density of openings may increase or decrease towards the center of the plate. The pattern may also cover all or part of the plate. These patterns are not limited to piezoelectric ejection devices and may be used in conjunction with the other types of ejection mechanisms, including thermal and ultrasonic. A more detailed discussion of the pattern and the region 1632 containing openings 1626 appears below.

Additionally, the openings 1626 may be formed in any suitable shape or volume with an appropriate aspect ratio. One example is shown in FIG. 16A. FIG. 16A shows openings having a cylindrical shape, that is, the diameter of the opening extending from surface 1622 to 1625 remains generally constant. Nevertheless, the openings need not be limited to this cylindrical shape and may be tapered or conical. The tapered may extend the entire thickness from surface 1622 to 1625, or it may extend part way. The opening may also be beveled on one or both sides. The bevel may be have an angled edge or a curved edge. The cross section of the opening may be round as shown in FIG. 16F or may have any other suitable shape. A few examples may be round, oval, rectangular or polygonal. The openings may be regularly shaped or irregularly shaped. The shape may be symmetric or asymmetric. The size and shape of the openings 1626 affects the size and shape of the droplets and the droplet stream created by the ejection mechanism 1601. It may also affect the density distribution throughout the droplet stream. Thus, the size and shape of the openings as well as their pattern is selected to produce the desired properties of the droplet stream in accordance with the principles and teachings of the present disclosure. The properties of the droplet stream affect delivery of the fluid and the dosage of any therapeutic or active ingredient. The properties of the stream also affect the subjects' comfort. For example, a stream which delivers too much force would induce pain or discomfort. Such a stream may also induce tearing or blinking which in turn may reduce the amount of fluid effectively delivered to the subject. In contrast, an appropriately formulated stream will have little to no discomfort and will not induce blinking or tearing. A few examples of different shapes for the openings are shown in FIGS. 16L-16R. These shapes are not limited to piezoelectric ejection devices and may be used in conjunction with the other types of ejection mechanisms, including thermal and ultrasonic.

Ejector plate 1602 is coupled to an ejector which activates the plate to form the droplets upon activation. The manner and location of attachment of the ejector 1604 to the plate 1602 affects the operation of the ejection assembly and the creation of the droplet stream. In the implementation of FIG. 16B, the ejector 1604 is coupled to a peripheral region of surface 1622 of plate 1602. Center region 1630 is not covered by the piezoelectric ejector 1604. Region 1632 of ejector plate 1602 contains a central region 1630 which contains one or more openings 1626. The fluid 1610 is passed through openings 1626 to form droplets 1612. The piezoelectric ejector 1604 may be of any suitable shape or material. For example, the ejector may have an oval, a square, or a generally polygonal shape. The ejector 1604 may conform to the shape of the ejector plate 1602, or regions 1630/1632. Alternatively, the ejector 1604 may have a different shape. Furthermore, the ejector 1604 may be coupled to the plate 1602 or surface 1622 in one or more sections. In the example shown in FIG. 16B, the piezoelectric ejector 1604 is illustrated in the shape of a ring. that is concentric to the regions 1630 and 1632. The openings 1626 may be located in ejection region 1632. Region 1632 may occupy a portion of region 1630, as shown in FIG. 16B, or may occupy the entire area of region 1630 (not shown). The portion of region 1630 occupied by region 1632 may be in the center of region 1632 or it may be offset from the center (not shown). In some implementations, for example as depicted in FIGS. 16A and 16E, the size of the region 1638 of the reservoir housing 1608 corresponds substantially to the size of ejection region 1632. In some implementations, the open region 1638 may be substantially larger than the ejection region 1632.

As with the size and shape of the openings 1626, the size and shape of the ejection region 1632 can be selected based on the desired properties of the droplet stream. As shown in FIG. 16F, by way of example, the openings 1626 are arranged in a circular pattern in the ejection region 1632 of the ejector plate 1602, but other patterns may also be used as explained above. The distance l between adjacent openings 126 may be any suitable value, including, 1 microns to a few mm, e.g., 150 microns to 300 microns. In one particular implementation, l is chosen to be 200 microns. Additionally, also as explained above, the separation of the openings 1626 need not be uniform.

FIG. 16D, depicts ejector plate 1602 disposed over reservoir housing 1608 which contains fluid 1610. Surface 1625 of plate 1602 is adjacent to the fluid 1610. Reservoir 1608 has open region 1638 as shown in FIG. 16E which is adjacent to surface 1625 and to the region 1632 of plate 1602. In this implementation, surface 1625 encloses the fluid 1610 in the reservoir 1608. The reservoir housing 1608 can be coupled to the ejector plate 1602 at a peripheral region 1646 of the surface 1625 using a suitable seal or coupling. By way of example, FIG. 16E shows O-ring 1648a. Although not shown, more than one O-ring can be used. As known in the art, the O-rings may have any suitable cross-sectional shape. Furthermore, other couplers such as polymeric, ceramic, or metallic seals can be used to couple housing 1608 to the ejector plate 1602. Alternatively, the coupling can be eliminated altogether and the housing 1608 can be integrally connected to plate 1602, for example by welding or over molding. In such an implementation, an opening through which fluid is supplied to reservoir housing 1608 may be provided. Further still, the couplings may be made removable, such as a hinge, or may be made flexible or nonrigid connector, e.g., polymeric connector. When the housing 1608 is coupled to the ejector plate and fluid 1610 is contained within the reservoir, the fluid 1610 does not leak between use cycles-even if the openings 1626 are exposed to the exterior. This is due to the surface tension of the fluid 1610 given the size scale of the openings. The peripheral region 1646 can at least partially overlap with the peripheral region 1624 and can extend beyond the peripheral region 1624, although such overlap is not required. The contact in which the reservoir housing 1608 and the ejector plate 1602 are coupled to each other is relatively small so that the attachment of the reservoir housing 1608 to plate 1602 does not substantially affect the vibration of the ejector plate 1602 when the ejector plate is activated.

Other than the open region 1638, portions of the ejector plate 1602 may be covered by an additional reservoir wall 1650. In the implementation of FIG. 16E, wall 1650 does not directly contact the ejector plate 1602, rather it is coupled to O-rings 1648a. Alternatively, wall 1650 can be directly attached to plate 1602. Furthermore, housing 1608 can be directly attached to plate 1602 and wall 1650 can be omitted altogether.

As the ejection assembly 1600 is used for delivering therapeutic agents or other fluids to eyes, the ejection assembly 1600 is designed to prevent the fluid 1610 contained in the reservoir 1620 and the ejected droplets 1612 from being contaminated. In some implementations, for example, as shown in FIG. 16C, a coating 160 can be formed over the exposed surface of the piezoelectric ejector 1604 and at least a part of the surface 1622 of the ejector plate 1602. The coating may be used to prevent direct contact of the piezoelectric ejector 1604 and the electrodes 1606a and 1606b with the fluid 1610. The coating may be used to prevent interaction of the plate or ejector with the fluid or it may be used to protect the piezoelectric ejector 1604 and electrodes 1606a and 1606b from the environment. For example, the coating can be a conformal coating include a nonreactive material, e.g., polymers including polypropylene, nylon, or high density polyethylene (HDPE), gold, platinum, or palladium, or coatings such as Teflon®.

Referring to FIG. 16G, in some implementations, the ejector plate 1602 can be coated with a protective coating 1662 that is anti-contamination and/or anti-microbial. The protective coating 1662 can be conformal over all surfaces of the ejector plate 1602, including surfaces 1664 defining the openings 1626 (only one opening shown). In other implementations, the protective coating 1662 can be applied over selected surfaces, e.g., the surfaces 1622, 1625, or surface regions, e.g., parts of the surfaces 1622, 1625, 1664. The protective coating can be formed of a biocompatible metal, e.g., gold, iridium, rhodium, platinum, palladiums or alloys thereof, or a biocompatible polymer, e.g., polypropylene, HDPE, or Teflon®. Antimicrobial materials include metals such as silver or polymers such as polyketones. The protective coating can be in direct contact with the fluid 1610 or the droplets 1612. The coating may provide an inert barrier around the fluid or may inhibit microbial growth and sanitize the fluid 1610 and/or the droplets 1612.

Additionally, surface 1622 of plate 1602, e.g. FIGS. 16A and 16E, may also be coated. The coating may be a hydrophilic or hydrophobic coating. Additionally, the coating may be coated with a protective later. The surface may also be coated with a reflective layer. A coating layer may be both protective and reflective. Alternatively, the surface may have been formed to be reflective. For example, the surface may be made of stainless, nickel-cobalt, or other reflective material. A surface may have been formed or polished to be reflective. In addition to making the surface 1622 reflective, the surface may also be backlit on its surface or around its perimeter and shown in FIG. 26. In ophthalmic applications, a reflective surface aids the user in aligning the ejector assembly with the eye.

In some implementations, the ejector plate 1602 can itself be formed of a metal, e.g., stainless steel, nickel, cobalt, titanium, iridium, platinum, or palladium or alloys thereof. Alternatively, the plate can be formed of suitable material, including other metals or polymers, and be coated as noted above. The plate may be a composite of one of more materials or layers. The plate may be fabricated for example by cutting from sheet metal, pre-forming, rolling, casting or otherwise shaping. The openings in the plate may be formed using suitable methods including but not limited to drilling by mechanical or optical means such as laser drilling or ablation, or chemical processing such as etching with or without stencils or lithographic patterning. The openings may also be pre-formed at the time of forming the plate. The coatings may be pre-formed by dipping, plating, including electroplating, or otherwise encapsulating such as by molding or casting. The coatings may also be deposited by suitable deposition techniques such as sputtering, vapor deposition including physical vapor deposition (PAD), chemical vapor deposition (COD), or electrostatic powder deposition. The protective coating may have a thickness of about less than 0.1 µm to about 500 µm. It is desirable that the coating adhere to the plate 102 sufficiently to prevent delamination when vibrating at a high frequency.

The configuration of the reservoir 1620, including the shape and dimension, can be selected based on the amount of fluid 1610 to be stored and the geometry of the ejector plate 1602. Alternative forms of reservoirs include gravity-fed, wicking, or collapsible bladders which operate under pressure differentials. These reservoirs may be prefilled, filled using a micro-pump or by replacement of a cartridge. The micro pump may fill the reservoir by pumping fluid into or out of a collapsible container or a noncollapsible one. The cartridge may include A container which is loaded into the reservoir. Alternatively, the cartridge itself may be coupled to a disposable ejector assembly which is then replaced within the housing after a specified number of discharges.

Figure 16I:
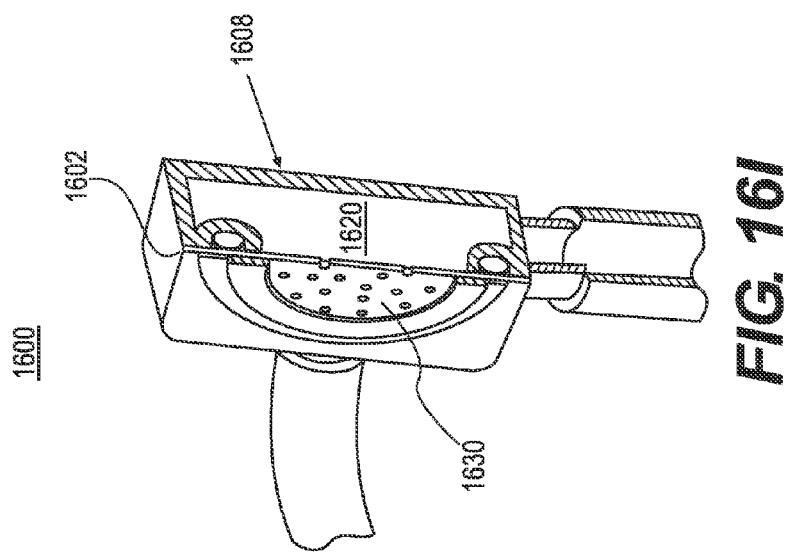
FIG. 16I shows a sectional view of a portion of the assembly shown in FIG. 16H.
Figure 16H:
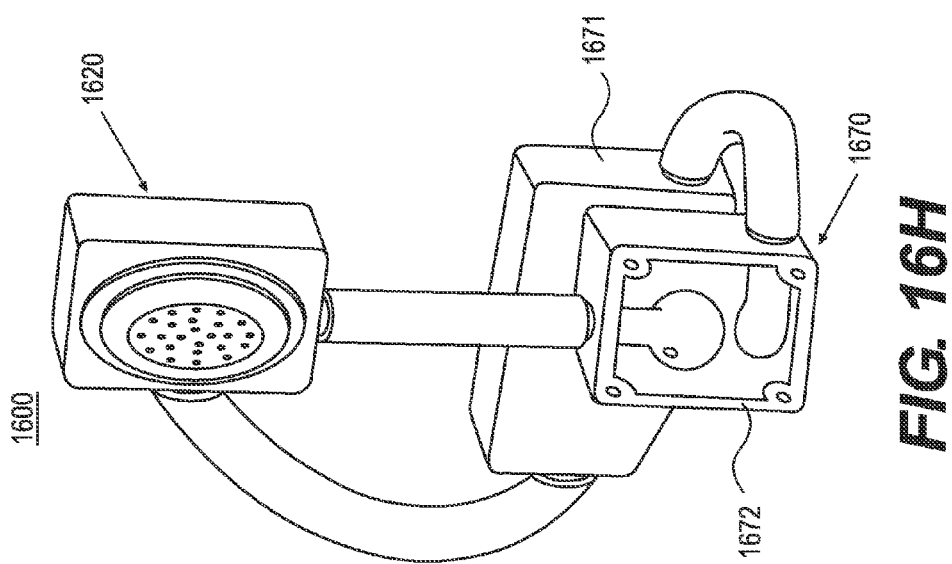
FIG. 16H shows a perspective view of a portion of the assembly, including an alternative implementation of the reservoir.
Figure 16L:
FIGS. 16L-R show partial cross-sectional views showing examples of shapes for the openings in the ejector plate.
Figure 16M:
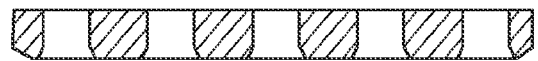
Figure 16N:
Figure 16O:
Figure 16P:
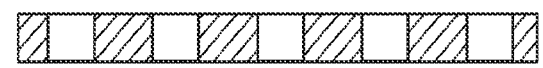
Figure 16Q:
Figure 16R:

FIG. 16H shows a reservoir 1620 connected to a micro-pump assembly 1670. The assembly includes micro-pump 1672 and a larger reservoir 1671. FIG. 16I shows a sectional view of assembly 1600. An alternative reservoir for use with the device is depicted in 20. Reservoir housing 1608' is coupled to the ejector mechanism. The housing 1608' includes wicking material W. This material maintains a supply of fluid against the ejector mechanism even when the fluid level falls below the ejector plate 1602. Not wishing to be limited by this theory, this type of reservoir operates by capillary action. An implementation of this reservoir types is more fully described in U.S. Pat. No. 7,192,129 to Droege.

In the example shown in FIG. 16D, the reservoir housing 1608 has a rectangular cross-section. Other shapes can also be used. In some implementations, the reservoir housing 1608 includes curved edges. An example showing curved corners 140 is depicted in FIG. 16D. Thus, little or no fluid 1610 is trapped in the edges of the reservoir 120 and the fluid in the reservoir can be effectively used. The reservoir 1620 can be refillable or disposable. The reservoir can be prefilled for disposable reservoirs or can be refillable using a fill hole.

In some implementations, the reservoir housing 1608 includes through holes 1642 (only one shown in FIG. 16A to allow air to escape from or enter the reservoir 1620 and keep the fluid 1610 in the reservoir at the appropriate ambient pressure. The through holes 1642 have a small diameter so that the fluid 1610 does not leak from the holes. Alternatively, no openings are formed in the reservoir housing 108, and at least a portion, e.g., the portion 1644 or the entire, reservoir housing 1608 can be collapsible, e.g., in the form of a bladder. The entire reservoir may also be made in the form of a flexible or collapsible bladder. Accordingly, as the fluid 1610 is ejected through the ejector plate 1602, the reservoir 1620 changes its shape and volume to follow the changes in the amount of fluid 1610 in the reservoir 1620.

In the implementation of FIGS. 16A through 17B, the ejector plate 1602 is activated by being vibrated by piezoelectric ejector 1604. As shown in FIGS. 16A and 16C, two electrodes 1606a and 1606b are formed on two opposite surfaces 1634 and 1636 of the piezoelectric ejector 1604 that are parallel to the surface 1622 of the ejector plate 1602 and activate the piezoelectric ejector 1604 to vibrate the ejector plate 1602. The electrodes can be attached to the plate in any known manner including fixing by adhesive or otherwise bonding. They may also be overmolded in place to plate 1602. Wires or other conductive connectors can be used to affect necessary electrical contact between plate 1602 and the electrodes. Alternatively, the electrodes may be formed on the plate 1602 by plating or otherwise depositing in situ. By way of example, the electrodes are attached by adhesive 1628 which is applied between the electrode 1606a and the ejector plate 1602. Electrode 1606a is in electrical contact with plate 1602. When a voltage is applied across the electrodes 1606a and 1606b, the piezoelectric actuator 1604 deflects ejector plate 1602 to change shape to be more concave or convex as shown in FIGS. 17A and 17B. For example, FIG. 17A shows electrode 1606a and 1606b coupled to plate 1602 and causing the plate to deflect into shape 1700. An extensive range of voltages corresponding to different piezoelectric materials are known in the art, but by way of example, a voltage differential of 40 or 60 V may be applied to the electrodes in FIG. 17A. When the direction of the voltage differential is reversed, for example to −40 or −60 the plate will deflect in the opposite direction into shape 1701 as shown in FIG. 17B. In this way, the actuator 1604 causes oscillation of plate 1602 which constitute the vibration that results in formation of the droplets 1612 from fluid 1610. In the implementation shown in FIG. 17A, the volume of reservoir 1620 is reduced and the fluid 1610 in the reservoir 1620 is compressed by the ejector plate 1602 and forced into the openings 1626. In the implementation shown in FIG. 17B, the volume of the reservoir 1620 is increased. As the alternating voltage is applied to electrodes 1606a and 1606b, the ejector plate 1602 oscillates between the shape 2600 and shape 2602, causing the fluid droplets 1612 to accumulate in the openings 1626 and eventually be ejected from the openings 1626 along the direction 1614 away from the reservoir 1620. The frequency and wavelength of oscillation may depend on many factors such as the volume of the openings 1626, the number of openings 1626, the viscosity of the fluid, the stiffness of the plate 1602, temperature and other factors. These parameters may be adjusted or selected to create the desired droplet stream. The frequency of droplet ejection from plate 1602 also depends on many factors. In some implementations, the droplets 1612 are ejected at a frequency lower than the pulse frequency to the piezoelectric actuator 1604. For example, the droplets 1612 are ejected every 1-1000 cycles, and more specifically 8-12 cycles, of the ejector plate vibration. A frequency of droplet ejection is discussed in more detail below.

Many piezoelectric materials can be used to create actuator 1604. By way of example, in some implementations, the piezoelectric actuator can be formed from PZT. But PZT includes lead and should be sealed from fluid 1610. Other lead-free materials include barium titanate or polymer-based piezoelectric materials, such as polyvinylidene fluoride. The electrodes 1606a and 1606b can be formed of suitable conductors including gold, platinum, or silver. Suitable materials for use as the adhesive 1628 can include, but not be limited to, adhesives such as silicone adhesives, epoxies, silver paste. One example of a conductive adhesive includes Thixotropic adhesive such as Dow Corning DA6524 and DA6533. The reservoir housing 1608 can be formed of a polymer material, a few examples of which include Teflon®, rubber, polypropylene, polyethylene, or silicone. As mentioned earlier, all or part of the reservoir can be flexible or collapsible. The size and velocity of the droplets ejected by the ejection assembly 1600 can be affected by various parameters used in fabricating the ejection assembly 1600. The parameters can include dimensions of the piezoelectric actuator 1604, the properties (e.g., dimensions, elasticity and others) of the ejector plate 1602, the size and pattern of the openings 1626 in the ejector plate 1602, the frequency, shape, and magnitude of the pulses applied to the electrodes 1606a, 1606b by the drive electronics, the fluid properties (e.g., the viscosity and surface tension), and others.

The magnitude and frequency of the ejector plate vibration can also be controlled by controlling the voltage pulses applied to the electrodes 1606a, 1606b. As discussed above, the pulses are created by voltage differentials that deflect plate 1602, as shown in FIGS. 17A and 17B. In some implementations, one of the electrodes 1606a or 1606b is grounded and voltage pulses, e.g., bipolar pulses are applied to the other one of the electrodes 1606a or 1606b e.g., to vibrate the ejector plate 1602. Details of the voltage pulses and other features are discussed in further detail herein. By way of example, in one implementation, the piezoelectric actuator 1604 can have a resonant frequency of about 60 KHz to about 120 KHz, e.g., 118 KHz. The applied voltage pulses can have a frequency lower, higher, or the same as the resonant frequency of the piezoelectric actuator 1604.

In the implementation of FIG. 16A, the delivery time of the droplets is about 0.1 ms to about several seconds. Without wishing to be bound by theory, it is believed that human eyes take about 300 ms to about 400 ms between blinks. Therefore, for implementations where delivery is desired to be between blinks, the delivery time may be about 50 ms to about 300 ms and more particularly 25 ms to 200 ms. In one implementation, the delivery time is 50 ms to 100 ms. In this way, the ejected droplets can be effectively delivered and deposited in the eye during a blinking cycle of the eye. In some implementations, for example over-the-counter saline dispensers, the delivery time can be as long as several seconds, e.g., 3-4 seconds, spanning several blink cycles. Alternatively, a single delivery can be administered by several bursts or pulses of droplet ejection.

Additionally, and not intending to be bound to this theory, pulsing might reduce the peak amplitude of the airstream by spreading the impulse out over time, similar to the effect of an automobile crumple zone during a crash. Therefore, the pressure of the ejection on the target may be mitigated. That is, e.g., for an ocular application, the subject might not feel as much air and experience higher discomfort levels. Furthermore, pulsing may also reduce droplet agglomeration and result in less entrained air generation. By way of a single example, pulses of 25 ms can be administered with stop times of 25 ms separating the pulses. By way of example, in one implementation, the pulses may be repeated for a total of 150 ms total time.

Figure 21B:
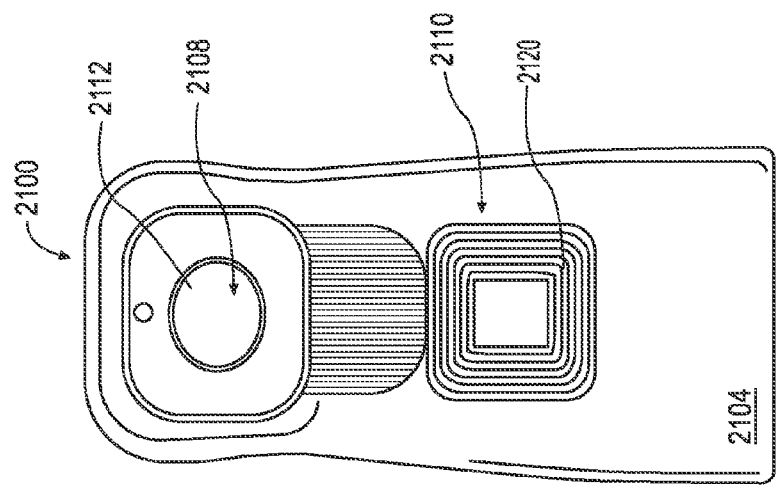
FIG. 21B shows an alternative implementation of the device with the slide cover opened.
Figure 21A:
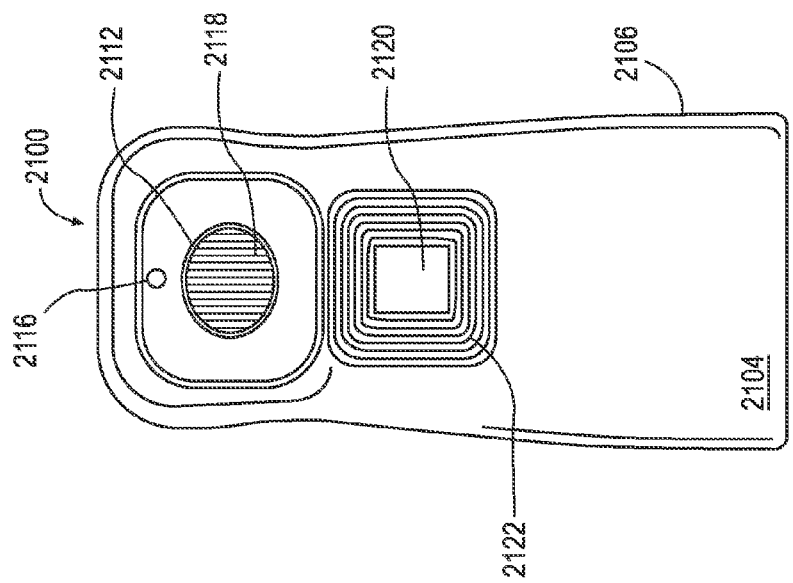
FIG. 21A shows an alternative implementation of the device with a slide cover in the closed position.
Figure 21D:
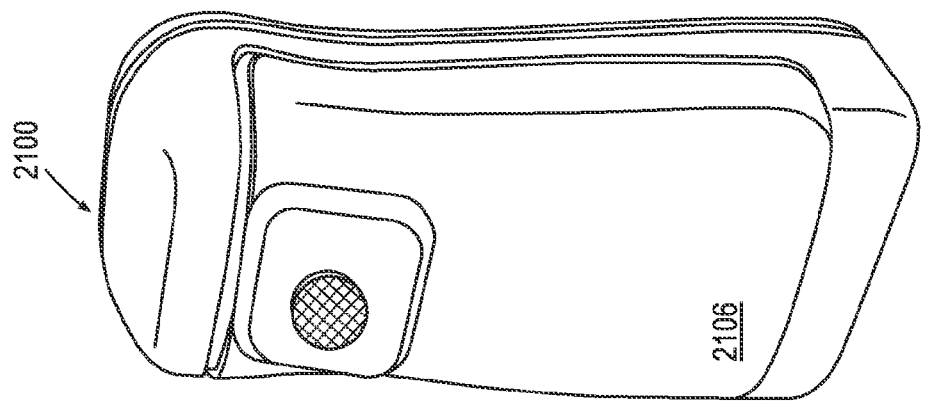
FIG. 21D shows a perspective view of the rear of the device shown in FIG. 21A.
Figure 21C:
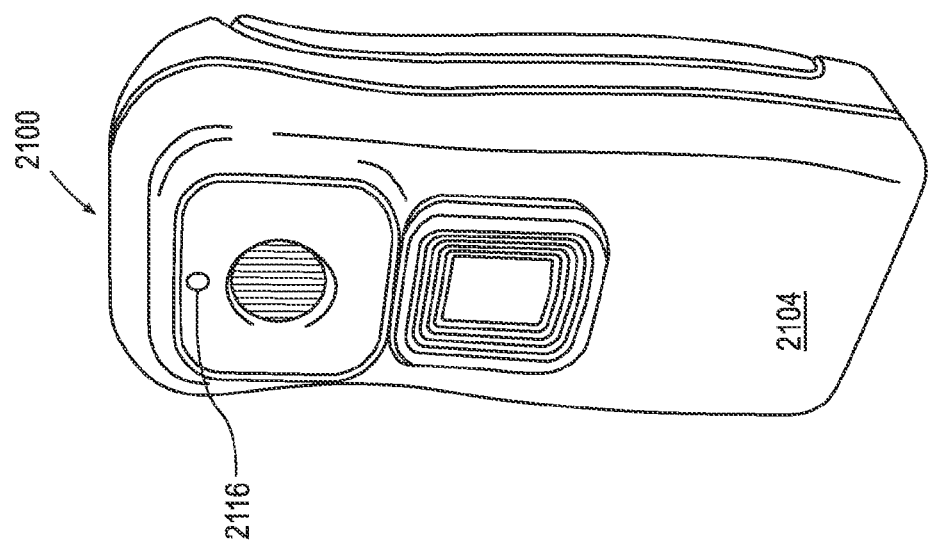
FIG. 21C shows a perspective view of FIG. 21A.
Figure 21E:
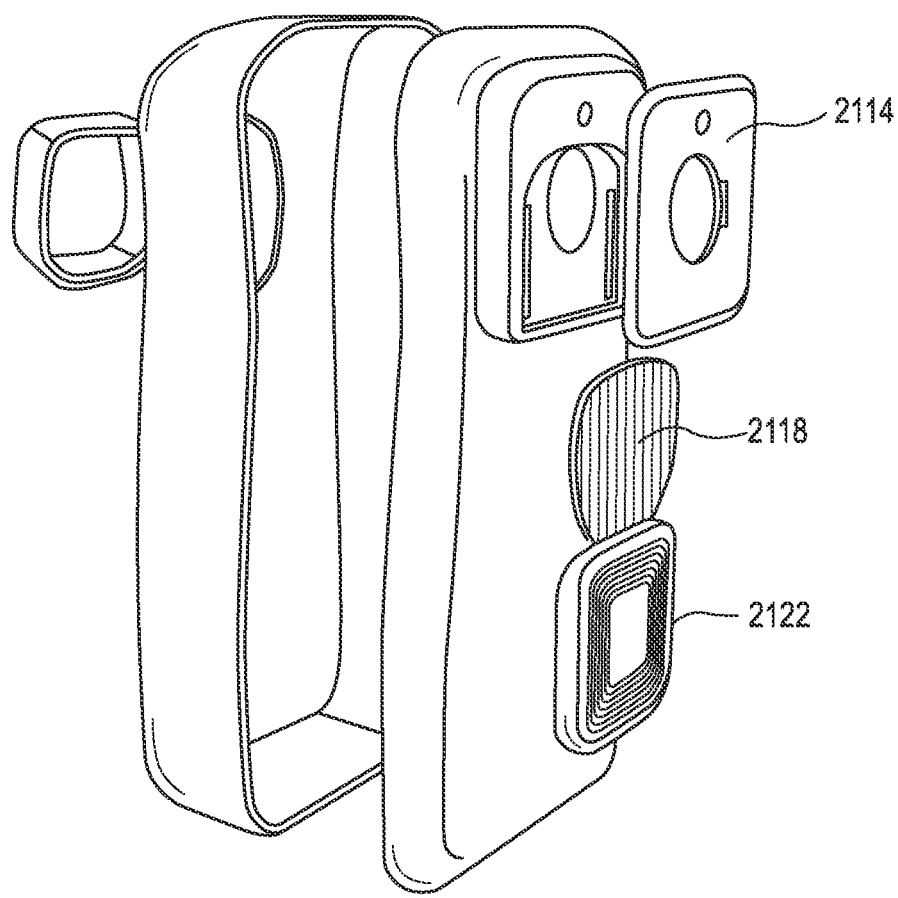
FIG. 21E shows an exploded perspective view of the parts of the housing of the device of FIG. 21A in one implementation.
Figure 21F:
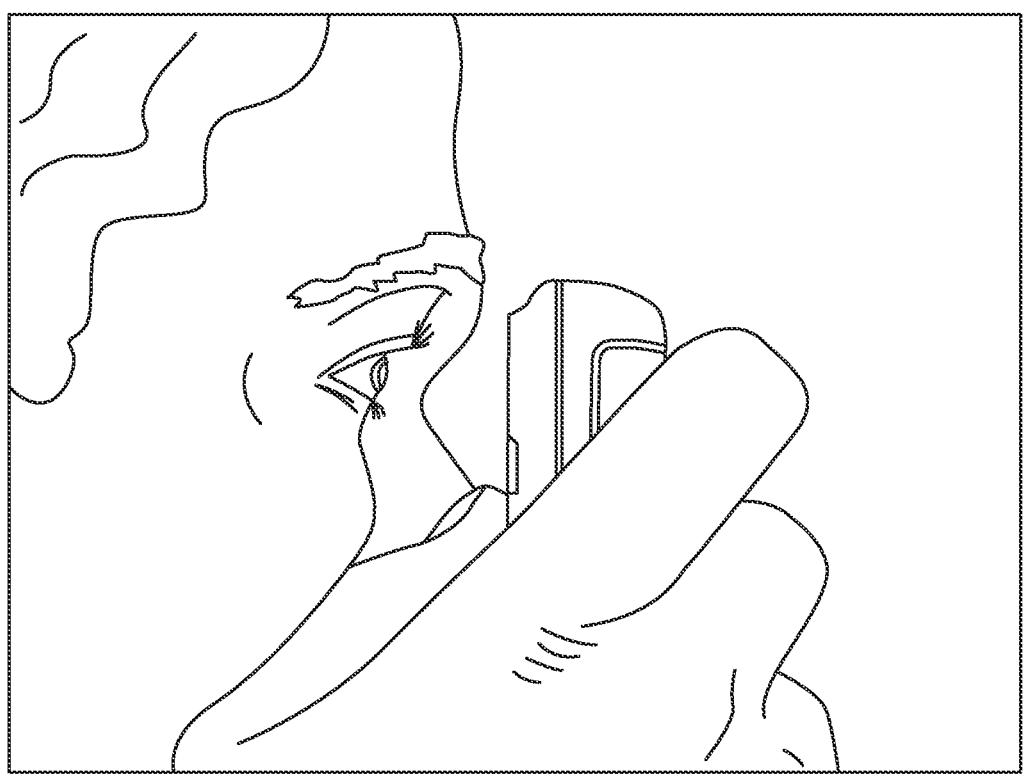
FIG. 21F shows a diagram depicting the device aligned with the eye of a user.

FIGS. 21A-D show another implementation of the housing of the device. The housing 502 formed by components molded from plastic or other suitable material is generally defined by a front portion 2104 and a rear portion 2106. The front portion 2106 includes a fluid delivery area 2108 and an activation mechanism 2110. The fluid delivery area 2108 further defines a delivery aperture 2112 formed through a cover bezel 2114 and through the housing. The fluid delivery area 2108 also includes a multifunction LED 2116 having a function as described earlier with respect to other implementations. The activation trigger 2110 includes an aperture cover plate 2118 and a thumb rest 2120. One or more raised edges 2122 may be formed around the perimeter of the thumb rest 520 to assist with positioning the thumb of a user on the activation trigger 2110. In the implementation shown, the cover plate 2118 and thumb rest 2120 may be formed integrally in one piece or in multiple parts. The cover plate 2118 fits within a slot formed by the front portion 2104 and the cover bezel 2114 (FIG. 5E) and is operable to slide up and down within the slot thereby allowing the cover plate 2118 to seal the delivery aperture 2112 and protect the ejector assembly behind the aperture and internal components from external debris and contamination. Optionally, a back surface of the cover plate 2118 may be coated with material containing silver particles to prevent bacteria from forming in and around the inside of the delivery area. FIG. 21F is a schematic diagram depicting a user aligning the device in the direction of their eye prior to delivering a dose of ophthalmic fluid droplets. The ergonomic design of the device allows the user to place their thumb on the thumb rest located on the device and promotes the thumb to take on a slightly bent position. The proximal phalanx of the thumb may then be placed against the user's cheek bone for steadying the device while the user aligns the delivery aperture with their eye. A multifunction LED, including optionally, a back-lit polished ejector plate, may also aid in alignment. When the user's thumb is placed against their cheek bone, the delivery aperture can be easily aligned at the optimal distance of 2-3 cm from the eye's surface. The user may then locate their index finger on the delivery button, and when ready may depress the delivery button for delivering ophthalmic fluid to the surface of their eye.

Thus, the combination of the position of the thumb rest and the placement of the back of the thumb on the cheek bone provide a natural and repeatable alignment feature and process. Depending on the user's anatomy, a different portion of the thumb or hand may be aligned with an alternate location on the face to affect proper alignment. Alternatively, the device can be held a suitable distance during use, for example, as noted with respect to distance d shown in FIG. 16A. The suitable distance may vary with the type of subject and application. For example, for veterinary subjects, the device may be held a longer distance than for a human subject. Additionally, the device may be held in the palm of the hand and aligned without using the hand or its digits and instead with a spacer or aided by an alignment device as described above. Alternatively, any portion of the hand or its digits can be used to the device and any portion of the hand or its digits may be used to activate the delivery button. By way of example, the device can be held in the hand with the pinky spacing the device from the face and the thumb depressing a delivery button located on the side of the device housing.

During use, the device is held, turned on, aligned, and the delivery button depressed. Turning on the device may manually occur by activation of a physical activation trigger or may occur automatically or in response to a condition, e.g. removal of the device from a docking station. The device may cycle through a cleaning cycle once activated. The properly aligned housing delivers the fluid in the form of the droplet stream to the target.

Figure 22A:
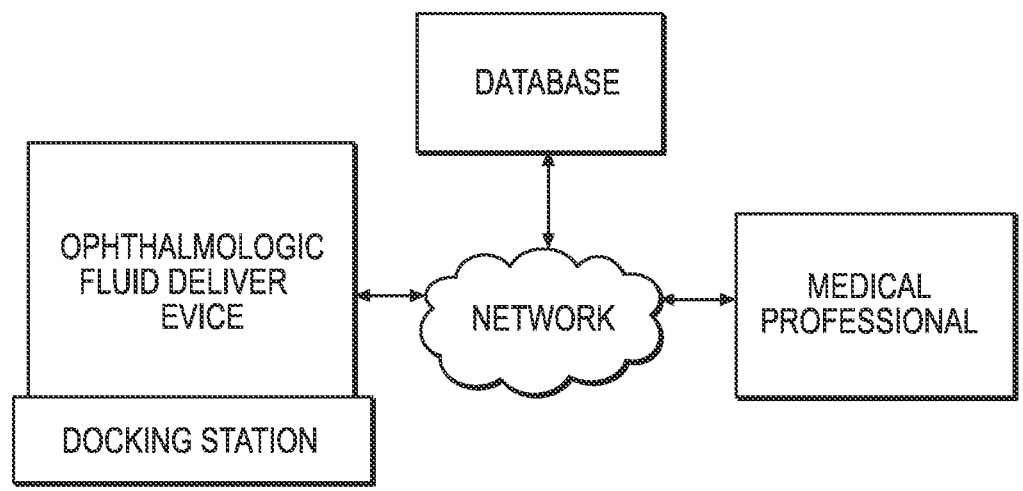
FIG. 22A shows a communications system that includes the device.

FIG. 22A shows a communication system that includes the fluid ejection device. The device may be used in combination with a docking station. Details of this system and a docking station are more fully disclosed in the US Application, entitled "Method and System for Performing Remote Treatment and Monitoring," filed concurrently herewith and incorporated herein by reference.

FIG. 22B shows a block diagram showing a device 2202 and a docking station 2250 in communication. The device 2202 may include a housing 2206, electronics 2208, an ejection mechanism actuator, e.g., piezo 2210, a reservoir 2212, a targeting device 2214, an electronic storage 2216, and an input/output (I/O) interface 2218. The device 2202 also may include an imaging device 2220, a lookup table 2222, a speaker 2224, and an LED 2226.

The housing 2206 may be made from, for example, injection molded plastic or any other suitable, durable, or lightweight material. The housing 2206 may include an opening 2228, a positionable slider 2230, an interface 2232 that sends communications to and receives communicates from the docking station 2250, a stream activator 2234, and a communications interface 2236. The communications interface 2236 sends data to and receives data from a source external to the housing 2206 (see US Application, entitled "Method and System for Performing Remote Treatment and Monitoring," filed concurrently herewith, and herein incorporated by reference in its entirety) to the device 2202, and the docking station 2250. For example, the communications interface 2236 may be in communication with the database or with an input/output device, such as a keyboard.

The opening 2228 may be in the form of an aperture formed through an exterior surface of the housing 2206, and the opening 2228 allows fluid stored in the reservoir 2212 to exit the housing 2206. The opening 2228 may be similar to those explained earlier.

The positionable slider 2230, which may be similar to the thumb slider described earlier. The housing 2206 also includes an interface 2232 configured to receive the connection 2204. The connection 2204 may be, for example, a one-wire, two-wire, or 12C interface. The interface 2232 allows the device 2202 to send data to and receive data from the docking station 2250 over the connection 2204.

The housing 2206 also includes an activation trigger 2234. The trigger may be, for example, a button that protrudes from the exterior surface of the housing 706, a switch, or any other tactile interface that is accessible to a user of the device, such as the switches described above. The trigger 2234 may be on a side of the housing 2206 that is opposite from the side of the housing 2206 that includes the opening 2228 and the slider 2230.

The housing 2206 also may include a communications interface 2236 that is in communication with the electronic storage 2216 and allows retrieval of data stored in the electronic storage 2216 and writing of data to the electronic storage 2216. The interface 2236 may be, for example, a universal serial bus (USB) connection, a serial connection, an Ethernet connection, or any other connection that allows reading and writing of data. Further discussion of these aspects appears in US Application, entitled "Method and System for Performing Remote Treatment and Monitoring," filed concurrently herewith.

The device 2202 includes the electronics 2208, which provide one or more output driver signals to the ejector mechanism actuator or piezo 2210. The piezo 2210 vibrates, moves, or distorts the ejector plate 2202 in response to application of the output signals. The ejector plate 2202 is in contact with fluid stored in the reservoir 2212, and, when the piezo 2210 distorts, fluid from the reservoir 2212 is pulled through one or more openings formed in the ejector plate. In the piezoelectric implementation, the motion of the ejection plate, and in general, the operation of the ejection mechanism, causes a directed stream of droplets to exit the housing 2206 through the opening 2228.

As discussed in greater detail with regard to figures disclosing electronics, the electronics 2208 determine the frequency, voltage, duty cycle, and duration of the output driver signal 2342 that is applied to the piezo 2210. Additionally, the electronics 2208 are programmable such that the characteristics or properties of the output driver signals applied to the piezo 2210 may be adjusted to accommodate changes in the fluid and/or a dosage plan.

Figure 22C:
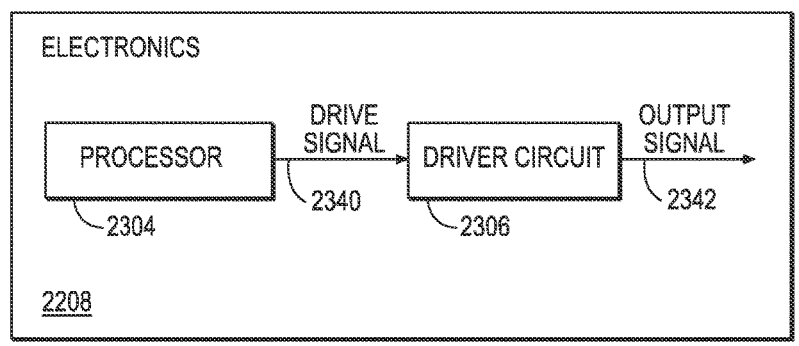
FIG. 22C shows a block diagram of processor and driver circuit.

FIG. 22C includes a processor 2304 and a driver circuit 2306. The processor 2304 provides a excitation signal 2340 to the driver circuit 2306, and the driver circuit 2306 generates an output driver signal 2342 that is applied to the piezo 2210. The properties of the output driver signal 2342 are determined from the properties of the excitation signal 2340. As discussed below, the output driver signal 8232 may include, for example, two or four separate output driver signals.

The reservoir 2212 may be pre-filled with fluid when the device 2202 is manufactured. The device 2202 may be programmed at the time of manufacture of the device 2202. Alternative reservoirs as discussed can be used without limitation.

The device 2202 also includes the targeting device 2214. The targeting device 2214 may assist the user to align the device 2202 with an eye of the subject. The targeting device 2214 may be, for example, an LED that shines in the subject's eye, a reflective or shiny surface that reflects the subject's eye, and/or a CCD camera that images the subject's eye and provides a signal to the electroVINNOnics 2208. The targeting device 2204 may include a reflector to provide the user with an image of his or her eye when the device 2202 is correctly positioned, or may include a light source, such as a low intensity LED, for shining into the user's eye when the device 2202 is correctly positioned. The targeting device 2214 may include a sensor that determines whether or not the subject's eye is open. The targeting device 2214 may include an element that shows a reflection of the subject's eye when the device 2202 is properly aligned with the eye. For example, the ejector plate and/or piezo 2210 may be made from a reflective material that shows a reflection of the subject's eye when the opening 2228 and the piezo 2210 are aligned with the subject's eye. This type of targeting device is helpful for instances where the subject is using the device 2202 to administer a directed stream of droplets to their own eye.

In alternative implementations, all or part of the surface of the ejector mechanism or the housing adjacent thereof may be coated with a reflective layer. A coating layer may be both protective and reflective. Alternatively, the surface may have been formed to be reflective. For example, the surface may be made of stainless, nickel-cobalt, or other reflective material. A surface may have been formed or polished to be reflective. In addition to making the surface reflective, the surface may also be backlit on its surface or around its perimeter. In ophthalmic applications, a reflective surface aids the user in aligning the ejector assembly with the eye.

The device 2202 also includes the electronic storage 2216 and the I/O interface 2218. In addition to storing data such as images of the subject's eye, the electronic storage 2216 stores instructions, perhaps as a computer program, that, when executed, cause a processor included in the electronics 2208 to communicate with other components in the device 2202. The processor may be, for example, a state machine such as an FPGA or an ASIC. The excitation signal 2340 may be generated by a signal generator. Information on the electronic storage 2216 may be accessed through the interface 2218 or the interface 2236 (which communicates with a database), and access to the contents of the electronic storage is controlled, e.g., password restricted to allow certain activities to be conducted by certain medical personnel, e.g., doctors or pharmacists wishing to adjust dosages. Insofar as the computer is Internet enabled, information may be uploaded to via the Internet, e.g. to a server for access by medical personnel to allow progress and proper subject use to be monitored and allow dosages to be adjusted over the Internet, e.g., by uploading revised dosage information to a server by the medical personnel and then pushed to the device via the Internet or downloaded by the user. The device itself may be Internet enabled to allow usage information and image information to be uploaded in real time and new information to be downloaded to the device in real time. Insofar as the device is Internet enabled it may be provided with a user interface, e.g. screen and keyboard or touch sensitive screen.

The input/output interface 2218 provides an interface that allows data and/or commands to be input to the device 2202 and/or read from the device 2202. The input/output interface 2218 may receive data from a device such as a keyboard, a mouse, a communications port, an electronic processor executing on a device separate from the device 2202, or a display. The input/output interface 2218 also may include software that allows communication between the device 2202, the components of the device 2202, and/or an external device. The interface 2218 may provide the user with access to the device 2202 when the device 2202 is plugged into a computer, such as a laptop or palmtop or cellular phone with screen and user input capabilities, through the interface 2218.

The device 2202 also may include an imaging device 2220. The imaging device 2220 may be a charged coupled device (CCD) that is aligned with the opening 2228 such that the imaging device captures an image of the subject's eye through the same aperture that delivers the directed stream of droplets of fluid. In some implementations, the imaging device 2220 is mounted on an external surface of the housing 706 in a location other than the location of the opening 2228. Images collected by the imaging device 2220 may be transferred from the device 2202 through the I/O interface 2218, the communications interface 2236 or 2256, and/or the images may be stored in the electronic storage 2216. The images may be uploaded to the database and stored in association with the subject's medical records, as more fully explained in US Application, entitled "Method and System for Performing Remote Treatment and Monitoring," filed concurrently herewith and herein incorporated by reference in its entirety.

The imaging device 2220 and the electronics 2208 may be operable to control the capture of images during or at selectable times before or after ejection of fluid from the device 2202. In some implementations, the capture of images may be triggered by the user by, for example, depressing a button or the stream activator 2234. For example, saline droplets may be directed from the device 2202 towards the eye to exert a pressure on the cornea and images may be taken to determine the effect. The images may be saved as discussed above.

The device 2202 also may include the look-up table 2222. The look-up table 2222 may be stored on the device 2202, for example, in the electronic storage 2216, or the look-up table may be stored separately from the device 2202, for example, in the database. The look-up table 2222 includes information specific to fluids that may be used in the device 2202. For example, because viscosities of fluid drugs vary, depending on the fluid in the reservoir, the piezo 2210 may require application of output driver signals having a frequency tailored to the fluid in the reservoir. This medication-specific variation may be accounted for by varying the properties, such as the frequency, voltage, and/or duration of the output driver signals produced by the electronics 2208 and applied to the piezo 2210. The look-up table 2222 may include information specific to the medication that is retrieved and used by the electronics 2208 to set the output driver signals.

The look-up table 2222 also may include medication-specific information that relates to the subject's treatment plan. For example, the look-up table may include information specifying that a first medication is to be applied three times a day, while a second medication is to be applied once a day. This treatment plan information is used by the electronics 2208 to determine, for example, when to trigger a reminder alert for the subject based on the type of medication that is placed in the reservoir.

In some implementations, the look-up table 2222 on a specific device 2202 may be edited by a professional, e.g., medical professional to account for changes in the subject's condition. The interface 2236 may be operable to download information, for example, via an external I/O device or directly from the database, perhaps via the Internet. The downloaded information may include one or more of revised dose amounts, revised dose times, and medication type to be dispensed. The device 2202 may be configured such that the electronics 2208 controls the dispensing of medication in response to pre-defined information or the downloaded information.

The device 2202 also may include a speaker 2224 and an illuminator 2226, both of which may be used, in conjunction with the electronics 2208, to provide a perceivable alert to the user of the device 2202. The device 702 may provide other perceivable alerts. For example, the device 2202 may vibrate to attract the user's attention. The device 2202 may produce an audible alarm or enunciator, or visual indicator controllable by the electronics 2208 to provide feedback to the user, for example, visual or audible feedback to indicate when a full dose has been reached. The illuminator 2226 may be an LED or other device that emits visible radiation in response to electrical input.

In some implementations, the illuminator 2226 may include multiple light sources of different frequencies for illuminating the eye, or may include a variable frequency light source, such as light of different colors and frequencies (e.g., red, blue, green, white, infrared (IR), ultraviolet (UV)). The device may include a cobalt blue light (generated, for example, by using a filter) for use with fluorescein to illuminate the cornea for identifying corneal ulcers and scratches. The illuminator 726 may be a radiation source that emits frequencies above 280 nm wavelengths for illuminating the eye. The illuminator 2226 may be operable to pulse the light for different periods of time, for example, 20 nanoseconds (ns) to limit pupil reaction and permit analysis of the eye with different frequency optical detectors, scanners or cameras. The illuminator 2226 may include an adaptive optics chip to perform wavefront correction for clearer images, for example, a MEMS based adaptive optics chip.

The device may also include a fixation source e.g., an LED or LED pattern to define a moving eye-focusing image and assist with pediatric usage. This also serves to move or rotate the eyeball during application of medication to assist in spreading the medication across the corneal surface.

The docking station 2250 includes a housing port 2252 (including without limitation, a docking station) that is configured to receive the device 2202. The housing port 2252 may be recessed such that, when the device 2202 is received by the docking station 2250, the device 2202 is seated securely and is stably held by the docking station 2250. The docking station 2250 also may include a communications interface 2256 that reads and writes data from the docking station 2250 and/or the device 2202. The communications interface 2256 may be, for example, a USB connection, an Ethernet connection, or a serial connection. The docking station 2250 also may include a memory or an electronic storage 2254.

The electronic storage components 2216 and 2254 may be volatile memory, such as RAM. In some implementations, and the electronic storage components 2216 and 2254 may include both non-volatile and volatile portions or components.

Figure 23A:
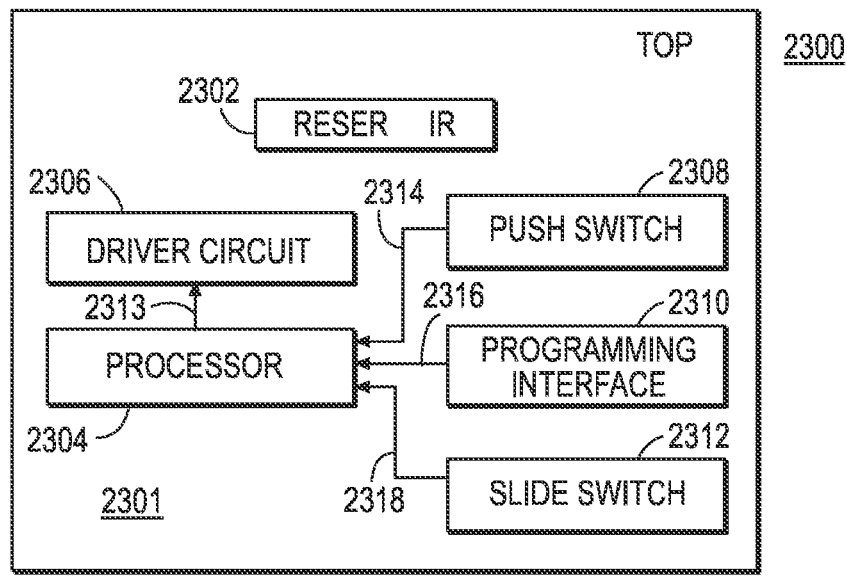
FIG. 23A shows a top view of an example configuration that includes the electronics module.
Figure 23B:
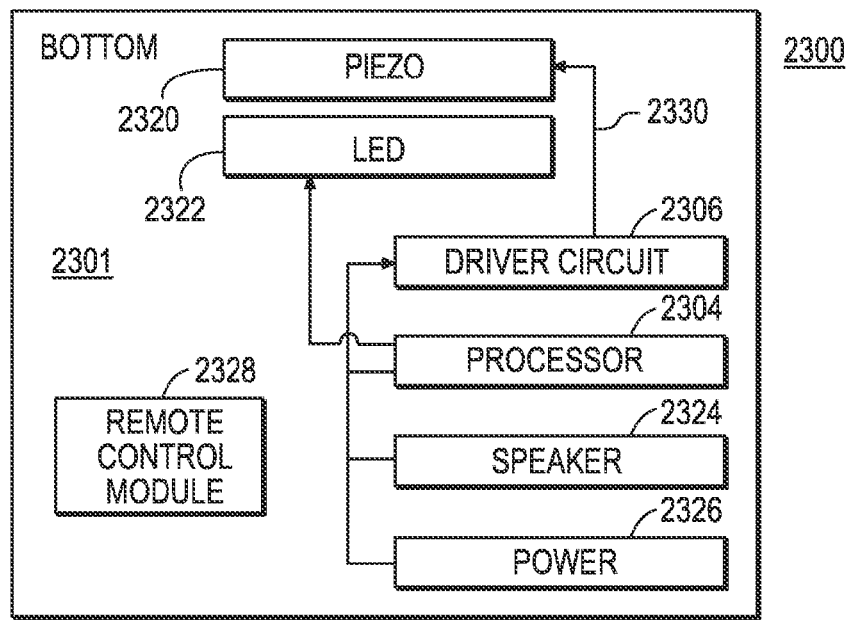
FIG. 23B shows a bottom view of the example configuration that includes the electronics module.

FIG. 23A shows a top view of an example configuration 2300 for the electronics used in the device, and FIG. 23B shows a bottom view of the configuration 800. Although the following description is discussed with respect to the device 2202, the configuration 2300, or a similar configuration may be employed in the device. The configuration may be implemented on a printed circuit board (PCB) sized to fit into a housing that is small enough to be held in a single human hand. The configuration may be implemented on a single PCB board, or on multiple PCB boards. In the example shown in FIGS. 8A and 8B, the configuration is implemented on a single PCB board 2301.

Referring to FIG. 23A, a top view of the configuration 2300 is shown. The top view includes a reservoir 2302, and a processor 2304, the driver circuit 2306, a push switch 2308, a programming interface 2310, and a slide switch 2312. The processor 2304 may be a logic circuit with a free running oscillator designed to control and sequence the signals used to control pulses to the ejector and the formation of the droplets. Alternatively, a field programmable gate array (FPGA), an application specific integrated circuit (ASIC), a complex programmable logic device (CPLD), or a Erasable Programmable Logic Device (EPLD) may be used as the processor. Alternatively, a microprocessor or other programmable processor such as a PIC18F14K50-I/SS microcontroller, available from Microchip Technology, Inc. of Chandler, Ariz., FPGAs and ASICs are generally less costly than microprocessors. Logic circuits and free running oscillators, such as the LM555 used in both the astable and monostable modes, are also less costly and afford high accuracy in signal control. In some implementations, any low-power processor having a voltage range of approximately 2.4 to 6 volts that generates a clock signal and has a sleep or low-power mode may be used as the processor 2304. The driver circuit 806 may be, for example, a LT3572EUF#PBF motor driver, available from Linear Technologies of Milpitas, Calif. Additionally, the device may include a microcontroller with a watchdog timer which monitors the device to ensure proper operation.

The driver circuit 2306 is controlled by, and receives the excitation signal 2340 at a particular frequency from, the processor 2304. Controlling the driver circuit 2306 with the processor may provide a system that has increased flexibility and applicability as compared to a system that relies on a driver circuit alone. For example, controlling the driver circuit with the processor allows the frequency of the output driver signals 2342 produced by the driver circuit to be determined and changed quickly by modifying the properties of the drive signal 2340 produced by the processor. This may allow the device 2202 to adapt to changing subject needs and to operate with the various fluids that may be placed in the reservoir 2302. Additionally, controlling the driver circuit 2306 with the processor 2304 may eliminate the need for a separate potentiometer to control the frequency of the excitation signal 2340. Use of the processor 2304 to control the driver circuit 2306 may allow the electronics 2208 to be reduced in size such that the device 2202 may be held and operated by a single human hand.

The processor 2304 receives data and control signals from a push switch 2308, a programming interface 2310, and a slide switch 2312. The processor may be connected to the driver circuit through an electrically conductive path 2314, such as a copper trace. The push switch 2308, the programming interface 2310, and the slide switch 2312 may be electrically connected to the processor through traces 2314, 2316, and 2318, respectively.

The push switch 2308 is coupled to the activation trigger 2234, the mechanism by which a user of the device 2202 causes release of the directed stream of droplets. The push switch 2308 and a portion of the stream activator 2234 may physically contact each other when the user of the device 2202 presses or otherwise selects the stream activator 2234. In implementations in which the stream activator 2234 is electronic (for example a softkey), the stream activator 2234 may not necessarily be in physical contact with the push switch 2308, rather the stream activator 2234 may provide an electronic indication of selection to the push switch 2308. In response to receiving an indication of activation from the activator trigger 2234, the push switch 2308 generates a spray signal to the processor 2304.

The programming interface 2310 allows the processor 2304 to be programmed to, for example, produce a excitation signal 2340 that has a particular frequency, duration, or time between active states. For example, the processor 2304 may be programmed to generate a excitation signal 2340 having a frequency between about 108 kiloHertz (kHz) and 183 kHz. The programming interface 2310 may be, for example, a 5-pin interface. In some implementations, the programming interface 2310 may be accessible through a graphical user interface (not shown).

The processor 2304 provides the excitation signal 2340 to the driver circuit 2306, and the driver circuit uses the excitation signal 2340 to produce two output driver signals that are applied to the piezo 2320. Each output driver signal 2342 may be a square wave, or approximately a square wave, and each output driver signal 2342 may have approximately the same maximum and minimum voltage. The maximum voltage of the output driver signals may be approximately 20 to 40 volts, and the minimum voltage may be approximately zero (0) volts. The second output driver signal 2342 may be out-of-phase with the first output driver signal, and the first and second output driver signals may be out of phase by approximately 180 degrees.

The slide switch 2312 is coupled to the slider 2330. For example, in implementations in which the slider 2230 is a physical slider, the slide switch 2312 may be physically connected to the slider 2230 such that the slide switch 2312 generates a signal when the slider 2230 is positioned in one or more pre-defined positions on the housing 2206. In some implementations, the slider 2230 may be electronic and may communicate with the slider switch 2312 electronically instead of mechanically. The slider 2330 also may be provided with a metalized surface operable, when the slider 2330 is moved into the open position, to bridge the gap between two metal contacts, thereby defining a slide switch. The slide switch 2312 may generate a signal when the slider 2230 is moved to a position that reveals (or uncovers) the opening 2228. This signal may be referred to as an initiation signal. The slide switch 2312 may generate another signal when the slider 2230 is moved from that position. Signals generated by the slide switch 812 are provided to the processor 2304.

Referring to FIG. 23B, a bottom view of the configuration 2300 is shown. The bottom view is shown as the mirror image of the top view of FIG. 23A. The bottom view shows a piezo 2320, an LED 2322, the driver circuit 2306, the processor 2304, a speaker 2324, a power module 826, and a remote control module 2328.

The piezo 2320 holds and/or is in contact with the ejector plate 1602 (FIG. 16A) that contacts a fluid held in the reservoir 2302, and the piezo 2320 receives the output driver signals from the driver circuit 2306 through a conductive path 2330. The piezo 2320 moves, vibrates, distorts and/or changes shape in response to application of the output driver signals 842 from the driver circuit 2306.

In one implementation, the piezo 2320 is mounted on the printed circuit board (PCB) 2301 and contacts a conductive surface (not shown) on the PCB board 2301. The conductive surface may be stainless steel. In some implementations, the conductive path 830 is a discrete wiring, not integrated with the board 2301, that connects the piezo 2320 to an output of the driver circuit 2306. In some implementations, the conductive path 2330 is a trace made directly on the PCB board 2301. In these implementations, a conductive material is placed between the piezo 820 and the o-ring and reservoir 2302. The conductive material may be, for example an elastomer or "Zebra strip." In these implementations, the discrete wire is eliminated and the output driver signal 2342 from the driver circuit 2306 is provided to the piezo 2320 by a conductive trace formed directly on the PCB board 2301. The piezo 2320 may be aligned with the opening 2228 to allow the directed stream of droplets to exit the device 2202.

In some implementations, the configuration 800 includes a second piezo that is coupled to the reservoir that is mounted on the top of the PCB board. In this implementation, the driver circuit 2306 is configured to generate four output driver signals 2342 to drive the two separate piezos. The second piezo may be mounted directly to the surface of the reservoir 2302 such that the reservoir 2302 vibrates with the second piezo. This vibration may help to ensure that the fluid in the reservoir 2302 remains in a fluid state and to help prevent the formation of crystals and other solid particles in the reservoir 2302. In the case of medications provided as a suspension, the vibration may be operable to churn up the medication.

The LED 2322 receives power from the power module 2326 and a signal to turn ON or OFF from the processor 2304. The processor 2304 also provides a signal to the speaker 2324 to turn ON or OFF. The configuration 2300 includes a remote control module 2328 that allows for remote configuration and/or control of the processor 2304. The power module 2326 may be one or more batteries. For example, the power module 2326 may include three batteries.

Figure 24:
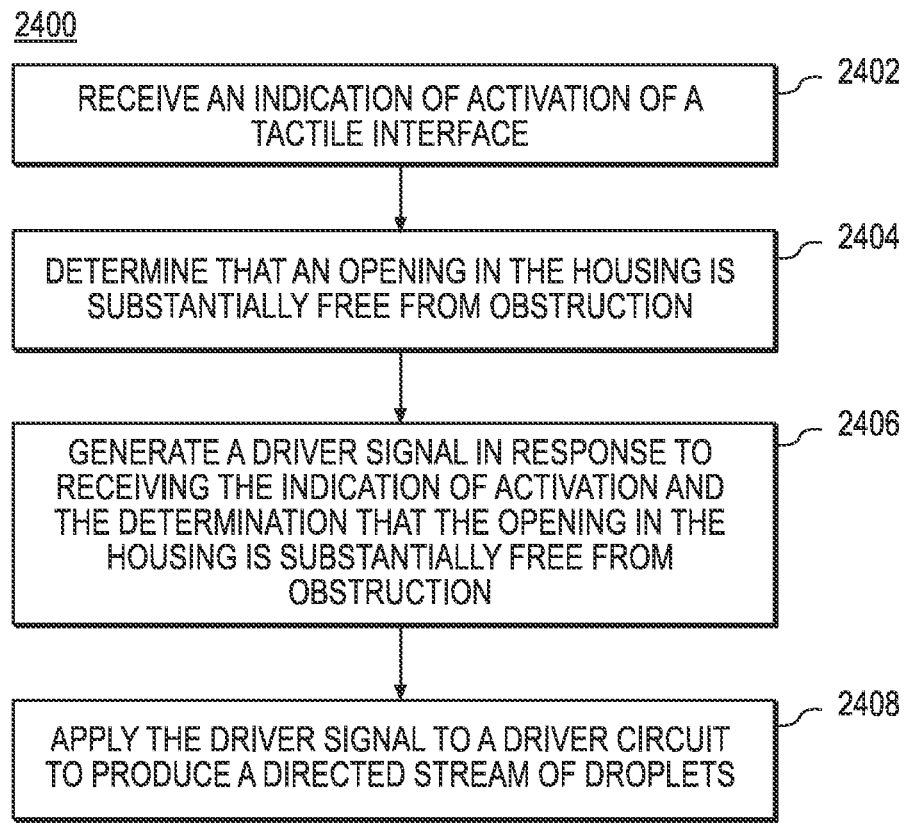
FIG. 24 shows an example process for operating the device.

FIG. 24 shows an example process 2400 for operating a device that delivers a directed stream of droplets to a subject's eye. The process 2400 may be performed using, for example, the device. The process 2400 may be performed by the electronics 2208 or the processor 2304. The process 2400 may be performed by the processor 2304 in conjunction with the driver circuit 2306. An indication of activation of a tactile device is received 2402. The tactile device may be, for example, the stream activator 2234, and the indication of activation may be the spray signal that is generated by the push switch 2308 when the stream activator contacts the push switch 2308 physically or interacts with the push switch 2308 electronically. The indication of activation results from a user of the device 2202 specifying that a directed stream of droplets of fluid is to be released from the device 2202.

Whether an opening in the housing is substantially free from obstruction is determined 2404. The directed stream of droplets is released from the device 2202 when the slider 2230 is in a position that reveals, rather than covers, the opening 2228. When the slider 2230 is positioned in a position on the housing that reveals the opening 2228, the slide switch 2312 generates a signal that is provided to the processor 2304. If this signal has not been generated, the opening 2228 is not substantially free from obstruction. If the signal has been generated, the opening 2228 is substantially free from obstruction such that a directed stream of droplets may be released from the device 2202.

An excitation signal is generated in response to receiving the indication of activation and determining that the opening in the housing is substantially free from obstruction 2406. The excitation signal 2340 is applied to the driver circuit 2306, which in turn generates two voltage signals (output driver signals) that are applied to the piezo 2320 (or piezo 2210) to cause the piezo and the ejector plate 1602 attached to the piezo to vibrate, move, or otherwise distort. The motion of the ejector plate 1602 draws fluid from the reservoir 2302 and through one or more holes in the ejector plate, creates a directed stream of droplets of fluid for delivery to the subject's eye. The excitation signal 2340 may be a square wave having a frequency of about 95 kHz to 183 kHz. The excitation signal 2340 is applied to the driver circuit 2306, and the driver circuit 2306 produces two square wave output driver signals that are 180° out of phase with each other and that are applied to the piezo 2320. The voltages of the square wave output driver signal 2342 may be, for example, 20 to 40 volts, and the frequency of each output driver signal 2342 may be between about 95 kHz to 183 kHz.

Figure 25:
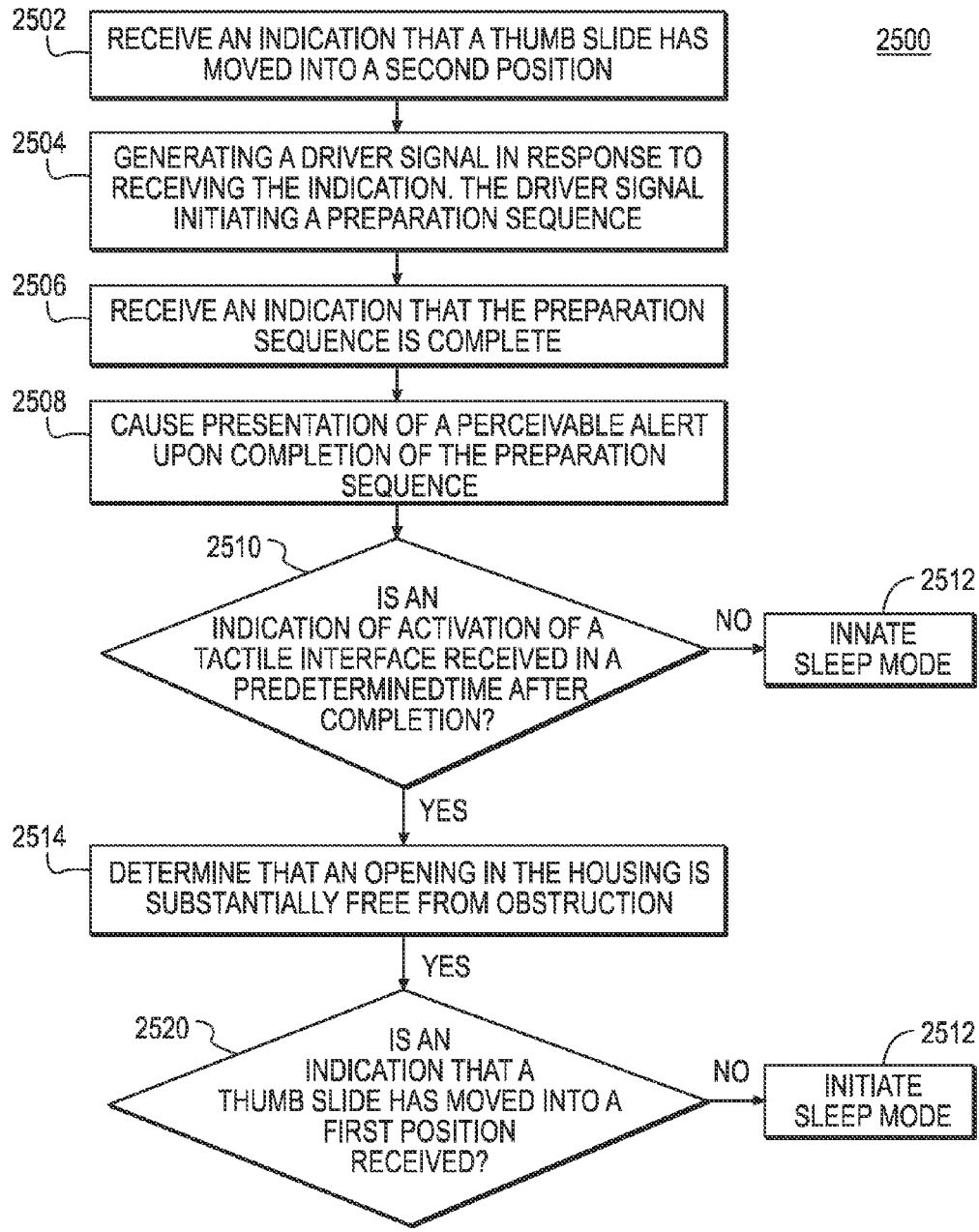
FIG. 25 shows another example process for operating the device.

FIG. 25 shows another example process 2500 for operating a device that directs a stream of droplets of fluid to a subject's eye. The process 2500 may be performed using, for example, the device. The process 2500 may be performed by the electronics 2208 or the processor 2304. The process 2500 may be performed by the processor 2304 in conjunction with the driver circuit 2306.

An indication that a thumb slide has moved into a second position is received (2502). The thumb slide may be a slider similar to the slider 2230, and the second position may be a location on the surface of the housing 2206 that reveals the opening 2228 such that the directed stream of droplets may exit the device 2202. The indication of that the slider 2230 has moved may be a signal generated by the slide switch 2312 in response to the slider making mechanical or electrical contact with the slide switch 2312. A excitation signal 2340 is generated in response to receiving the indication (2504). The excitation signal 2340 may be generated by the processor 2304, and the excitation signal 2340 may be a signal that controls the driver circuit 2306 to produce output driver signals that drive the piezo to perform a preparation sequence. The preparation sequence may be referred to as an initiation sequence, a purge cycle, or a cleaning cycle.

The preparation sequence causes the device 2202 to produce one or more directed streams of droplets that are not intended for placement in the subject's eye. Rather, the one or more streams produced in the preparation sequence flush out the barrier, the hole in the barrier, the reservoir, and other internal components of the device 2202. The preparation cycle may reduce or eliminate contaminants and residues that may accumulate in the device 2202 between uses. In some implementations, about 8 to 10 directed streams of droplets are produced during the preparation sequence. Although the directed stream of droplets released during the preparation sequence is not intended for placement in the subject's eye, the medication in the reservoir is used as the fluid during the preparation cycle to clean and/or prepare the device for use.

In some implementations, the drive signal 2340 applied to the driver circuit 2306 causes the driver circuit to produce two output driver signals with a waveform having a cycle that lasts for a total of about 50 milliseconds, and for about 30 milliseconds of the cycle while the output driver signal 2342 is ON, and for about 20 milliseconds while the output driver signal 2342 is OFF (that is, essentially no output driver signal 2342 is applied to the piezo). The preparation cycle may include applying these output waveforms to the piezo for about 8 to 10 cycles of the waveform. When the output waveform is ON, the piezo vibrates and draws fluid from the reservoir through the barrier to clean the components of the device 2202.

An indication that the preparation sequence is complete is received 2506, and a perceivable alert is presented upon completion of the preparation sequence 2508. The perceivable alert may be, for example, the LED 2322 turning ON. The alert lets the user of the device 2202 know that the device 2202 is ready for use. If an indication of an activation of a tactile interface is not received within a predetermined amount of time after the completion of the preparation sequence, a sleep mode is initiated 2512. If an indication of an activation is received within the predetermined amount of time, it is determined whether the opening in the housing is substantially free from obstruction such that a directed stream of droplets may exit the housing 2206.

If an indication that the thumb slide has moved into a first position is received, then the sleep mode is initiated 2512. The first position may be a position in which the thumb slide covers the opening in the housing. If an indication that the thumb slide has moved into the first position has not been received, the device 2202 remains ready to receive an input from the user until a predetermined amount of time has elapsed. After the predetermined amount of time has elapsed, the sleep mode is initiated.

The processor 2304 may be programmed to dispense only a predetermined number of dosages, such as 30 dosages, 60 dosages, or 180 dosages, and additional activation of the tactile interface does not produce a directed stream of droplets.

Other alternative implementations are also contemplated. By way of example, in one implementation, ejection plates are created by precise micro fabrication techniques. A size of microspheres ejected from such a plate will vary in volume according to the magnitude of plate motion. The frequency of the plate motion is influenced by the frequency of an electrical voltage (typically a square wave) that drives the piezoelectric actuator attached to the ejector plate. Typically the actuating frequency will be in the range of 50 kHz to 200 kHz and will have a duration great than about 0.1 milliseconds.

Drug volume per dose is calculated from the diameter of the ejected spheres, number of holes in the plate, frequency of vibration, number of voltage cycles per ejection per hole, and length of time the plate is vibrated. For example an ejection plate having 1000 holes that are 20 microns in diameter may eject spheres about 40 microns in diameter. If a sphere ejects from each hole about once per ten cycles then a 100 kHz vibration from the piezoelectric element will eject about 100,000/10 spheres per hole per second or about 10,000,000 spheres per second when all 1000 holes are ejecting fluid. If each sphere is 40 microns in diameter then the ejector plate will dispense about 10,000,000*4/3*pi*((40e−6)/2)^3 cubic meters per second or about 10,000,000*4/3*pi*((40e−3)/2)^3=335 microliters per second. If the plate is actuated for 20 milliseconds then about 6.5 microliters of drug are ejected.

Without being limited by theory, sphere size and velocity are related to the amplitude and frequency of the waveform voltage driving the piezoelectric element. In part, this is because magnitude of the ejector plate motion and piezoelectric motion is related to frequency of the driving signal. Magnitude of the piezoelectric motion is related to the voltage of the applied voltage. Ejection velocity is also dependent on the frequency and magnitude of the applied voltage. In some implementations, spheres are not effectively ejected except near resonant frequencies or their harmonics. In an implementation, spheres ejected at these frequencies will be optimized for maximum speed and volume. Unfortunately, variation in manufacture of piezoelectric elements can cause resonant frequencies to vary about 10% from the average. This variation results in each dispense unit needing a slightly different voltage or frequency to achieve the same dispense velocity and volume. Each unit can be tuned during manufacture for a specific frequency. The oscillation of the piezoelectric element is highly dependent on frequency. Therefore, optimization of frequency is a often needed and control of the frequency of a square wave can be accomplished by changing the frequency of the internal square wave generator (typically a microprocessor or FPGA).

In certain implementations of a portable device, voltage and power applied to the piezoelectric element can be limited by breakdown voltages of electrical components and total battery energy. Voltage can be minimized to reduce power consumption while still achieving optimal ejection of spheres. Tuning the frequency slightly off the resonant frequency allows control of the ejection velocity and plume shape for a given applied voltage. Similarly total mass ejected per dose is controlled by the duration of ejection. Thus a final tuning of driving frequency and pulse time is needed to set ejection velocity and dose volume.

One implementation described here is a device and method for tuning the ejection velocity and dose size for a portable ophthalmic dispenser. In an implementation of this a small target plate with an associated weighing mechanism and a vision system that observes the region between the dispenser and target plate. A test fixture controller dispenses the dose for a fixed time and receives the weight and velocity of the dispensed dose. A controller calculates appropriate modifications in the ophthalmic delivery device. A ophthalmic dispenser has a programmable internal controller with static memory (such as EEPROM) to store optimized parameters.

A vision system will measure the velocity of the dispense. Typical dispense velocities are in the range of 0.5 to 10 meters per second with typical time of flight of 4 to 80 milliseconds travelling a distance of 4 cm. Thus a camera with a frame rate faster than 100 frames per second and ideally 10,000 frames per second would measure the leading edge of a dispense as it travels from the dispenser to the weighing station. Accuracy of measuring the front edge of the droplets depends upon an effective illumination source, effective optics, and the camera's resolution.

In one implementation operation, a dispenser will be placed in the tuning station in a rigid jig (or brought to the test area in a jig) with electrical connections to the dispenser. A dose will be dispensed towards the target about 4 cm away as the vision system measures the velocity of the front edge of the ejected droplets. Then the target will be weighed. A controller then calculates the dispense volume and velocity. Typically dispenses will be done at multiple frequencies to determine the optimal dispense frequency for correct droplet velocity. Dosage per dispense will be measured by the weighing system at this frequency and then dispense time will be set to a value that gives the correct dosage.

At appropriate times the dispense fluid is cleaned from the target with a blast of air followed by another weighing to tare the system. For accurate dose measurement multiple dispenses may be done to increase the total mass measured. Then, an average can be taken to determine the mass of a single dose.

Additionally, a vision system can be used to verify the width of the dispense plume and even infer droplet size according to the degree to which the droplets are carried around the target by the airflow. This data can be collected in one or two directions (for example, from above or from the side) to verify aim of the dispenser plate if needed. Similarly, a vision system that observes droplet flight from the side can infer dispense velocity and droplet size from the amount that the dispense falls below the target. With higher dispense velocities the vertical position of the droplets will change less.

In order for this system to work, each portable device may have an externally programmable memory to hold the calibration constants or formula for piezoelectric frequency and pulse duration. For consumer and particularly prescription applications, each unit can, if desired for that implementation, store the number of doses it is allowed to dispense. Knowing the volume of the fluid is allows for overfilling, which can optionally use for calibration sprays and cleaning sprays which may occur each time the unit is opened. In one implementation a entire ejector plate wetted for a full-dose dispense. A full wetting requirement may result in excess drug that can be stored in the dispenser so that at the end of user dosing there will be drug left in the dispenser.

In one implementation, number of doses ejected can be restricted both for the consumer to prevent partial doses being used and for the supplier of the device so that per dose is accurately accomplished. For example, if a unit was 20% overfilled then the consumer might buy 20% fewer units on an annual basis in the case of long-term use of the device.

In one implementation, along with calibration constants and dose limits, the memory may be programmable to allow the same unit to dispense different sized doses in the case where a smaller person or child should receive smaller doses of the drug. Similarly, in cases where the unit should alert the user if a dose is overdue, as in the case of a glaucoma medication where regular application of the drug is key to minimizing damage by the disease, medication intervals and even an internal clock might be set. For example, during the day doses might be required every four hours but no doses are required from 9 pm to 6 am when the person is sleeping. In one implementation, a point of calibration of the dispense system or later during packaging or prescription sales the user constants might be downloaded to the device.

Many implementations of the invention have been disclosed. This disclosure contemplates combining any of the features of one implementation with the features of one or more of the other implementations. For example, any of the ejector mechanisms, or reservoirs can be used in combination with any of the disclosed housings or housing features, e.g., covers, supports, rests, lights, seals and gaskets, fill mechanisms, or alignment mechanisms. Further variations on any of the elements of any of the inventions within the scope of ordinary skill is contemplated by this disclosure. Such variations include selection of materials, coatings, or methods of manufacturing. Any of the electrical and electronic technology can be used with any of the implementations without limitation. Furthermore, any networking, remote access, subject monitoring, e-health, data storage, data mining, or internet functionality is applicable to any and all of the implementations and can be practiced therewith. Further still, additional diagnostic functions, such as performance of tests or measurements of physiological parameter may be incorporated into the functionality of any of the implementations. Performance of a glaucoma or other ocular tests can be performed by the devices as a part of their diagnostic functionality. Other methods of fabrication known in the art and not explicitly listed here can be used to fabricate, test, repair, or maintain the device. Furthermore, the device may include more sophisticated imaging or alignment mechanisms. For example, the device or base may be equipped with or coupled to an iris or retina scanner to create a unique id to match a device to the user, and to delineate between eyes. Alternatively, the device or base may be coupled to or include sophisticated imaging devices for any suitable type of photography or radiology.

To assist in understanding the present invention, the following Example is included. The experiments described herein should not, of course, be construed as specifically limiting the invention and such variations of the invention, now known or later developed, which would be within the purview of one skilled in the art are considered to fall within the scope of the invention as described herein and hereinafter claimed.

EXAMPLE

An implementation of the disclosure may be carried out through this Example. Although many arrangements are possible, one implementation uses an annular PZT piezo attached directly to a circular 80 microns thick Ni—Co ejector plate, having a diameter of 0.5 cm. The ejector plate contains eighty-nine 30 microns cylindrical holes bored through the center with a 380 microns center-to-center distance between adjacent holes. A 60 Vpp amplitude square wave is applied to the piezo at the resonant frequency (108.0 kHz) causing the ejector plate to oscillate at approximately the same frequency.

When operating with these parameters, the device produces droplets with a size distribution in which the median diameter is 55 microns. In this example, it is assumed that the ideal range for the device is 3.0 cm orthogonally from the plane of the target. If the target has a bottom-to-top target diameter of 8.0 mm, then the average distance that a droplet could fall due to gravity before leaving the target is 4.0 mm. The terminal velocity for a 55 microns water droplet is 0.09 m/s. Therefore it takes at least 0.044 s to fall 4 mm. Assuming that the average horizontal velocity of a droplet is ½ the initial velocity, the minimum initial velocity needed to propel the droplet to a target 3.0 cm away in 0.44 s is 1.4 m/s.

Droplets with a diameter of 55 microns have an evaporation time of approximately 3 seconds. Therefore, a particle traveling at the minimum velocity needed to reach the eye would still contain greater than 99% of its initial volume upon impact with the eye. See, e.g., FIGS. 27 and 28.

Without accounting for entrained air effects, the momentum to drag force ratio (relaxation time) of this median sized particle would be 0.0093 s, leading to a theoretical stopping distance of 9.3 mm. However entrained air reduces the drag force on droplets, increasing the effective range by up to one order of magnitude.

Measurement and analysis of particle diameter was performed with a Malvern Spraytec instrument. This system uses a 632.8 nm laser collimated to a 10 mm diameter beam. When the laser interacts with particles in its path, light is scattered at various angles depending on the droplet size. A lens focuses the scattered light onto photodiode detector elements. The control software subtracts electrical and optical background noise, applies a multiple scattering correction filter, and then calculates the droplet size distribution as a function of time.

Mass deposition experiments were performed with a 20 MHz BK Precision 4040A function generator, a NF Electronic Instruments 4025 high speed power amplifier/bipolar power supply, and an Ohaus Pioneer PA214 digital scale (210 g capacity×0.1 mg resolution). Glass slides (7.5 cm×7.5 cm) were used to collect droplets ejected from the Corinthian Ophthalmic drug delivery invention. These large slides are important to observe the effect of entrained air on mass deposition. An Edmund Optics 36 inch dovetail optical rail was used to vary the mass deposition distance while maintaining straight line accuracy.

Droplet size distributions were measured with the Malvern Spraytec instrument and software. A droplet generating device was maintained at a constant distance of 3.0 cm from the center of the collimated laser beam and sprayed horizontally into the beam. The function generator was used to drive the high speed power amplifier using pulse-width modulation. The high speed power amplifier produced a square wave with 108.0 kHz frequency, pulse width of 0.150 s, 50% duty cycle, and 60 Vpp amplitude, thereby driving the piezo at its resonant frequency. The Malvern Spraytec triggered to begin measurements when laser transmission dropped below 98%.

Dose effectiveness measurements were performed by observing the mass deposition on the glass slide at distances of 0.0-6.0 cm from the ejector plate. This experiment was performed on 5 different ejector plate hole sizes.

The graphs are normalized to 100% mass deposition, and plotted as a function of distance and median particle diameter as measured by the Malvern Spraytec device (FIGS. 29A and B). FIG. 29A shows how the 10 and 17 microns particles only delivery a partial dose (68-85%) at distances of 3 cm. However, the 32, 56, and 70 microns particles deliver 92-99% of the dose at 3 cm. At a larger distance of 6 cm, the 10 and 17 microns particles appear to only deliver 21-51%, while the 32, 56, and 70 microns particles appear to deliver 70-84% of the original dose. This figure suggests that droplet size is a relevant variable to consider when attempting to deliver ophthalmic fluids with an ejector-type delivery device.

Droplets with insufficient mass will have a low momentum to drag force ratio as shown in equation 3. These droplets will create more entrained air relative to their diameter during their time of flight, because they have a larger surface to volume ratio. When these smaller droplets near the eye, they have an insufficient momentum to overcome the entrained air effect described above, and consequently are often deflected. Small droplets also have a shorter stopping distance. This factor contributes to their rapid deceleration before they reach the target. An evaporation rate is also higher for the droplets at the 17 microns diameter threshold. A higher evaporation rate helps to compound the problems of stopping distance, air entrainment, and momentum to drag force ratio.

Droplet diameters and mass deposition rates are measured at various distances. Droplets with diameter greater than or equal to 32 microns have a noticeably higher percentage of mass deposited. Particles with diameters less than or equal to 17 microns appear did not deposit significant mass over a wide range of distances. Droplets with diameters greater than or equal to 32 microns perform deposited mass at higher levels seem for diameters equal or less than 17 microns. See, for example, FIGS. 29A and B.

In an implementation, a hand-held, portable ophthalmic dispenser typically is held about 3 cm from the eye as it creates fluid microspheres or micro droplets that travel to the eye of the user. Microspheres of the drug are formed and launched as a piezo material vibrates an ejection plate on the dispenser in a precise pattern of frequency and duration. A piezo material changes shape as a voltage is applied across it. A shape change is mechanically linked to vibrate the ejection plate. Size and velocity of the microspheres is critical so that spheres are not too small and slow moving that they fail to ready the eye. Similarly, quantities and mass of the spheres is important to maintain a correct dosage of drugs to the eye. Ejection plates are created by precise micro fabrication techniques. Microsphere diameter is related to diameter of holes in the ejection plate. Ejection plates will typically have hundreds of holes in the plate, all fabricated to have the same diameter with a nominal diameter typically between 15 microns and 60 microns.

In one implementation, the size of the microspheres ejected from such a plate will vary in volume according to the magnitude of plate motion. The frequency of the plate motion is determined by the frequency of an electrical voltage (typically a square wave) that actuates the piezo actuator attached to the ejector plate. Typically, the actuating voltage will be in the range of 100 kHz to 150 kHz and will have a duration of 10 milliseconds to 100 milliseconds per dose.

In one implementation, drug volume per dose is calculated from the diameter of the ejected spheres, number of holes in the plate, frequency of vibration, number of voltage cycles per ejection per hole, and length of time the plate is vibrated. For example, an ejection plate having 1000 holes that are 20 microns in diameter may eject spheres about 40 microns in diameter. If a sphere ejects from each hole about once per ten cycles then a 100 kHz vibration from the piezo will eject about 100,000/10 spheres per hole per second or about 10,000,000 spheres per second from all 1000 holes. If each sphere is 40 microns in diameter, then the ejector plate will dispense about 10,000,000*4/3*pi*((40e−6)/2)^3 cubic meters per second or about 10,000,000*4/3*pi*((40e−3)/2)^3=334 microliters per second. If the plate is actuated for 40 milliseconds, then about 13 microliters of drug are ejected.

While not to be limited by them, sphere size and velocity are related to the magnitude and frequency of the voltage applied to the piezo. In part, this is because magnitude of the ejector plate motion and piezo motion is related to frequency of the driving signal. Magnitude of the piezo motion is directly related to the voltage of the applied voltage. Ejection velocity is also dependent on the frequency and magnitude of the applied voltage. It has been found that the spheres are not ejected except in a fairly narrow range of frequency band with optimums for maximum speed and volume. Unfortunately, variation in manufacture of piezos causes this optimum to vary about 10% among a batch of piezos. This variation results in each dispense unit needing a slightly different voltage frequency to achieve the same dispense velocity and volume. Thus, each unit must be tuned during manufacture for a specific frequency. Typically, frequency rather than voltage is tuned due to the increase in circuit complexity and cost associated with having voltage control. On the other hand, control of the frequency of a square wave is accomplished by changing the frequency of the internal square wave generator (typically a microprocessor or FPGA).

In one implementation, in a portable device, voltage and power applied to the piezo is limited by breakdown voltages of electrical components and total battery energy. Thus, tuning for optimum ejection of spheres is required to achieve good ejection with minimum and maximum voltages. Tuning frequency slightly off the optimum allows control of the velocity of ejection for a given applied voltage. Similarly, total mass ejected per dose is controlled by the duration of ejection. Thus, a final tuning of driving frequency and driving time is needed to set ejection velocity and dose volume.

In one implementation, described here is a device and method for tuning the ejection velocity and dose size for a portable ophthalmic dispenser.

In one implementation, a small target plate with an associated weighing mechanism and a vision system that observes the region between the dispenser and target plate and a test fixture controller that initiates dispenses from the dispenser, receives the weight and velocity of the dispensed dose and calculated appropriate modifications to dispense constants in the ophthalmic delivery device. An ophthalmic dispenser has an externally programmable, internal controller with static memory (like EEPROM) to receive and store these constants.

In one implementation, the vision system will measure the velocity of the dispense. Typical dispense velocities are in the range of 0.5 to 5 meters per second or times to transit 5 cm of 10 to 100 milliseconds. Thus, a camera with a frame rate faster than 100 frames per second and ideally about 1000 frames per second would measure the leading edge of a dispense as it travels from the dispenser to the weighing station. Obviously, accuracy of measuring the front edge of the droplets depends upon an effective illumination source that is part of the vision system.

In one implementation, a dispenser will be placed in the tuning station in a rigid jig (or brought to the test area in a jig) with electrical connections to the dispenser. A dose will be dispensed toward the target about 3 cm away as the vision system measures the velocity of the front edge of the ejected droplets. Then, the target will be weighed. The controller then calculates the dispense volume and velocity. Typically, dispenses will be done at multiple frequencies to determine the optimal dispense frequency for correct droplet velocity.

Dosage per dispense will be measured by the weighting system at this frequency and then dispense time will be set to a value that gives the correct dosage.

In one implementation, the dispense target approximates the area of an eye. At appropriate times, the dispense fluid is cleaned from the target with a blast of air followed by another weighing to tare the system. For accurate dose measurement, multiple dispenses may be done to increase the total mass measured.

In one implementation, a vision system can be used to verify the width of the dispense plume and even infer droplet size according to the degree to which the droplets are carried around the target by the airflow. This data can be collected in one or two directions (for example, from above or from the side) to verify aim of the dispense plate if needed. Similarly, a vision system that observes droplet flight from the side can infer dispense velocity and droplet size form the amount that the dispense falls below the target. With higher dispense velocities, the vertical position of the droplets will change less.

In one implementation, in order for this system to work, each portable device must have an externally programmable memory to hold the calibration constants for piezo frequency and duration. Additionally, for consumer and particularly prescription applications, each unit must be able to store the number of doses it is allowed to dispense. This is necessary because each unit will have to be slightly over-filled both to allow for calibration sprays and cleaning sprays which may occur each time the unit is opened. Furthermore, by the nature of a multi-hole ejector, it is necessary to have the entire ejector plate wetted for a full-dose dispense. The full wetting requirement will require that excess drug will have to be stored in the dispenser so that at the end of user dosing, there will be drug left in the dispenser.

In one implementation, the number of doses ejected can be restricted both for the consumer to prevent partial doses being used and for the supplier of the device so that per dose is accurately accomplished. For example, if a unit was 20% overfilled, then the consumer might buy 20% fewer units on an annual basis in the case of long-term use of the device.

In one implementation, along with calibration constants and dose limits, the memory may be programmable to allow the same unit to dispense different sized doses in the case where a smaller person or child should receive smaller doses of the drug. Similarly, in cases where the unit should alert the user if a dose is overdue, as in the case of a glaucoma medication where regular application of the drug is key to minimizing damage by the disease medication intervals and even an internal clock might be set. For example, during the day, doses might be required every 4 hours, but no doses are required from 9 pm to 6 am when the person is sleeping.

In one implementation, at the point of calibration of the dispense system, or later during packaging or prescription sales, the user constants might be downloaded to the device.

Although the foregoing describes various embodiments by way of illustration and example, the skilled artisan will appreciate that various changes and modifications may be practiced within the spirit and scope of the present application.

U.S. application Ser. No. 13/184,446, filed concurrently herewith, entitled "Ophthalmic Drug Delivery" and U.S. application Ser. No. 13/184,468, filed concurrently herewith, entitled "Method and System for Performing Remote Treatment and Monitoring" are also each herein incorporated by reference in their entireties.

What is claimed is:

1. A method of delivering fluid to an eye of a subject as an ejected stream of droplets, comprising: generating the ejected stream of droplets via a droplet generating device, the droplet generating device including an ejector plate, the ejector plate including a plurality of openings formed therein, a fluid delivery area adjacent the ejector plate, and a piezoelectric actuator coupled to the ejector plate, the piezoelectric actuator being coupled to the ejector plate to oscillate the ejector plate; wherein the ejected stream of droplets is generated by actuating the piezoelectric actuator to oscillate the ejector plate, the droplets being ejected through the plurality of openings in the ejector plate; and delivering the ejected stream of droplets to the eye of the subject, wherein the ejected stream of droplets have an average ejected droplet diameter of 25 microns to 75 microns and an average initial droplet ejecting velocity of 2 m/s to 20 m/s, the ejected stream of droplets being generated to deliver a dose of fluid to the eye with a duration of delivery of between 25 ms to 200 ms, wherein between 85% to 100% of the droplets are deposited on the eye.

2. The method of claim 1, wherein the ejected stream of droplets are generated so as to provide the dose of fluid to the eye in more than one pulse of droplet ejection.

3. The method of claim 2, wherein the pulses are generated with stop times separating the pulses.

4. The method of claim 1, further comprising charging the ejected stream of droplets ejected to aid in contact with the eye.

5. The method of claim 4, wherein the ejected stream of droplets is charged by tribocharging as the fluid passes through the plurality of openings in the ejector plate thereby charging the droplets.

6. The method of claim 4, wherein the ejected stream of droplets is charged by applying a voltage to the ejector plate and charging the droplets by induction.

7. The method of claim 4, wherein the ejected stream of droplets is charged by high voltage corona discharge.

8. The method of claim 4, wherein the charging of the ejected stream of droplets attracts the droplets to the eye.

9. The method of claim 1, wherein the ejected stream of droplets are generated to deliver the dose of fluid to the eye between blinks of the eye.

10. The method of claim 1, further comprising warming the fluid to a predefined temperature before generating the ejected stream of droplets.

11. The method of claim 1, further comprising aligning the droplet generating device so that the ejected stream of droplets are directed toward the eye during delivery of the ejected stream of droplets to the eye.

12. The method of claim 11, wherein the aligning is carried out by visual alignment.

13. The method of claim 11, wherein the aligning is carried out with the device including an light emitting diode (LED) to help the subject align the device.

14. A piezoelectric actuated droplet generating device for delivering a fluid to a target as an ejected stream of droplets, the device comprising: a housing; a reservoir disposed within the housing for receiving a volume of fluid; and an ejector mechanism comprising an ejector plate coupled to a fluid delivery area of the reservoir, the ejector plate including a plurality of openings formed through its thickness; and a piezoelectric actuator coupled to the ejector plate, the actuator being operable to oscillate the ejector plate at a frequency to thereby generate the ejected stream of droplets; wherein the ejector mechanism is configured to eject the ejected stream of droplets having an average ejected droplet diameter greater than 20 microns and an average initial droplet ejecting velocity between 2 m/s and 20 m/s such that at least 85% of the mass of the ejected stream of droplets deposit on a target during use.

15. The device of claim 14, wherein the ejector mechanism is configured to eject the ejected stream of droplets having an average ejected droplet diameter in the range of 20 to 100 microns.

* * * * *

UNITED STATES PATENT AND TRADEMARK OFFICE
CERTIFICATE OF CORRECTION

PATENT NO. : 10,154,923 B2
APPLICATION NO. : 14/200268
DATED : December 18, 2018
INVENTOR(S) : Charles Eric Hunter et al.

Page 1 of 1

It is certified that error appears in the above-identified patent and that said Letters Patent is hereby corrected as shown below:

On the Title Page

Under Inventors, replace "Inachulev" with "Ianchulev".

Signed and Sealed this
Second Day of April, 2019

Andrei Iancu
*Director of the United States Patent and Trademark Office*